United States Patent [19]
Chaudhary et al.

[11] Patent Number: 6,160,095
[45] Date of Patent: Dec. 12, 2000

[54] PROTEINS CAPABLE OF REGULATING NF-κB, JNK AND APOPTOSIS PATHWAYS AND METHODS OF USING THE SAME

[75] Inventors: Preet M. Chaudhary, Dallas, Tex.; Leroy Hood, Seattle, Wash.

[73] Assignees: University of Washington, Seattle, Wash.; Stowers Institute for Medical Research, Kansas City, Mo.

[21] Appl. No.: 09/382,155

[22] Filed: Aug. 24, 1999

Related U.S. Application Data

[62] Division of application No. 09/074,044, May 7, 1998.
[51] Int. Cl.[7] .......................... C07K 14/435; C07K 14/47
[52] U.S. Cl. ............................................... 530/350
[58] Field of Search .............................. 530/350

[56] References Cited

U.S. PATENT DOCUMENTS 5,837,837  11/1998  Hunter et al. .......................... 536/23.1

FOREIGN PATENT DOCUMENTS

| 0807686A2 | 11/1997 | European Pat. Off. ........ C12N 15/57 |
| WO97/03998 | 11/1997 | WIPO . | |

OTHER PUBLICATIONS

Boldin et al, Involvement of MACH, a Novel MORT–FAD-D–Interacting Protease, in Fas/APO–1 and TNF Receptor–Induced Cell Death, Cell, vol. 85, pp. 803–815.

*Primary Examiner*—Nancy A. Johnson
*Assistant Examiner*—Karen Canella
*Attorney, Agent, or Firm*—Hovey, Williams, Timmons & Collins

[57] ABSTRACT

Testing methods are provided for determining whether given candidate compounds are effective for regulating NF-κB, JNK and apoptosis cell activities. The methods involve forming a mixture including a compound such as a proteinaceous specie containing two death effector domains (DEDs) or structural or functional homologs and analogs thereof, the candidate compound and a binding target capable of specifically binding to at least one of the DEDs. This mixture is incubated under conditions such that, but for the presence of the candidate compound, the cell activity takes place to a determinable extent. After incubation, the activity is determined and is compared with the determinable extent thereof in the absence of the candidate compound. The assays may be carried out intracellularly or in a cell-free assay. Methods for altering NF-κB, JNK and apoptosis activities in the cell are also provided, and comprise introducing into the cell an activity-regulating amount of a dual DEDs-containing proteinaceous specie.

1 Claim, 26 Drawing Sheets

```
                                   <----------------------------------------DED1-----------
MRITa1       1   ..................MSAEVIHQVEEALDTDEKEMLLFLCRDVAIDVPPNVRDLLDILR.....ERGKLSVGDLA
K13-ORF      1   ..................MATYEVICEVARKLGTDDREVLFLL.NVFIP..QPTLAQLIGALRAL...ERGKLTFPLLA
E8           1   ..................MSHYSMIDTYFSLDEDETETYLYLCRDLLKN..KGEFQCTRDAFKFL...KEEGRLTFPLLA
MC159L       1   .................MSDSKEVPSLPFIRHLLEEIDSHEDSLLLFLCHDAAPG..CTTVTQALCSLS.....SDYACLSAANOM
MC160L       1   ...............MAHEPIPFSFLRNLLAELDASEHEVLRFLCRDVAPA..SKTAEDALRALQ.....QQRKLTLAALV
CASPASE-8    1   ...............MDFSRNLYDIGEQLDSEDLASLKFLSLDYIPQRKQEPIKDALMLFQRLQEKRMLEESNLSFLK
CASPASE-10   1   MKSQGQHWYSSSDKNCKVSFREKLLIIDSNLGVQDVENLKFLCIGLVPNKKLEKSSSASDVFEHLLAGDLLSEEDPFFLA
FADD         1   .................MDPFLVLLHSVSSSLSSSELTELKFLCLGRVGKRKLERVQSGLDLFSMLLEQNDLEPGHTELLR
PEA-15       1   ..................MVEYGTLFQDLTNNITLEDLEQLKSACKEDIPSEKSEEITTGSAWFSFLESHNKLDKDNLSIIE

---->    <----------------------DED2-----------
MRITa1      57   ELLYRVRRFDLLKRILKMDRKAVETHLLRNPH..LVSDYRVLMAEIGEDLDKSD.....VSSLIFLMKDYMGR.GKISKE
K13-ORF     58   ECLFRAGRRDLLRDLLHLDPRFLERHLAGTMS..YFSPYQLTVLHVDGELCARD.....IRSLIFLSKDTIG..SRSTPQ
E8          58   ELLFRVGRLDLIRRIFGQTWTPDSCPRYMP...ICSPFRCLMALVNDFLSDKE.....VEEMYFLCAPRLESHLEPGSK
MC159L      62   EMLYVLQRMDLLKSRFGLS.KEGAEQLLGTS...FLTRYRKLMVCVGEELDSSE.....LRALRLFACNLNPSLSTALSE
MC160L      60   ELLCALRRFDVLKVRFGMT.RECAGRLLGHG...FLSQYRLQVAAINNMVGSED.....LRVMCLCAGKLLP..P.SCTP
CASPASE-8   64   ELLFRINRLDLLITYLNTR.KEEMERELQTPGRAQISAYRVMLYQISEEVSRSE.....LRSFKFLLQEEIS..KCKLDD
CASPASE-10  81   ELLYIIRQKLLQHLNCTK..EEVERLLPTRQ..RVSLFRNLLYELSEGIDSEN.....LKDMIFLLKDSLP...KTEM
FADD        65   ELLASLRRHDLLRRVDDFEAGAAGAAPGEED..LCAAFNVICDNVGKDWRRLAROLKVSDTKIDSIEDRYP..RNLTER
PEA-15      65   HIFEISRRPDLLTMVVDYR...TRVLKISEE....D.ELDTKLTRIPSAKKYKD....IIRQPSEEEIKLG....PPPK

---------->
MRITa1     129   KS.FLDLVVELEKLNLVAPDQLDLLEKCLKNIHRIDLKTKIQKYKQSVQGAGTSYRNVLQAAIQKSLKDPS..NNFRMIT
K13-ORF    129   TS.YTGCTVWKT..........
E8         130   KS.FLRIASLIEDLELLGGDKLTFLIRHLLTTIGRADIVKNLQV...........
MC159L     133   SSRFVELVLALENVGLVSPSSVSVLADMLRTLRRLDLCQQLVEYEQQEQ..ARYRYCYAASPSLPVRTLR..RGHGASE
MC160L     128   RC.LVDIVSALEDAGAISPQDVSVIVTLLHAVCRYDLSVALSAVAHGHMTVGVGTPVQDEPMDVLEVDDAEPMEATPACD
CASPASE-8  136   DMNLLDIFIEMEKRVILGEGKLIDEDNLTCLEDLCKTVVPKLLRNIEKYKREKAIQIVTPPVDKEAESYQG.....
CASPASE-10 148   TS..LSFLAFLEKQGKIDEDNLTCLEDLCKTVVPKLLRNIEKYKREKAIQIVTPPVDKEAESYQG.....
FADD       141   VRESLRIWKNTEKENATVAHLVGALRSCQMNLVADLVQEVQQARDLQNRSGAMSPMSWNSDASTSEAS......
PEA-15     129   KA..........
```

Fig. 11

PROTEINS CAPABLE OF REGULATING NF-κB, JNK AND APOPTOSIS PATHWAYS AND METHODS OF USING THE SAME

RELATED APPLICATION

This is a division of application Ser. No. 09/074,044 filed May 7, 1998.

SEQUENCE LISTING

A printed Sequence Listing accompanies this application, and has also been submitted with identical contents in the form of a computer-readable ASCII file on a floppy diskette.

BACKGROUND OF THE INVENTION

1. Field of the Invention

The present invention is broadly concerned with test methods or assays designed to determine whether a candidate compound has a significant regulating affect upon cell activities, namely NF-κB, JNK and apoptosis, so as to facilitate the discovery and/or design of therapeutic agents. The invention is also concerned with novel proteinaceous species useful in such assays, and to methods for regulating cellular NF-κB, JNK and apoptosis activities for therapeutic purposes.

2. Description of the Prior Art

Nuclear factor-kappa B (NF-κB) is a critical transcription factor which is required for regulated expression of several genes involved in inflammation and immune response. Five known members of this family have been characterized to date and include c-Rel, p52, RelA and RelB. NF-κB is present in the cytoplasm of various cells as an inactive complex with an inhibitory protein called IκB. Stimulation by a number of agents results in the degradation of IκB and subsequent release of NF-κB. Once released, NF-κB is free to migrate to the nucleus and bind to the promoter of specific genes possessing its cognate binding site.

A large number of endogenous and exogenous conditions can lead to the activation of the NF-κB pathway. These include viral and bacterial infections, environmental toxins, UV irradiation, inflammatory cytokines (TNFα, TNFβ, IL-1, IL-17, LIF, etc.), growth factors (IL-2, insulin, M-CSF, PDGF, NGF, etc.), immunoreceptor ligands (e.g., CD3 ligand, CD2 ligand, CD 28 ligand, CD30 ligand, CD 40 ligand, etc.), inflammatory mediators (e.g., Thrombin, angiotensin II, Leukotriene B4), cell adhesion molecules, and several stressful situations (e.g., hypoxia, osmotic shock, hemorrhage, etc.)

Activation of NF-κB leads to the transcriptional activation of several genes which play a crucial role in both innate and acquired immune responses. Some of the noteworthy genes activated by NF-κB include those for cytokines and growth factor such as TNFα, TNFβ, IL-1β, IL-2, I, IL-3, IL-6, IL-8, IL-12, GM-CSF, G-CSF, chemokines, cell adhesion molecules, acute phase proteins and transcription factors p53 and c-myc. In addition, several viruses are activated by NF-κB including the Human immunodeficiency virus 1 (HIV-1) and cytomegalovirus (CMV).

Given the large number of inducers of NF-κB and equally large number of its target genes, it is not surprising that activation of NF-κB has been implicated in the pathogenesis of many acute and chronic inflammatory conditions, such as septic shock, rheumatoid arthritis, Crohn's Disease and atherosclerosis. In addition, NF-κB has a role in oncogenesis and viral transcription regulation, such as in HIV, adenoviruses and papova viruses.

A large number of molecules with immunosuppressive and anti-inflammatory properties have been studied as inhibitors of NF-κB. These include glucocorticoids and other steroid hormones, cyclosporin A, FK506, rapamycin, salicylates and gold compounds. All these compounds are currently being used for the treatment of several human autoimmune and inflammatory disorders which underscores the clinical and commercial importance of NF-κB pathway in the control of inflammation and immune response. However, there are two major problems with the above inhibitors. First, the majority of these compounds have broad range of activities so that they will suppress NF-κB activation by a large number of stimuli. This manifests itself in the form of severe immunosuppression and resulting pre-disposition to opportunistic infections. Second, the majority of these agents have numerous adverse effects associated with the use of these compounds.

Mammalian cells respond to extra cellular stimuli by activation of the MAP kinase family of signaling proteins. Members of the JNK subgroup of MAP kinases are activated in response to diverse extracellular stimuli, including UV irradiation, proinflammatory cytokines and certain mitogens. The JNKs in turn phosphorylate and activate the transcription factor c-Jun, an important component of the transcription activator AP-1. Activation of the JNK pathways has been implicated in a wide variety of responses ranging from cell growth, proliferation, differentiation, cell death, and protection from cell death. As such, this pathway has been implicated in the pathogenesis of human malignancies as well as diseases associated with abnormal cell death. The JNK pathway is activated by several members of the TNFR family. The roll of this pathway and the mediation of cell death by the TNFR family members is still a subject of controversy.

Apoptosis or programmed cell death plays an essential role in the normal growth and development. Abnormalities in this pathway have been linked to the pathogenesis of a number of diseases. For example, failure of cells to undergo apoptosis has been associated with the development of a large number of malignancies, especially low grade lymphomas. Similarly, defects in the apoptosis induced by members of the TNFR family of proteins have been linked to several autoimmune diseases. On the other hand, a large number of diseases are characterized by excessive apoptosis including Alzheimer's disease, AIDS, osteoporosis, ischemic injury, myocardial infarction, and hepatic necrosis. Owing to the central role played by apoptosis in the pathogenesis of several human diseases, the apoptosis pathway and therapies that can modulate this pathway are the focus of extensive research.

Some of the proteins involved in apoptosis have been identified and some interactions among these proteins have been described. However, the mechanisms by which these proteins mediate their activity remains unknown. Given the importance of cell apoptosis and the potential benefits which would flow from effective regulation thereof, considerable research has been undertaken to elucidate the involved proteins and pathway.

Kaposi Sarcoma (KS) is the most common malignancy found in patients with HIV infection. Recent studies have implicated a herpes virus termed Kaposi Sarcoma associated Herpes Virus (KSHV/HHV8) in the pathogenesis of this disease as well as several other malignancies. The mechanism by which KSHV causes malignant transformation is unclear.

Molluscum Contagiosum Virus (MCV) is a benign skin tumor caused by a poxvirus. A hallmark of infection by this virus is an almost complete lack of inflammation in the affected areas which allows the infection to persist for months or even years and to recur after treatment. The mechanism by which MCV blocks the local immune and inflammatory response is unknown.

SUMMARY OF THE INVENTION

The present invention is predicated upon the discovery that certain known molecules as well as novel mutants thereof modulate the signal transduction associated with NF-κB, JNK and apoptosis pathways. In light of this discovery, a number of important screening techniques have been developed, and therapies, including the development of useful pharmacological agents, can be foreseen.

In particular, it has been found that known protein molecules such as Caspase 8, Caspase 10, MRIT-α1, MC159L, MC160L, E8, the N-terminal prodomains of Caspase 8, Caspase 10 and MRIT-α1 and structural or functional homologs and analogs of the foregoing can regulate (i.e., either enhance or inhibit) the NF-κB, JNK and apoptosis pathways. These proteinaceous species are preferably characterized by the presence of an N-terminal prodomain comprising two death effector domains (DEDs) which directly interact with the TRAF family of adaptor proteins and serine-threonine family of protein kinases in order to regulate the pathways. For example, Caspases 8 and 10 activate the NF-κB and JNK pathways; similarly, MRIT-α1, a proteolytically inactive Caspase 8 homolog and K13-ORF, activate both the NF-κB and JNK pathways. The interactions of Caspase 10 with TRAF2 and TRAF5 have been found to pro-apoptotic.

In one aspect of the invention, a method is provided for the testing of candidate compounds such as pharmacological agents and lead compounds therefor. Broadly speaking, such a method involves forming in a cell a mixture including a proteinaceous specie containing two death effector domains (DEDs), the candidate compound, and a binding target protein capable of specifically binding with at least one of the DEDs. This mixture is incubated under conditions such that, but for the presence of the candidate compound, a cell activity selected from the group consisting of NF-κB, JNK and apoptosis takes place to a determinable extent. Finally, the activity is detected and is compared with the determinable extent of the activity in the absence of the candidate compound. This comparison affords a measure of the effectiveness of the candidate compound in regulating the cell activity in question.

Preferably, the proteinaceous specie is formed in situ within the cell by inserting into the cell an expression vector for the proteinaceous species, and causing the vector to express the specie within the cell. Moreover, a reporter gene construct is preferably inserted into the cell having a reporter gene operably linked with a promoter and responsive to the activity; the reporter gene expresses a detectable protein in response to the activity, and the extent of expression of the detectable protein is measured as a measurement of the cell activity. For example, a luciferase reporter construct may be used to good effect in the assays of the invention, and detection methods for luciferase.

The preferred proteinaceous species in accordance with this aspect of the invention comprises a protein fragment having at least about 40 amino acids (more preferably about 50 amino acids) and wherein each of the DEDs therein respectively has at least about 20% homology (i.e., amino acid residue identity) to any of the DED1 or DED2 domains of SEQ ID Nos. 1–16, inclusive. More preferably, the degree of homology is at least about 50%, and more preferably at least about 90%. Comparison for homology among protein fragments is usually performed with sequences between about 6 and 500 residues, preferably between about 10 and 100 residues and more preferably between about 25 and 35 residues. Comparisons for substantial similarity can be performed using any techniques known in the art. Furthermore, limited modifications can be made to the sequences without destroying the biological function of the DEDs-containing proteinaceous species because only a portion of the entire primary sequence is required in order to affect activity. For example, genetically engineered fragments of DEDs-containing proteins, either alone or fused to heterologous proteins, that retain certain activities (i.e., measurable NF-κB, JNK, or apoptosis modulating activity; specific binding ability to TRAFs, serine-threonine protein kinases, etc.) fall within the definition of the DEDs containing proteinaceous species claimed as such. An analysis of the conserved amino profiles of the DEDs confirms that each of the DEDs advantageously comprises the sequence $X_1X_2X_3X_4X_5X_6X_7X_8X_9X_{10}LL$, where $X_1$ is E or H, $X_2$ is L, C, M or I, $X_3$ is L or F, $X_4$ is Y, F, C, A or E, $X_5$ is R, V, A, I or S, $X_6$ is S, L, I, or V, $X_7$ is R, N, Q or G, $X_8$ is R or Q, $X_9$ is F, R, L, M, K, H or P, and $X_{10}$ is D or K. The proteinaceous species should moreover have a molecular weight of from about 5–200 kDa.

In other aspects of the invention, a similar assay method is provided which involves forming a mixture (which may be cell free) including a proteinaceous specie containing two DEDs and selected from the group consisting of K13-ORF, E8, MC159L, MC160L, Caspase 8, Caspase 10, the N-terminal prodomains of Caspase 8, Caspase 10 and MRIT-α1 and structural or functional homologs and analogs of the foregoing. The mixture further has the candidate compound and a binding target capable of binding with at least one of the DEDs and selected from the group consisting of the TRAF proteins. This mixture is incubated under conditions such that, but for the presence of the candidate compound, the binding target-DED specific binding takes place to a determinable extent. Thereafter, the binding target-DED specific binding is detected and is compared with the determinable extent of the binding in the absence of the candidate compound. A similar assay is provided wherein the binding target protein is selected from the group consisting of the serine-threonine kinase proteins, and in such case the proteinaceous specie may be any such specie containing two DEDs.

A variety of cell-free assay techniques may be used in this aspect of the invention, e.g., electrophoretic mobility shift assays, in vitro immunoassays and protein-protein binding assays. Alternately, the assay may be carried out intracellularly, in a manner identical to that described previously; likewise, the assays may be qualitative or quantitative depending upon the desires of the user. Finally, the attributes of the DEDs in the proteinaceous species of this aspect of the invention are identical to those set forth above.

It is to be understood that intracellular assays in accordance with the invention may be carried out without actual addition of the mixture components, i.e., the binding target protein may be (and normally is) a naturally occurring cell protein. Thus, the step of forming a mixture in a cell may involve inserting into the cell an expression vector for the proteinaceous specie, actual addition of the candidate compound, and use of a naturally occurring binding target protein within the cell. Moreover, while mammalian cells are often preferred in the assays of the invention, other types of cells, for example yeast cells may be used.

The assays of the present invention provide efficient methods for identifying pharmacological agents or lead compounds therefor, and as indicted generally involved assaying for compounds which in some manner regulate or modulate a cell activity. The methods are amenable to cost-effective high throughput drug screening and have immediate applicability in a broad range of domestic and international pharmaceutical and biotechnology drug development programs. As understood by those skilled in the art, normally a plurality of assay mixtures are run in parallel with different candidate compound concentrations to obtain a differential response at various concentrations. Typically, a control free of the candidate compound but otherwise identical is run simultaneously with the candidate compound-containing assay mixtures.

The assays of the invention may be quantitative, i.e., a quantitative measurement of cell activity is taken after the incubation step, and this is compared with a quantitative determination of activity in the absence of the candidate compound. Such an assay therefore gives a quantitative measure of the regulation effectiveness of the candidate compound. Alternately, the assays hereof may be qualitative, involving only a qualitative ascertainment of the extent of activity after incubation, in comparison to a qualitative determination of the extent of activity in the absence of the candidate compound.

Candidate compounds encompass numerous chemical classes such as organic compounds having a molecular weight of from about 50–2500 (preferably less than about 1000), proteinaceous species such as proteins, peptides and polypeptides, saccharides, fatty acids, sterols, isoprenoids, purines, pyrimidines, as well as derivatives and structural or functional analogs of the foregoing. Candidate compounds may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural and synthetically produced libraries and compounds are readily modified through conventional chemical, physical, and biochemical means. In addition, known pharmacological agents may be subject to directed or random chemical modifications, such as acylation, alkylation, esterification, amidification, etc., to produce structural analogs.

A variety of other reagents may also be included in the assay mixtures, such as salts, buffers, neutral proteins, detergents and the like. Such agents may be used to facilitate desired binding or to reduce non-specific or background interactions. Also, reagents that otherwise improve the efficiencies of the assays may be used, such as protease inhibitors and antimicrobial agents.

Incubation of the assay mixtures is carried out under conditions whereby, but for the presence of the candidate compound, the cell activity and/or binding target-DED specific binding takes place to a readily determinable extent. The mixture components can be added in any order in the in vitro assays, so long as the requisite binding is allowed to occur. Generally speaking, incubations are carried out at a temperature of from about 4–40° C., more commonly between 15–40° C. Incubation periods normally range between 0.1–36 hours and are preferably less than 5 hours.

After incubation, the extent of measurable activity can be detected by any convenient technique. For cell-free binding type assays, a separation step is often used to separate bound from unbound components. Those skilled in the art are familiar with a number of ways such separations may be effected. Actual detection can be accomplished by directly or indirectly measuring a detectable byproduct of the assay, such as a detectable enzyme in the case of cellular assays. For cell-free binding assays, one of the components usually comprises or is coupled to a detectable label, be it radioactive, luminescent or optical. Again, skilled artisans are familiar with numerous techniques for detecting such labels.

The invention also provides new effective mutants having the sequences of SEQ ID Nos. 26–28. These mutants may be isolated or generated intracellularly as described.

The invention further includes a method for regulating a cell activity selected from the group consisting of NF-κB, JNK and apoptosis comprising the step of introducing into a living cell an activity-regulating amount of a proteinaceous specie not otherwise present in the living cell, the specie taken from the group consisting of Caspase 8, Caspase 10, MRIT-α1, K13-ORF, MC159L, MC160L, E8, the N-terminal prodomains of Caspase 8, Caspase 10 and MRIT-α1 and structural or functional homologs and analogs of the foregoing.

Such therapeutic applications are normally local, involving administration of a selected agent at a site of interest. Various techniques can be used for providing the therapeutic agent at a selected site, such as injection, use of catheters, trocars, projectiles, pluronic gel, stents, sustained drug release polymers, or other expedient which provides for internal access.

As used herein, the term "structural or functional homologs and analogs and analogs" in reference to a proteinaceous specie or binding target is intended to mean species having similar, non-identical sequence(s) considered by those skilled in the art to be functionally equivalent to the specific proteinaceous specie or binding target in question, as well as non-proteinaceous compounds such as synthetic analogs or mimics which have the same functional properties in the methods of the invention as the DEDs-containing proteins or binding targets, as the case may be. For example, the sequence of a given proteinaceous specie or binding target may be altered by substitution, deletion or addition of amino acid residues which have no, or very little, effect upon the functionality of the specie or target. Similarly, spliced isoforms and active fragments having the desired functionality may be used. Functionally equivalent synthetic mimics are known in the art and could be used in lieu of actual proteinaceous species or binding targets. All such alterations and substitutions are intended to be encompassed as "structural or functional homologs and analogs." The term "isolated" in reference to a proteinaceous specie means a specie that is relatively free from contaminating lipids, polypeptides, nucleic acids or other cellular material which may be associated with the specie in a cell.

BRIEF DESCRIPTION OF THE DRAWINGS

FIG. 11 is a homology matrix depicting the degrees of homology between the DED1 and DED2 domains of MRIT-α1, K13-ORF, E8, MC159L, MC160L, Caspase 8, Caspase 10, FADD and PEA-15;

BRIEF DESCRIPTION OF THE SEQ IDs

Figure 1:
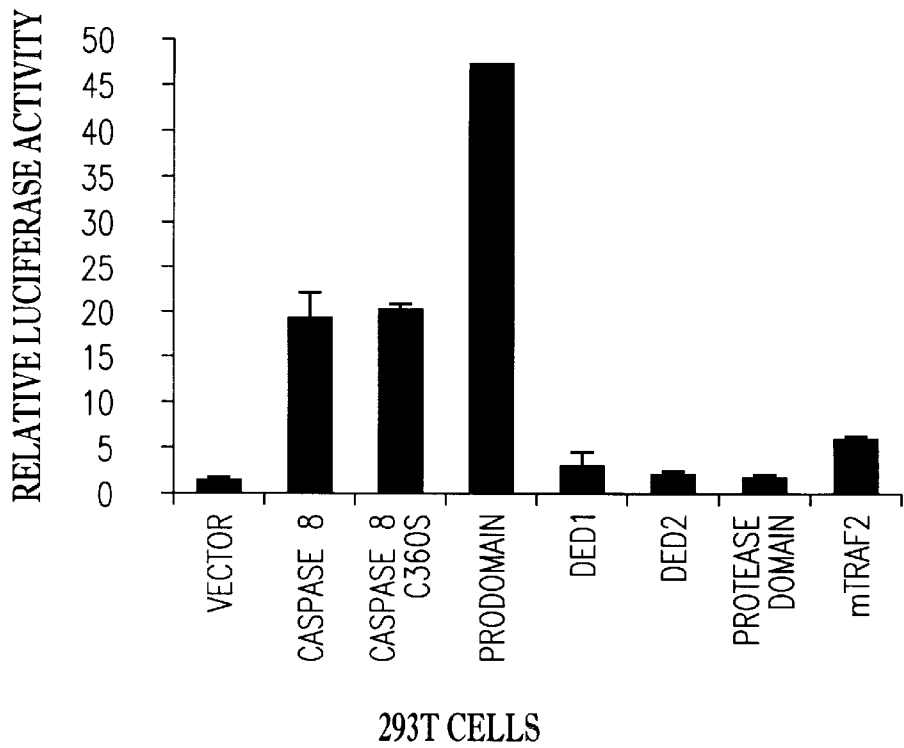
FIG. 1 is a graph illustrating the extent of expression of luciferase reporter enzyme in a series of intracellular tests wherein respective Caspase 8 constructs were expressed in 293T cells to determine their effect upon NF-κB pathway activity, as compared with a null vector control.

SEQ ID Nos. 1–16, inclusive are respectively the DED1 and DED2 sequences for MRIT, K13-ORF, E8, MC159L, MC160L, Capase 8, Capase 10, FADD and PEA-15;

SEQ ID Nos. 17–25, inclusive, are respectively the entire prodomain sequences for MRIT, Caspase 8, FADD, K13-ORF, MC159L, MC160L, E8, PEA-15, and Caspase 10; and SEQ ID Nos. 26–28, inclusive, are respectively the sequences for the mutants for Caspase 8 (D73A), Caspase 8 (L74A) and Caspase 8 (L75A).

DETAILED DESCRIPTION OF THE PREFERRED EMBODIMENTS

The following examples set forth preferred procedures and proteinaceous species useful in the context of the invention. It is to be understood, however, that these examples are provided by way of illustration only and nothing therein should be taken as a limitation upon the overall scope of the invention.

Materials 293T and MCF7 cells were obtained from Dr. David Han (University of Washington, Seattle, Wash.). 293EBNA cells were obtained from Invitrogen. All cells were maintained in DMEM media with 10% fetal calf serum at 37 C with 5% carbon dioxide.

Rabbit polyclonal antibodies against FLAG, HA and myc-tags were obtained from Santa Cruz Laboratories. Antibodies against the AU1 epitope-tags were obtained from Babco. Myc beads and Flag beads were obtained from Santa Cruz Laboratories, Santa Cruz, Calif. and Kodak Scientific Imaging Systems, New Haven, Conn., respectively.

Methods—Expression constructs

All cDNA clones refer to the human sequences unless specified otherwise. The sequences and/or expression constructs for cDNAs clones encoding the following molecules have been previously described in the listed references: Caspase 8 (FLICE; GenBank U58143) (Muzio et al., *Cell*, 85:817–827, 1996); Caspase 7 (ICE-LAP3; GenBank U39613) (Duan et al., *J. Biol Chem*, 271:1621–1625, 1996); Caspase 10 (Mch4; GenBank Q92851) and its active site mutant (i.e. Caspase 10 C358A) (Fernanes-Alnemri et al., *Proc. Nat'l Acad Sci U.S.A.*, 93:7464–7469, 1996); Caspase 10 (FLICE2) (Vincenz et al., *J Biol Chem*, 272:6578–6583, 1997); Caspase 9 (ICE-LAP6; GenBank P55211) (Duan et al., *J Biol Chem*, 271:16720–16724, 1996); Caspase 3 (YAMA; GenBank P42574) (Tewari et al., *Cell*, 81:801–809, 1995); Caspase 2—GenBank P42575 (Wang et al., *Cell*, 78:739–750,1994); Caspase 1—GenBank P89116 (Thornberry et al., *Nature*,356:768-764,1992); FADD—GenBank Q13158 (Chinnaiyan et al., *Cell*, 81:505–512; 1995); E8 (PIR Database S55668) and MC159L (GenBank U60315) (Hu et al., *J Biol Chem*, 272:9621–96214, 1997); TNFR1 (GenBank P19438) and DR3 (GenBank U83597) (Chinnaiyan et al., *Science*, 274:990–992, 1996); crmA, cowpox serpin, (Tewari et al., *J Biol Chem*, 270:3255–3260, 1995); CD40 (GenBank P25942) (Stamenkovic et al., *Embo J*, 8:1403–1410,1989); NIK (NF-κB-inducible kinase, GenBank Y10256), NIKΔ1234 and NIKΔ2101 (dominant negative NIK) (Natoli et al., *J Biol Chem*, 272:26079–26082, 1997); mTRAF1 (GenBank P39428) and mTRAF2 (GenBank P39429) (Rothe et al., *Cell*, 78:681–692,1994); TRAF3 (GenBank U15637) (Cheng et al., *Science*, 267:1494–1498; 1995); mTRAF5 (GenBank D83528) (Nakano et al., *J Biol Chem*, 271:14661–14664,1996); A20 (Sarma et al., *J Biol Chem*, 270:12343–12346, 1995); I-TRAF (Rothe et al., *Proc Nat'l Acad Sci U.S.A.*, 93:8241–8246, 1996); IKK1 (GenBank AF009225, IKK2 (GenBank AF029684) and their mutants (Nakano et al., *Proc Nat'l Acad Sci U.S.A.*, 95:3537–3542, 1998); DN-IκBα or IκBα-ΔN (missing the N-terminal 36 amino acids) (Brockman et al., *Mol Cell Biol*, 15:2809–18; 1995); NF-κB driven luciferase reporter construct (Berberich et al., *J Immunol*, 153:4357–66; 1994); and, JIP (Dickens et al., *Science*, 277:693–696,1997). These constructs were either used directly or further modified to add appropriate epitope-tags using PCR and standard molecular biology cloning techniques as described in *Molecular Cloning*, 2d Ed. by Sambrook, Fritsch, Maniatis, Cold Spring Harbor Laboratory Press, 1989, incorporated by reference herein. An RSV promoter driven β-galactosidase reporter construct was a gift of Dr. Mark Kay (University of Washington).

Constructs encoding K13-ORF (GenBank U90534) were prepared by PCR amplification of the desired coding sequence from a human genomic DNA sample containing KSHV/HHV8 (human herpesvirus 8) genomic DNA and was obtained from Dr. Tim Rose (University of Washington, Seattle, Wash.). Primers for PCR amplification were based on the published sequence of K13-ORF and carried additional sequences at their 5' end for subsequent restriction digestion and cloning of the amplified insert. Constructs encoding p35 were similarly prepared by using a bacuolovirus vector pFastBac HTa (Life Technologies, Inc., catalog no. 10584-027) DNA as the template. Constructs encoding mTRAF1, mTRAF2, TRAF3, I-TRAF, and PEA-15 (GenBank Q15121), mTRAF5, and Lymphotoxin β Receptor (LBPR) were similarly prepared using IMAGE consortium EST clones as templates:

| | |
|---|---|
| mTRAF1 | 636225 |
| mTRAF2 | 439083 |
| mTRAF5 | 568002 |
| TRAF3 | 290035 |
| I-TRAF | 638576 |
| PEA-15 | 361256 |
| LTBR | 810443 |

All EST clones were obtained from the Genome Systems, Inc., St. Louis, Mo.

Myc-epitope tagged constructs encoding CD40 (a.a. 16 to 277), and LTBR (Gen Bank P36941) (a.a. 28-435) were similarly prepared by amplifying the corresponding inserts using custom primers and using a CD40 cDNA and IMAGE consortium EST clone as templates respectively. The amplified products were subsequently cloned in to a modified pSecTag A vector (Invitrogen) containing a DNA segment encoding a Myc-epitope (EQKLISEEDL) downstream and in-frame with a murine Ig κ-chain signal peptide. Myc-tagged DR3, DR4 (GenBank U90875), DR5 (GenBank AF016268) and Fas were similarly constructed as previously described (Chaudhary et al., *Immunity*, 7:821–830; 1997). A construct encoding RIP-HA has also been described previously (Chaudhary et al., *Immunity*, 7:821–830, 1997). The expression constructs encoding His-tagged MRIT-α1 (GenBank U85059) and MRIT-β1 (GenBank Y14040) are described in Han et al., *Proc Nat'l Acad Sci U.S.A.*, 94:11333–11338 (1997). Unless specified otherwise, the construct MRIT refers to the MRIT-α1 isoform. Constructs encoding FLAG-TRAF6 and FLAG-CD28/MTRAF5 were as described in Duckett et al., *Genes Dev* 11:2810–21 (1997). Unless specified otherwise, the various epitope-tagged mammalian expression constructs were constructed in the pcDNA3 expression vector (Invitrogen). All TRAF5 constructs refer to the murine TRAF5 cDNA clone. Although murine clones for TRAF5, TRAF1 and TRAF2 have been used in this invention, the corresponding human clones are likely to behave in a similar fashion. Similarly, catalytically active site mutant proteins for Caspases (i.e., Caspase 8 C360S, Caspase 10 C358A, Caspase 9 C288S, and Caspase 7 C186S) were used for assays involving activation of NF-κB and JNK pathways and for binding studies. This was done for the ease of experimental design based on the lack of cytotoxicity of these proteins. It is expected that the corresponding wild-type Caspases will have similar properties in the above studies.

C-terminal FLAG Epitope Expression Vectors

The C-terminal FLAG epitope expression vectors encoding Caspase 8, Caspase 8 C360S, Caspase 8 prodomain, Caspase 8 protease domain, Caspase 3, MRIT-α1, MRIT-β1, mTRAF2, mTRAF5, RIP (GenBank Q13546), K13-ORF, MC159L, E8 and PEA-15 were constructed by joining in-frame a DNA segment encoding the following amino acid sequence to the 3' end of the protein-coding sequences of cDNAs encoding the above proteins: ETDFYDYKD-DDDK.

C-terminal HA Epitope Expression Vectors

The C-terminal HA (Heamagglutinin) epitope expression vectors encoding mTRAF1, mTRAF2, I-TRAF, TRAF3, mTRAF5, RIP, K13-ORF, MC159L, E8 and PEA-15 were constructed by joining in-frame a DNA segment encoding the following amino acid sequence to the 3' end of the protein-coding sequences of the cDNAs encoding the above proteins: ETDFYPYDVPDYA C-terminal myc Epitope Expression Vectors.

The C-terminal myc epitope expression vectors encoding Caspase 8, Caspase 8 C360S, Caspase 8 prodomain, and Caspase 8 protease domain were constructed by joining in-frame a DNA segment encoding the following amino acid sequence to the 3' end of the protein-coding sequences of the cDNAs encoding the above proteins: ETDFYEQKLI-SEEDL.

Generation of Various Other Expression Vectors

To generate the expression vectors encoding the DED1 (amino acids 1–103), DED2 (amino acids 104–180) or the protease domain (a.a. 217-479) of Caspase 8, the corresponding inserts were amplified with PCR using a Caspase 8 cDNA as a template and subsequently cloned into the mammalian expression vector pcDNA3 (Invitrogen).

ND-Caspase 8 is missing the first 42 amino acids of Caspase 8 and was generating by deleting the first 51 nucleic acids of FLAG-Caspase 8 cDNA clone by taking advantage of a Bgl II site in the Caspase 8 sequence. As a result of this deletion, the original start site is deleted so that translation starts at the methionine residue at position 43.

DN-mTRAF2 is missing the DNA encoding the first 87 amino acids and was generated by using PCR with custom primers to amplify the DNA encoding the a.a. 88-501 of mTRAF2 and incorporating a start site (i.e. methionine residue) at the N-terminus.

DN-mTRAF5 was constructed similarly to DN-mTRAF2, deleting the first 204 amino acids of mTRAF5 clone.

Caspase 8 Mutants

Caspase 8 C360S has the amino acid cysteine (C) at the residue 360 replaced by amino acid serine (S). Similar nomenclature applies to the mutants Caspase 8 D73A, L74A, and L75A as well as to Caspase 9 C288S and Caspase 7 C186S. To generate Flag-tagged Caspase 8 C360S, Quickchange site directed mutagenesis kit from Stratagene (La Jolla, Calif.) was used. Flag-tagged Caspase 8 cDNA was used as a template for mutagenesis. The sequence of the primers was as follows:

Upper primer:
5' GTGTTTTTTATTCAGGCTAGTCAGGGGGATAACTACCAGAA 3' (SEQ ID NO:29)

Lower primer:
5' TTCTGGTAGTTATCCCCCTGACTAGCCTGAATAAAAAACAC 3' (SEQ ID NO:30)

Mutagenesis was performed by following the manufacturer's instructions. The sequence of the mutated construct was confirmed by automated fluorescent dye-terminator sequencing on an ABI 373 sequencing machine.

The same approach was used to generate the mutants in the DEDs of Caspase 8. The primers used were as following:

For Caspase 8 D73A:

Upper primer:
5' TAATAGACTGGCTTTGCTGATTAC 3' (SEQ ID NO:31)
Lower primer:
5' GTAATCAGCAAAGCCAGTCTATTA 3' (SEQ ID NO:32)

For Caspase 8 L74A:

Upper primer:
5' AATAGACTGGATGCGCTGATTACC 3' (SEQ ID NO:33)
Lower primer:
5' GGTAATCAGCGCATCCAGTCTATT 3' (SEQ ID NO:34)

For Caspase 8 L75A:

Upper primer:
5' GACTGGATTTGGCGATTACCTACC 3' (SEQ ID NO:35)
Lower primer:
5' GGTAGGTAATCGCCAAATCCAGTC 3' (SEQ ID NO:36)

Mutants of Other Caspases

Flag-tagged Caspase 7 C186S and Caspase 9 C288S were constructed in a manner similar to that of the Caspase 8 mutants, using Flag-tagged Caspase 7 or Caspase 9 cDNA as a template for mutagenesis. The sequence of the primers was as follows:

For Caspase 7 C186S:

Upper primer:
5' TCTTCATTCAGGCTAGCCGAGGGACCGAG 3' (SEQ ID NO:37)
Lower primer:
5' CTCGGTCCCTCGGCTAGCCTGAATGAAGA 3' (SEQ ID NO:38)

For Caspase 9 C288S:

Upper primer:
5' TTCATCCAGGCCaGTGGTGGGGAGC 3' (SEQ ID NO:39)
Lower primer:
5' GCTCCCCACCACTGGCCTGGATGAA 3' (SEQ ID NO:40)

Caspase 10 PRO (a.a. 1-191) was constructed by amplifying the corresponding DNA coding for the desired sequence using PCR and custom primers and subsequent cloning in the pcDNA3 expression vector.

EXAMPLE 1

The following assays were conducted on both 293T cells and on MCF7 cells to determine the ability of various constructs of Caspase 8 to activate the NF-κB pathway.

Transfection of 293T Cells 293T cells (1×10$^5$) were seeded in each well of a 24 well tissue culture plate and 24 hours later transfected with either a test vector containing a construct (750 ng) or a control plasmid (750 ng), along with an NF-κB/luciferase reporter construct (75 ng) and an RSV promoter driven β-galactosidase reporter construct (pRcRSV/LacZ) (75 ng) in duplicate using a calcium phosphate coprecipitation method. The calcium phosphate coprecipitation method comprises a 2× HEPES solution (8 g NaCl, 1.5 mM Na$_2$HPO$_4$, 6.5 g HEPES, an amount of H$_2$O adequate to bring the total volume of the solution to 500 ml, pH of 7.0, stored at 4° C.) and 2M CaCl₂ stored in aliquots at −20° C. Two and one half (2.5) μl of 2M CaCl₂ solution was mixed with the desired DNA construct solutions (dissolved in a buffer containing 10 mM Tris, 1 mM EDTA, and pH=8) and water in an amount to bring the total volume of the complete solution to 20 μl. To this solution, 20 μl of the 2× HEPES solution was added dropwise and the resulting precipitate was sprinkled over the cells in a well of the 24-well Tissue culture plate (Falcon). Each experiment was performed in duplicate.

Transfection of MCF7 Cells

MCF7 cells (1×10⁵) were transfected using 3 μl Superfect (obtained from Qiagen in Valencia, Calif.), following the Manufacturer's instructions which accompany the Superfect and as described in Chaudhary et al., *Immunity* 7:831-830 (1997).

Luciferase Assays of 293T and MCF7 Cells

Twenty four hours after transfection, cell extracts were prepared using the Luciferase Cell Culture Lysis Reagent (Promega, Madison, Wis.; Catalog #E1531). Luciferase assays of the lysates were performed using 20 μl of cell extract as described *Current Protocols in Molecular Biology*, Vol. 1, Chap. 9.7B, John Wiley & Sons, Inc. (1995), incorporated by reference herein, with the exception that 100 μl of a 200 μM luciferin solution dissolved in the luciferase assay was added directly to each sample using an automated injector from a Gene-Probe Luminometer (Berthoid). The cell lysate was diluted 1 to 20 times with Phosphate Buffered Saline (pH=7.4) (Life Technologies, Inc., Gaithersburg, Md.) and the β-galactosidase activity was measured as described in *Molecular Cloning*, 2d edition, by Sambrook, Fritsch, Maniatis, Cold Spring Harbor Laboratory Press, 1989, incorporated by reference herein, except that the reaction was stopped by addition of 150 μl of 1M Tris pH 8. Absorbance of the final colored product was measured at 415 nm using a Bio-Rad model 3550 microplate reader. Luciferase activity was normalized relative to the β-galactosidase activity to control for the difference in the transfection efficiency. The above procedure was repeated with each test vector listed in FIG. 1.

Results

Figure 2:
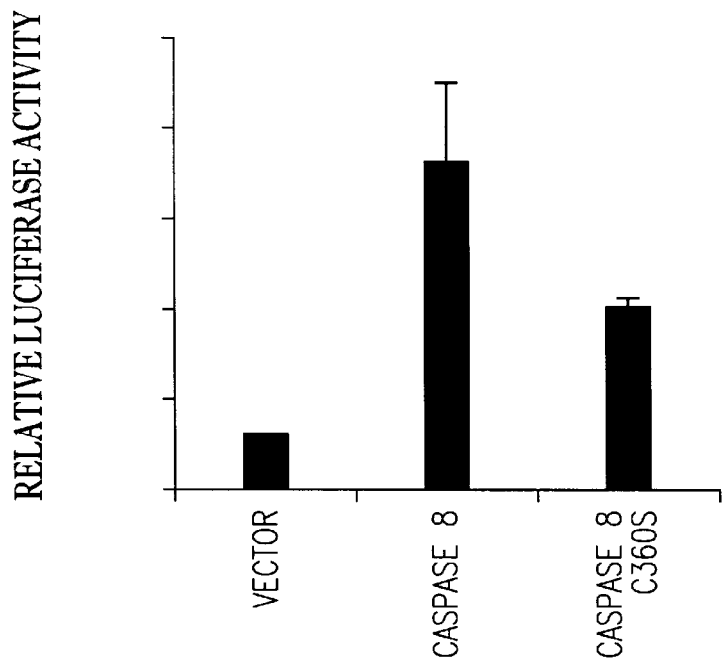
FIG. 2 is a graph similar to that of FIG. 1 illustrating the expression of luciferase in a series of intracellular tests wherein Caspase 8 and a Caspase 8 mutant (C360S) were expressed in MCF-7 human breast cancer cells to determine their effect upon NF-κB pathway activity, as compared with a null vector control.

As shown in FIG. 1, expression of Caspase 8 in 293T cells led to significant activation of the NF-κB/luciferase reporter construct as compared to the control vector. An active site mutant of Caspase 8 containing a cysteine to serine mutation at the catalytic active site (i.e., Caspase 8 C360S) was as effective as the wild-type Caspase 8 in activating the NF-κB pathway. This mutant is incapable of induction of apoptosis when over-expressed in the 293T cells. Caspase 8 also activated NF-κB in the MCF-7 human breast cancer cell line (see FIG. 2). To determine the domains of Caspase 8 that are responsible for NF-κB activation, the above experiment was repeated with different deletion constructs of Caspase 8. A construct containing the full-length prodomain, (i.e., containing the two DEDs (a.a. 1-180)), was able to activate NF-κB to a greater extent than the full-length Caspase 8. However, deletion constructs encoding either DED1 (a.a. 1-103) or DED2 (a.a. 104-180) failed to do so. Similarly, a construct encoding the full-length protease domain failed to activate NF-κB. These results confirm that the NF-κB induction by Caspase 8 depend on an intact prodomain containing two DEDs and is independent of the protease domain or the protease/apoptosis inducing activity of Caspase 8.

EXAMPLE 2

Caspase 10 (Mch4 isoform)

Figure 3:
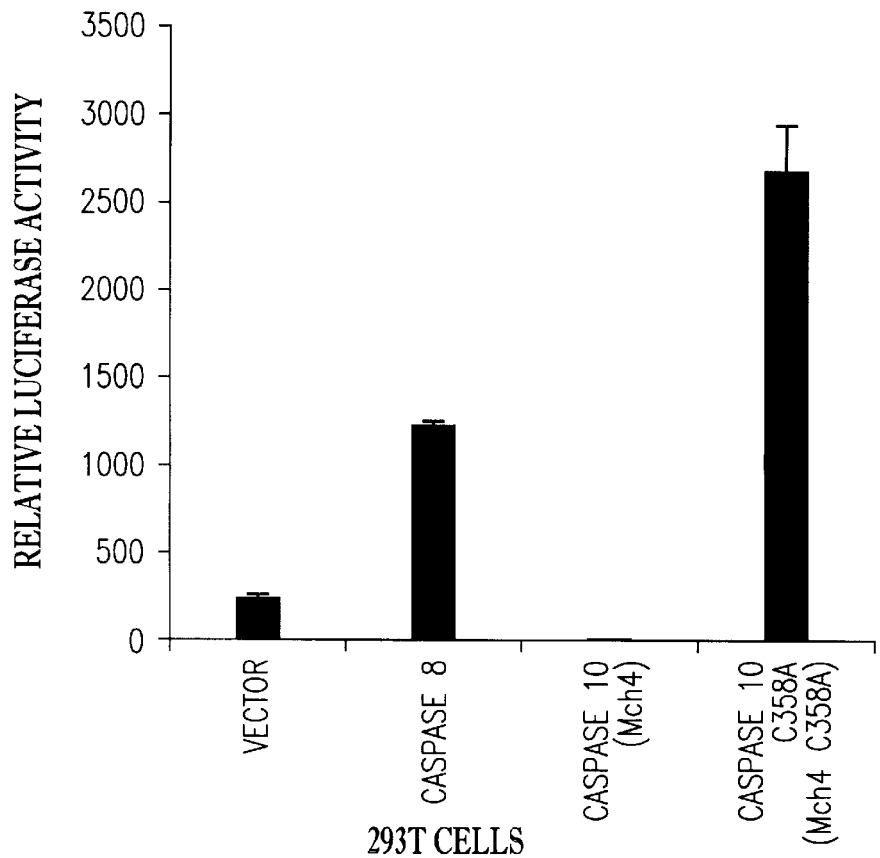
FIG. 3 is a graph similar to that of FIG. 1 illustrating the expression of luciferase in a series of intracellular tests wherein Caspase 8, Caspase 10 Mch4 isoform and a Caspase 10 mutant (C358A) were expressed in 293T cells to determine their effect upon NF-κB pathway activity, as compared with a null vector control.

In this experiment, the ability of Caspase 10 (Mch4 isoform) to activate NF-κB was tested in 293T cells using the procedure described in Example 1. Caspase 10 is a homolog of Caspase 8 and possesses a prodomain homologous to Caspase 8. Unlike Caspase 8, Caspase 10 is highly cytotoxic in 293T cells. This experiment therefore tested the ability of a proteolytically inactive mutant of Caspase 10 containing a cysteine to alanine mutation at the active site, to activate NF-κB. The results of this test are shown in FIG. 3. This mutant was highly effective in activating NF-κB.

Caspase 10 (FLICE2 isoform)

Figure 4:
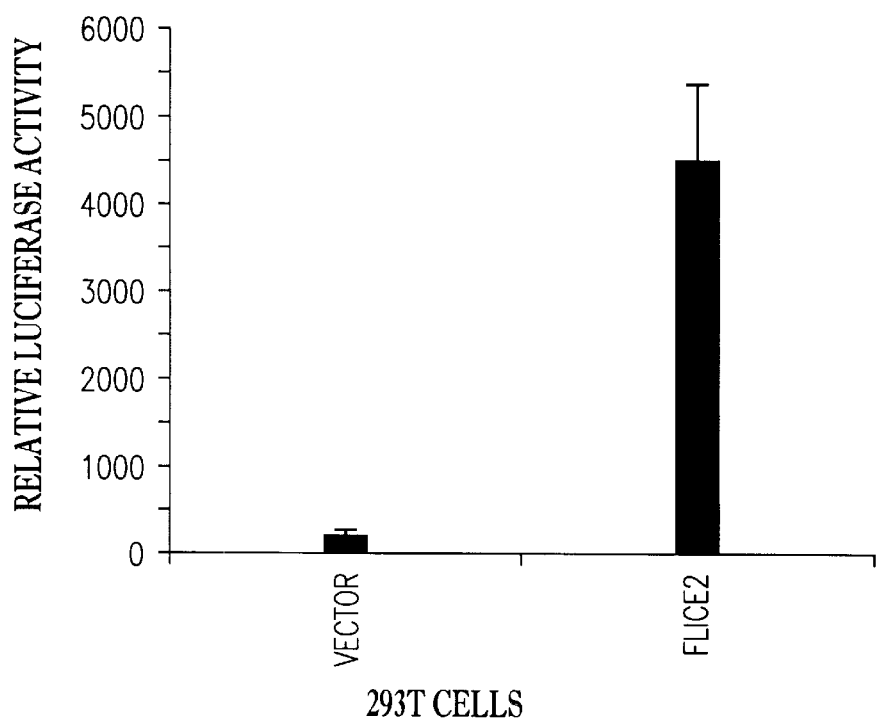
FIG. 4 is a graph similar to that of FIG. 1 illustrating the expression of luciferase in an intracellular test wherein Caspase 10 FLICE2 was expressed in 293T cells to determine their effect upon NF-κB pathway activity, as compared with a null vector control.

In order to rule out the possibility that the above ability to activate NF-κB was secondary to the mutation of the active site, the ability of Caspase 10 (FLICE2 isoform) to activate the NF-κB pathway was tested utilizing the above assay (see FIG. 4). Unlike the Mch4 isoform, FLICE2 isoform is not cytotoxic. The FLICE2 isoform was also able to effectively activate NF-κB. This confirms that the wild-type Caspase 10 has the ability to activate NF-κB.

EXAMPLE 3

Figure 5:
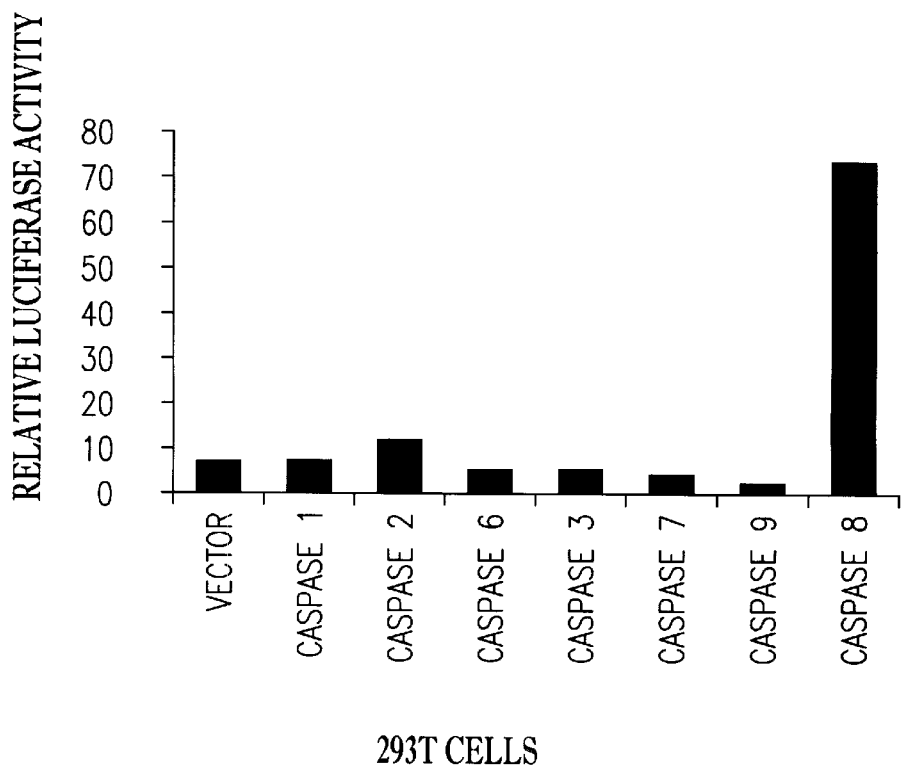
FIG. 5 is a graph similar to that of FIG. 1 illustrating the expression of luciferase in a series of intracellular tests wherein various Caspases were expressed in 293T cells to determine their effect upon NF-κB pathway activity, as compared with a null vector control.

These experiments tested the ability of several other Caspase family members (Caspases 1, 2, 3, 6, 7, 9) to activate the NF-κB pathway in 293T cells. The test is procedures followed were identical to those of Example 1, substituting the particular Caspase family member for the test vector. The other family members possess a protease domain homologous to Caspase 8 but do not possess a DEDs-containing prodomain. As can be seen in FIG. 5, none of the other Caspase family members were able to activate the NF-κB pathway. Caspase 8, however, effectively activated the NF-κB pathway. These results confirm the importance of DEDs in activation of the NF-κ pathway.

EXAMPLE 4

In this experiment, the ability of MRIT (both MRIT-α1 and MRIT-β1 isoforms) to induce the NF-κB pathway in the 293T cells was analyzed. MRIT resembles Caspase 8 in that it possesses a prodomain consisting of two homologous DEDs. The procedure followed was as set forth in Example 1.

Figure 6:
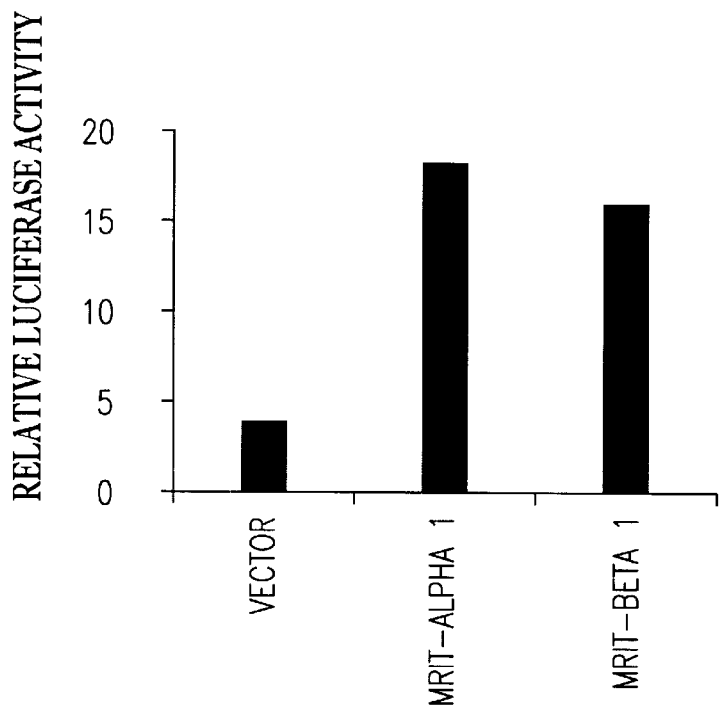
FIG. 6 is a graph similar to that of FIG. 1 illustrating the expression of luciferase in a series of intracellular tests wherein MRIT-α1 and MRIT-β1 isoforms of MRIT were expressed in 293T cells to determine their effect upon NF-κB pathway activity, as compared with a null vector control.

The results are shown in FIG. 6. Compared to the control, MRIT-α1 effectively activated the NF-κB pathway. The MRIT-β1 isoform which contains the two DEDs was as effective as the full length MRIT-α1 in activating NF-κB. This further confirms the role of MRIT in activating NF-κB and localizes this activity to its prodomain.

Following the procedure for MCF7 cell transfection shown in Example 1, it was also determined that MRIT-α1 also activated NF-κB in the MCF7 cells.

EXAMPLE 4a

Figure 7:
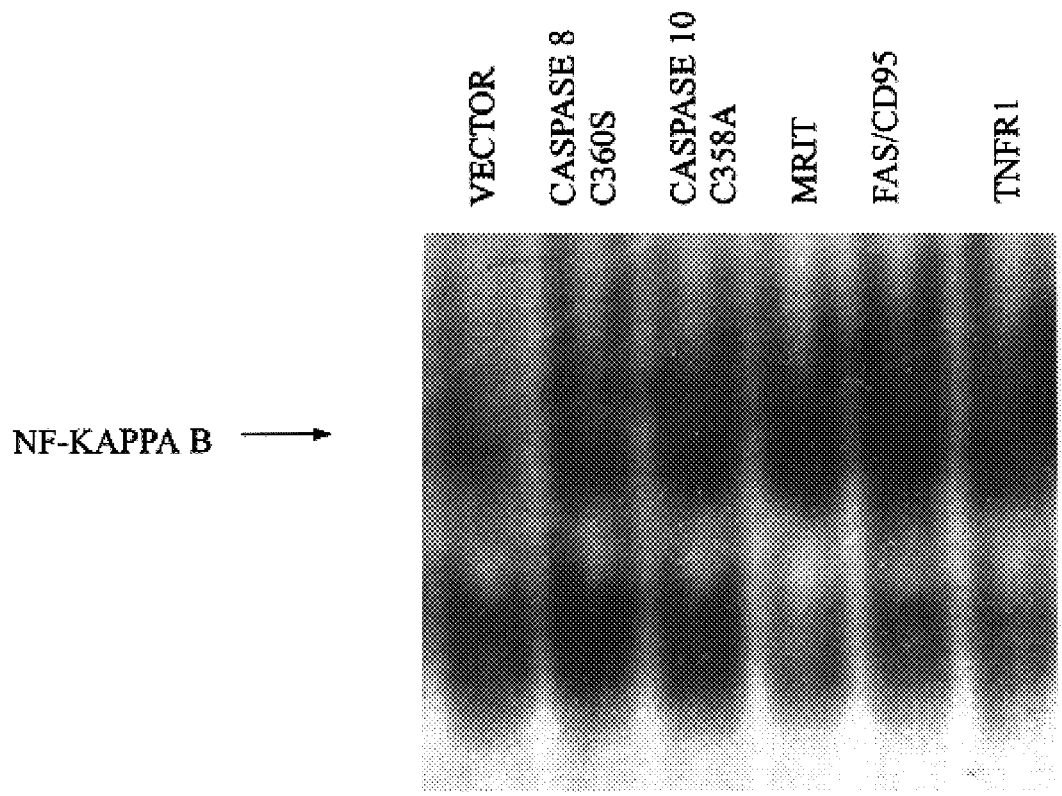
FIG. 7 is a photograph illustrating electrophoretic gel mobility shift assay test results wherein the effect of expression of Caspase 8 mutant (C360S), Caspase 10 mutant (C358A), MRIT-α1, FAS/CD95, and TNFR1 was determined as compared with a null vector control.

The NF-κB activation mediated by Caspase 8, 10, and MRIT was confined using an independent assay based on electrophoretic mobility shift (see FIG. 7). For this assay, 293T cells were (1×10⁶) transfected with a control vector or an expression vector encoding Caspase 8 C360S, Caspase 10 C358A, MRIT, CD95/Fas or TNFR1 (5 mg each). After 36 hours, nuclear extracts were prepared as described in Schreiber et al., Rapid detection of octamer binding proteins with "mini extracts", prepared from a small number of cells, *Nucleic Acids Res,* 17(15):6419 (1989). Nuclear extracts (2 μl) were incubated for 30 minutes at room temperature with a ³³P labeled NF-κB duplex oligonucleotide (Promega, Madison, Wis.; catalog no. E3292) in a buffer containing 10 mM HEPES (pH 7.9); 50 mM KCl, 0.2 mM EDTA, 2.5 mM DTT, 10% glycerol and 0.5% NP-40. Protein-DNA complexes were resolved on a 5% native polyacrylamide and run in 0.5× TBE. Gel was dried and autoradiographed.

One skilled in the art will appreciate that the electrophoretic mobility shift assay and the Luciferase-based reporter assay are only two of numerous assays which could be utilized to measure activation of NF-κB pathway. Other workable assays include Chloramphenicol Acyl Transferase Assay (CAT) and Secreatory alkaline phosphatase (SEAP).

EXAMPLE 5

Figure 8:
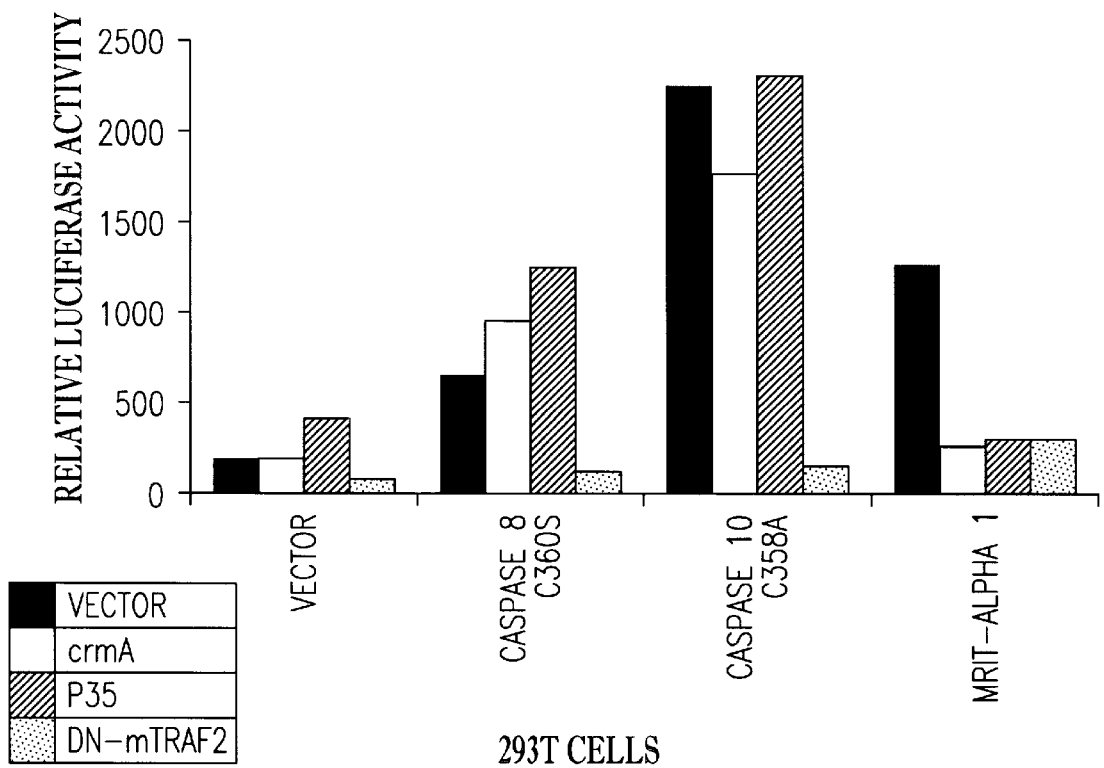
FIG. 8 is a graph similar to that of FIG. 1 illustrating the expression of luciferase in a series of intracellular tests wherein the effect of crmA, p35 and DN-mTRAF2 on NF-κB activity induced by Caspase 8 mutant (C360S), Caspase 10 mutant (C358A) and MRIT-α1 in 293T cells was measured, as compared with a null vector control.

This example illustrates the effect of various molecules on Caspase- and MRIT-induced NF-κB activation. The experiments were conducted as described in Example 1 with the following modifications: the amount of test plasmid (i.e., Caspase 8 C360S, Caspase 10 C358A, MRIT, or control vector) used was 100 ng/well, and a second plasmid (i.e., control vector, crmA, p35, or DN-mTRAF2) was co-transfected along with the test plasmid at 750 ng/well. The results of these tests, set forth in FIG. 8, indicate that MRIT-induced NF-κB activation can be inhibited by crmA, p35, and DN-mTRAF2. However, only DN-mTRAF2 can block Caspase 8- and Caspase 10-induced NF-κB activation. This example indicates that an NF-κB-based functional assay can be utilized as a screening tool for identifying lead compounds for pharmacological agents capable of selectively blocking Caspase 8-, Caspase 10-, and/or MRIT-induced NF-κB signal transduction pathways.

EXAMPLE 6

Figure 9:
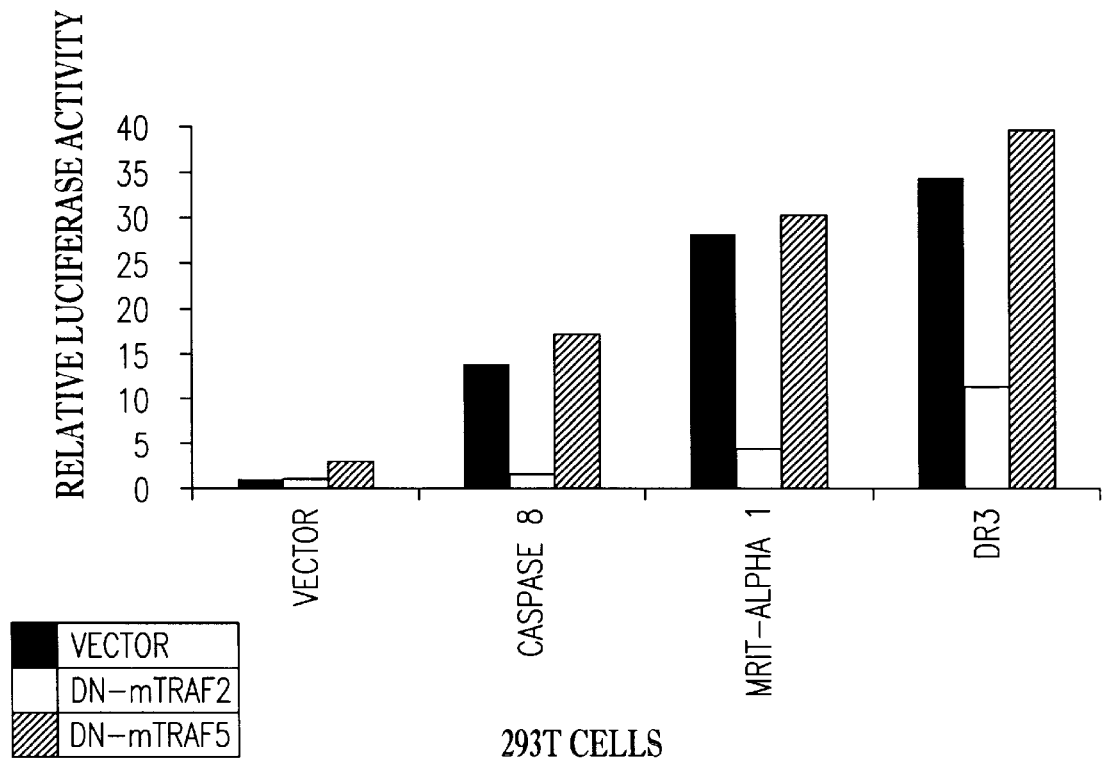
FIG. 9 is a graph similar to that of FIG. 8 illustrating the expression of luciferase in a series of intracellular tests wherein the effect of DN-mTRAF2 and DN-mTRAF5 on NF-κB activity induced by Caspase 8, MRIT-α1 and DR3 in 293T cells was measured, as compared with a null vector control.

The object of this test was to determine whether DN-mTRAF5 can block Caspase 8 -, MRIT- and DR3 -induced NF-κB pathway activation. The procedures followed were identical to those of Example 5, using 100 ng/well of the first plasmid (i.e., control vector, Caspase 8, MRIT, and DR3) and 750 ng/well of the second plasmid (i.e., control vector, DN-mTRAF2, and DN-mTRAF5). The results are shown in FIG. 9 and demonstrate that DN-mTRAF5 does not block Caspase 8- and MRIT-induced NF-κB. Therefore, Caspase 8- and MRIT-induced NF-κB activation does not depend upon TRAF5.

EXAMPLE 7

Figure 10:
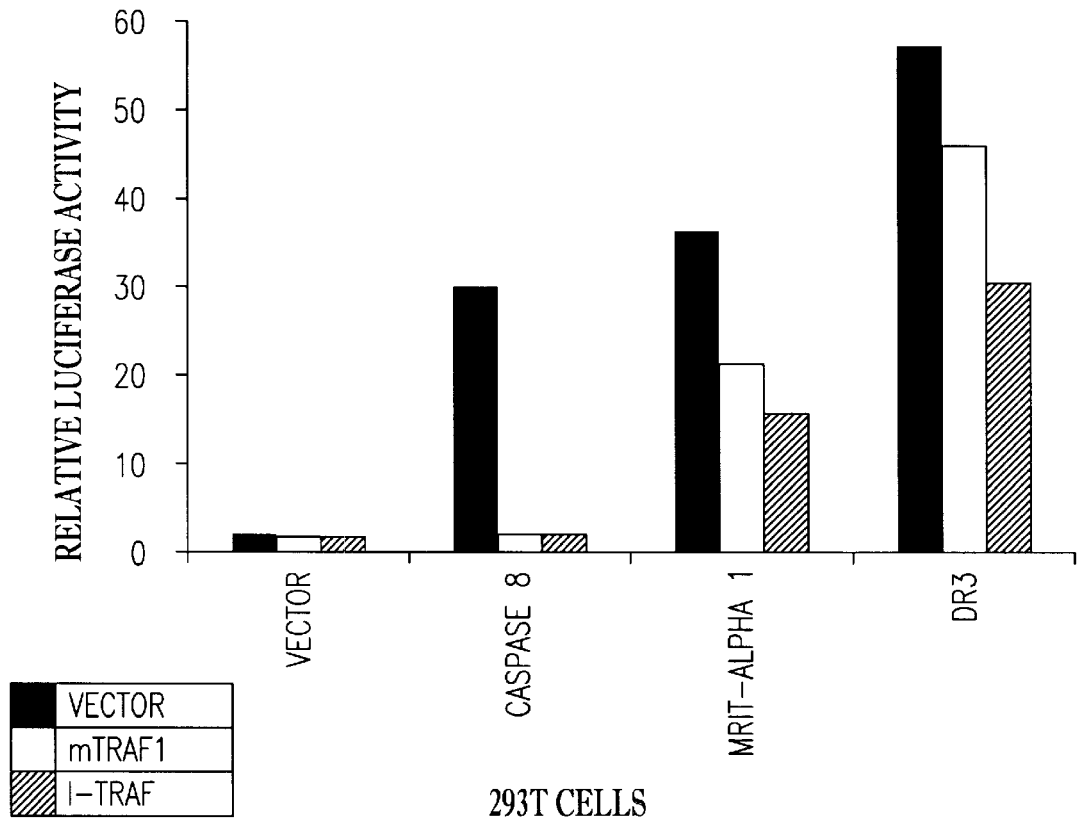
FIG. 10 is a graph similar to that of FIG. 8 illustrating the expression of luciferase in a series of intracellular tests wherein the effect of mTRAF1 and I-TRAF on NF-κB activity induced by Caspase 8, MRIT-α1 and DR3 in 293T cells was measured, as compared with a null vector control.

This series of experiments was conducted to determine whether mTRAF1 and I-TRAF could block Caspase 8-, MRIT-, and DR3-induced NF-κB activation. The procedures followed were identical to those of Example 5, using 100 ng/well of the first plasmid (i.e., control vector, Caspase 8, MRIT, and DR3) and 750 ng/well of the second plasmid (i.e., control vector, mTRAF1, and I-TRAF). The results are shown in FIG. 10 and demonstrate that both mTRAF1 and I-TRAF can block Caspase 8-induced NF-κB, but failed to effectively block MRIT-induced NF-κB. This example indicates that NF-κB-based functional screening assays can be utilized to identify lead compounds for pharmacological agents useful in the selective inhibition of Caspase 8-induced NF-κB pathway, while not interfering with MRIT-induced NF-κB signal transduction pathway.

EXAMPLE 8

The amino acid sequences of various DEDs-containing proteins were compared in order to identify residues which were highly conserved among the various proteins. The multiple sequence alignments of these DEDs-containing proteins are illustrated in FIG. 11. The conserved residues appear to play a functional role in the ability of DEDs-containing proteins to induce NF-κB. Knowledge of this sequence conservation can be used to develop pharmacological agents with altered properties to activate/inhibit the NF-κB pathway using the techniques of site-directed mutagenesis and/or structural-based drug design known in the art.

Figure 12:
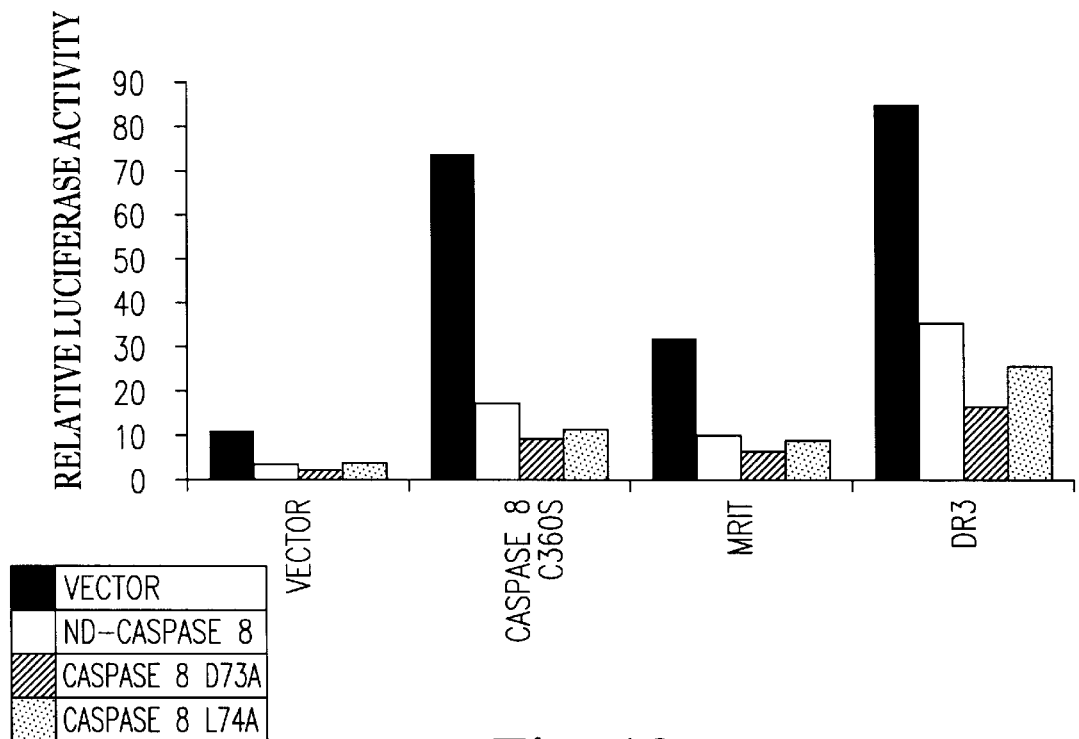
FIG. 12 is a graph similar to that of FIG. 8 illustrating the expression of luciferase in a series of intracellular tests wherein the effect of ND-Caspase 8, Caspase 8 D73A and Caspase 8 L74A on NF-κB activity induced by Caspase 8 mutant (C360S), MRIT-α1 and DR3 in 293 T cells was measured, as compared with a null vector control.

In order to prove this theory, various deletion and point mutants of the DEDs of Caspase 8 were tested for their ability to block Caspase 8 C360S-, MRIT- and DR3-induced NF-κB activation. The procedures followed were identical to those of Example 5, using 100 ng/well of the first plasmid (i.e., control vector, Caspase 8 C360S, MRIT, and DR3) and 750 ng/well of the second plasmid (i.e., control vector, ND-Caspase 8, Caspase 8 D73A, and Caspase 8 L74A). The results are shown in FIG. 12 and demonstrate that the various deletion and point mutants of Caspase 8 can block Caspase 8-, MRIT-, and DR3-induced NF-κB. This example illustrates that site-directed mutagenesis and structural-based drug design can be used to identify lead compounds for a pharmacological agent useful in the inhibition of Caspase 8-, MRIT-, and DR3-induced NF-κB pathway.

EXAMPLE 9

Figure 13:
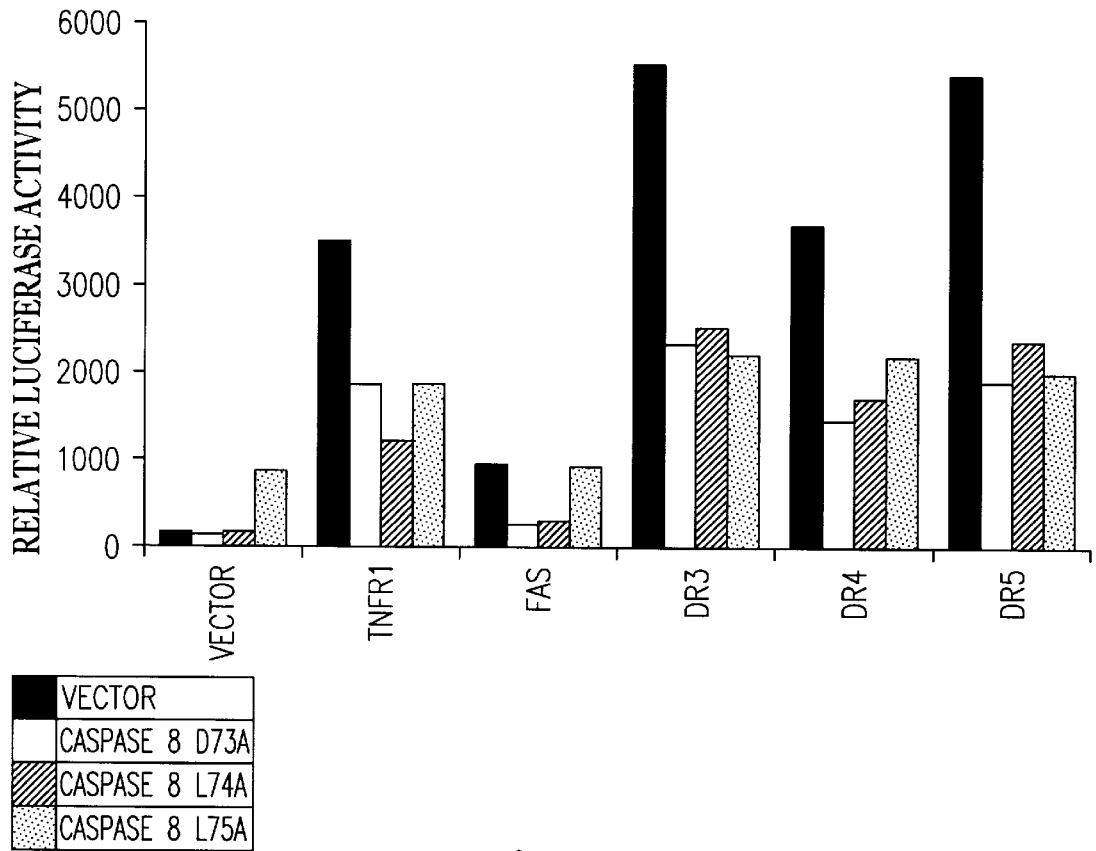
FIG. 13 is a graph similar to that of FIG. 8 illustrating the expression of luciferase in a series of intracellular tests wherein the effect of Caspase 8 D73A, Caspase 8 L74A and Caspase L75A on NF-κB activity mediated by TNFR1, Fas, DR3, DR4 and DR5 in 293T cells was measured, as compared with a null vector control.

This example illustrates that Caspase 8 plays a role in the activation of the NF-κB pathway mediated by various death receptors belonging to the TNF receptor family. The procedures followed were identical to those of Example 5 using 100 ng/well of the first plasmid (i.e., control vector, TNFR1, CD95/Fas, DR3, DR4, and DR5) and 750 ng/well of the second plasmid (i.e., control vector, Caspase 8 D73A, Caspase 8 L74A, and Caspase 8 L75A). The results are shown in FIG. 13. The mutants D73A and L74A were unable to activate NF-κB while the mutant L75A partially activated NF-κB. However, all of these mutants of DEDs of Caspase 8 blocked activation of the NF-κB pathway mediated by various death receptors belonging to the TNF receptor family. Therefore, these and similar mutants of the DEDs-containing proteins can serve as lead compounds for pharmacological agents useful in the treatment of diseases associated with dysfunctional NF-κB activation mediated by various death receptors of the TNFR family. Furthermore, this example illustrates that the structural features of DEDs may be exploited using the techniques of site-directed mutagenesis and structural-based drug design to identify lead compounds for pharmacological agents useful in the inhibition of death receptor-induced activation of the NF-κB pathway.

EXAMPLE 10

Figure 14:
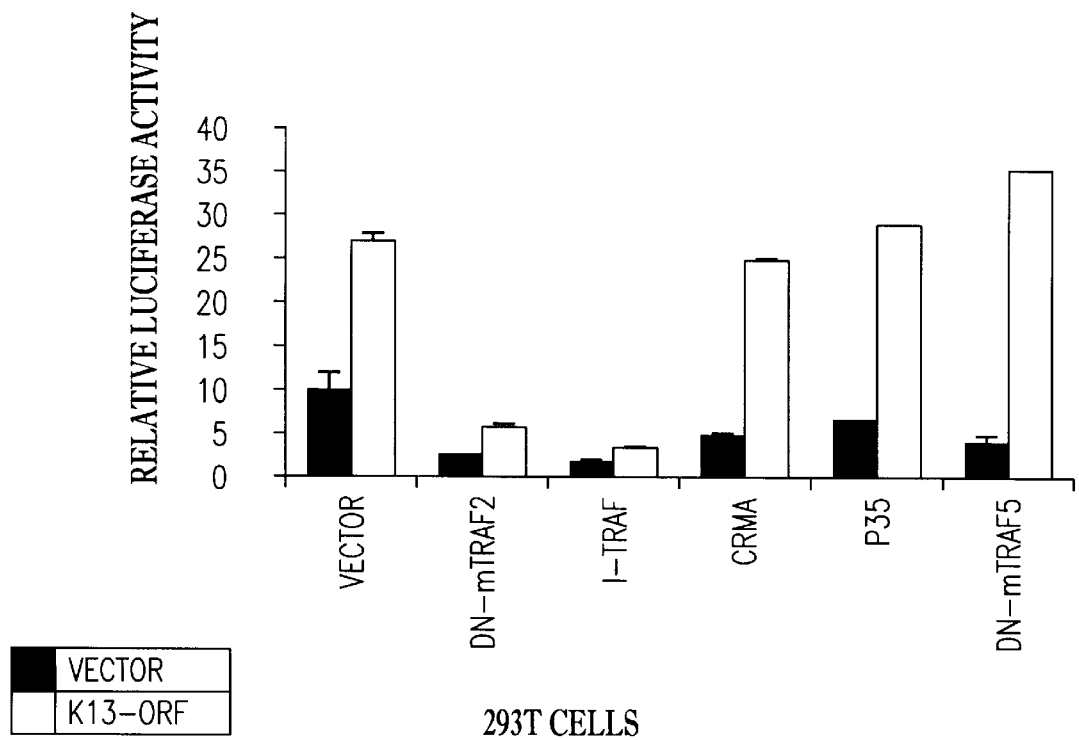
FIG. 14 is a graph similar to that of FIG. 8 illustrating the expression of luciferase in an intracellular test wherein the effect of DN-mTRAF2, I-TRAF, crmA, p35 and DN-mTRAF5 on NF-κB activity mediated by K13-ORF in 293T cells was measured, as compared with a null vector control.
Figure 15:
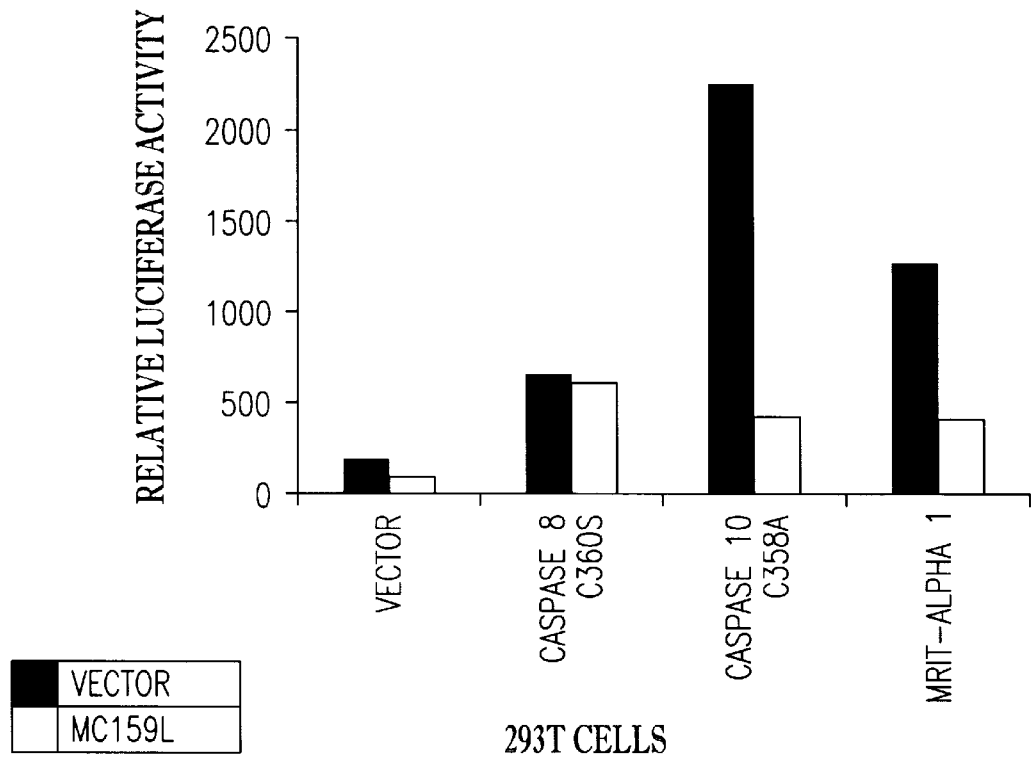
FIG. 15 is a graph similar to that of FIG. 8 illustrating the expression of luciferase in an intracellular test wherein the effect of MC159L on NF-κB activity mediated by Caspase 8 mutant (C360S), Caspase 10 mutant (C358A) and MRIT-α1 in 293T cells was measured, as compared with a null vector control.
Figure 16:
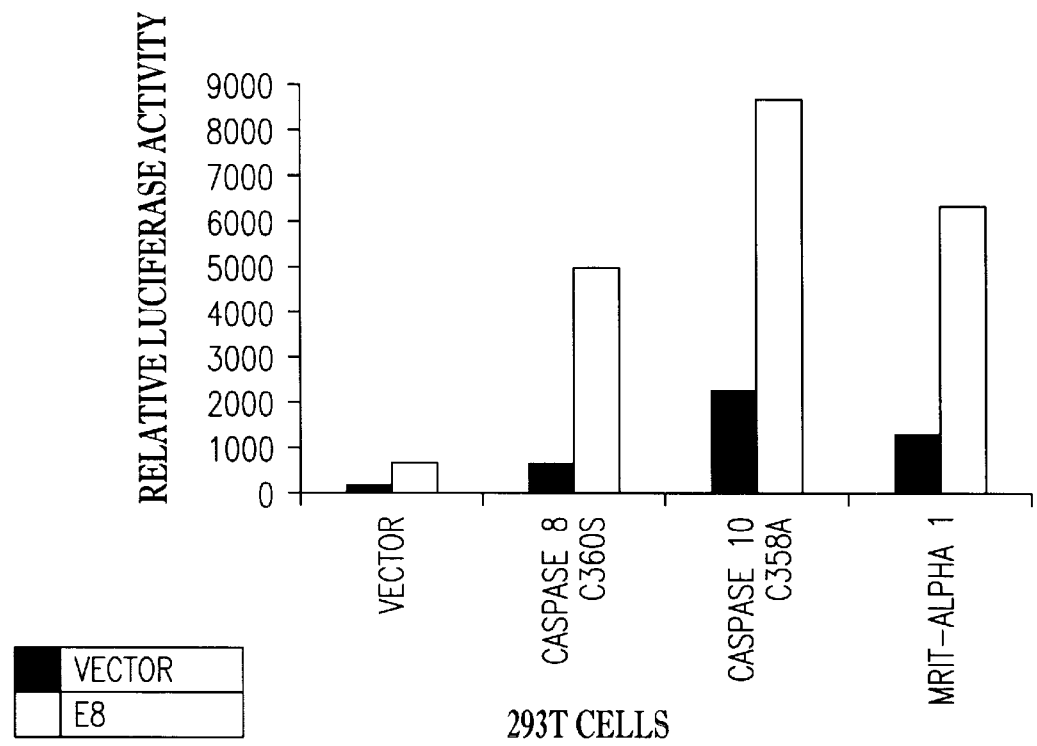
FIG. 16 is a graph similar to that of FIG. 8 illustrating the expression of luciferase in an intracellular test wherein the effect of E8 on NF-κB activity mediated by Caspase 8 mutant (C360S), Caspase 10 mutant (C358A) and MRIT-α1 in 293T cells was measured, as compared with a null vector control.
Figure 17:
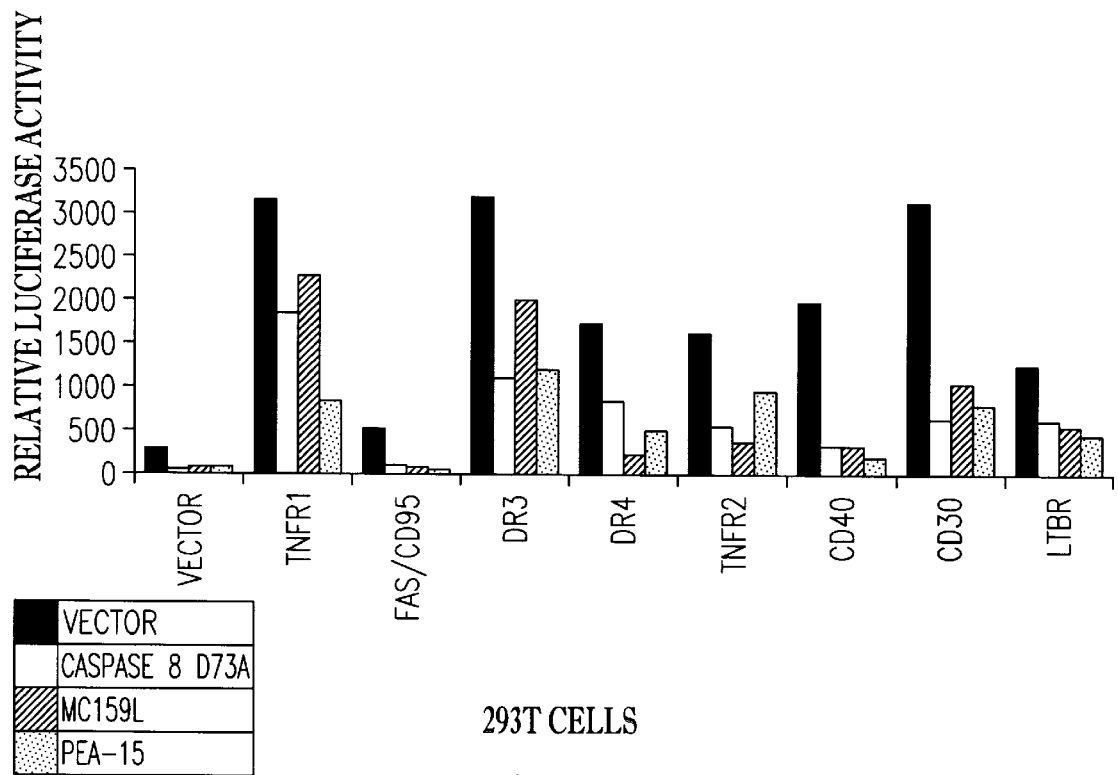
FIG. 17 is a graph similar to that of FIG. 8 illustrating the expression of luciferase in a series of intracellular tests wherein the effect of Caspase 8 mutant (D73A), MC159L and PEA-15 on NF-κB activity induced by TNFR1, Fas/CD95, DR3, DR4, TNFR2, CD40, CD30 and LTBR in 293T cells was measured, as compared with a null vector control.
Figure 18:
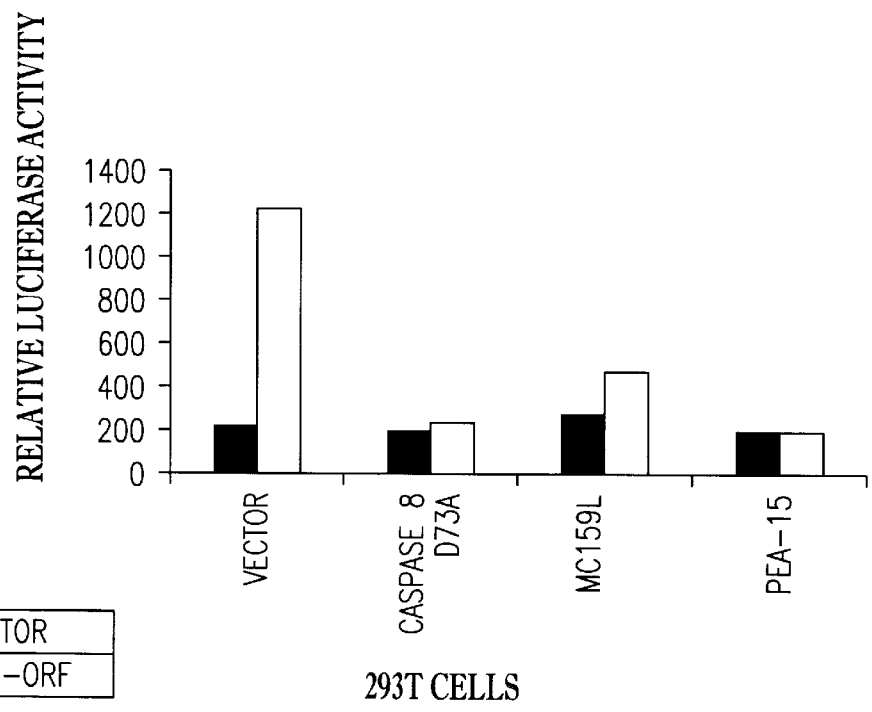
FIG. 18 is a graph similar to that of FIG. 8 illustrating the expression of luciferase in a series of intracellular tests wherein the effect of Caspase 8 mutant (D73A), MC159L and PEA-15 on NF-κB activity induced by K13-ORF in 293T cells was measured, as compared with a null vector control.
Figure 19:
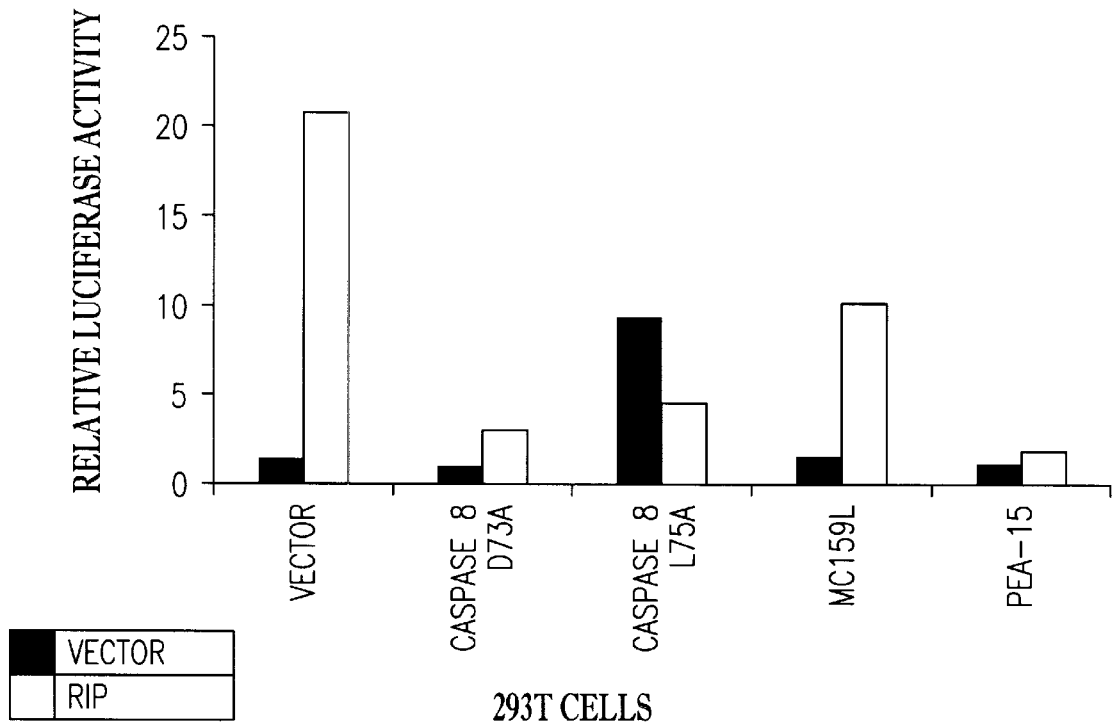
FIG. 19 is a graph similar to that of FIG. 8 illustrating the expression of luciferase in a series of intracellular tests wherein the effect of Caspase 8 mutant (D73A), Caspase 8 mutant (L75A), MC159L and PEA-15 on NF-κB activity induced by RIP in 293T cells was measured, as compared with a null vector control.
Figure 20:
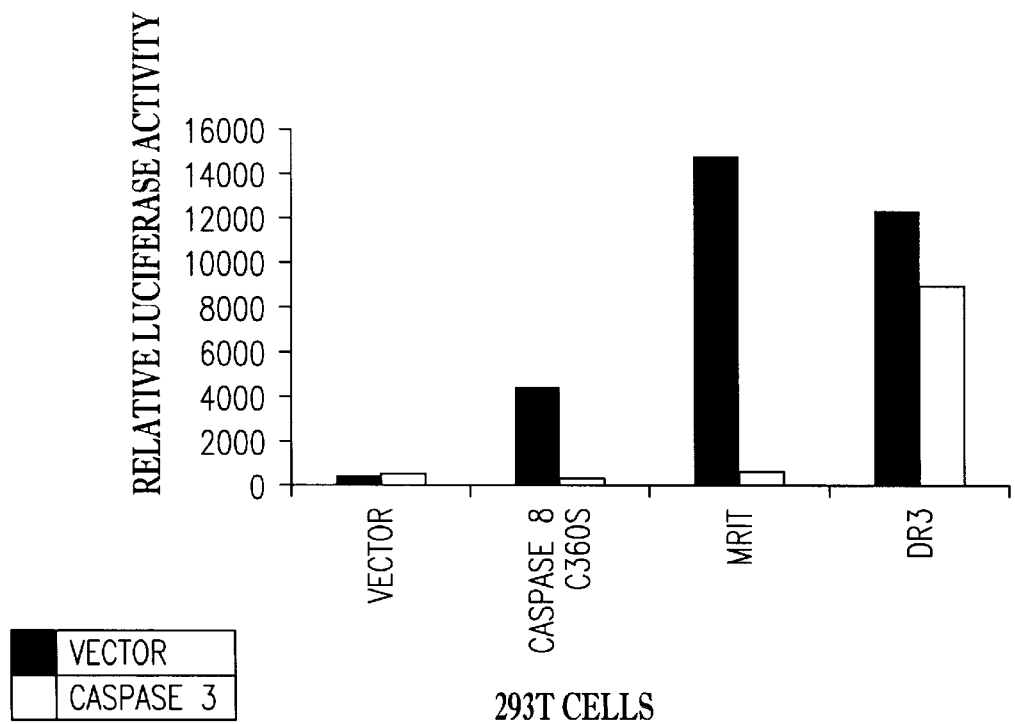
FIG. 20 is a graph similar to that of FIG. 8 illustrating the expression of luciferase in a series of intracellular tests wherein the effect of Caspase 3 on NF-κB activity induced by Caspase 8 mutant (C360S), MRIT-α1 and DR3 in 293T cells was measured, as compared with a null vector control.

This test was conducted to test the ability of K13-ORF (a protein encoded by the Kaposi Sarcoma Associated Herpes Virus) to activate the NF-κB pathway. The procedures followed were identical to those of Example 5 using 100 ng/well of the first plasmid (i.e., control vector and K13-ORF) and 750 ng/well of the second plasmid (i.e., control vector, DN-mTRAF2, I-TRAF, crmA, p35, and DN-TRAF 5). The results are set forth in FIG. 14 and illustrate that K13-ORF activates the NF-κB pathway. Furthermore, K13-ORF mediated NF-κB activation is inhibited by DN-mTRAF2 and I-TRAF, but not by crmA, p35, and DN-TRAF5. An NF-κB-based functional assay can thus be used as a screening tool for identifying lead compounds for a pharmacological agent capable of selectively blocking K13-ORF-induced NF-κB signal transduction pathway for use in the treatment of disease associated with the dysfunction/activation of this pathway.

EXAMPLE 11

Figure 21:
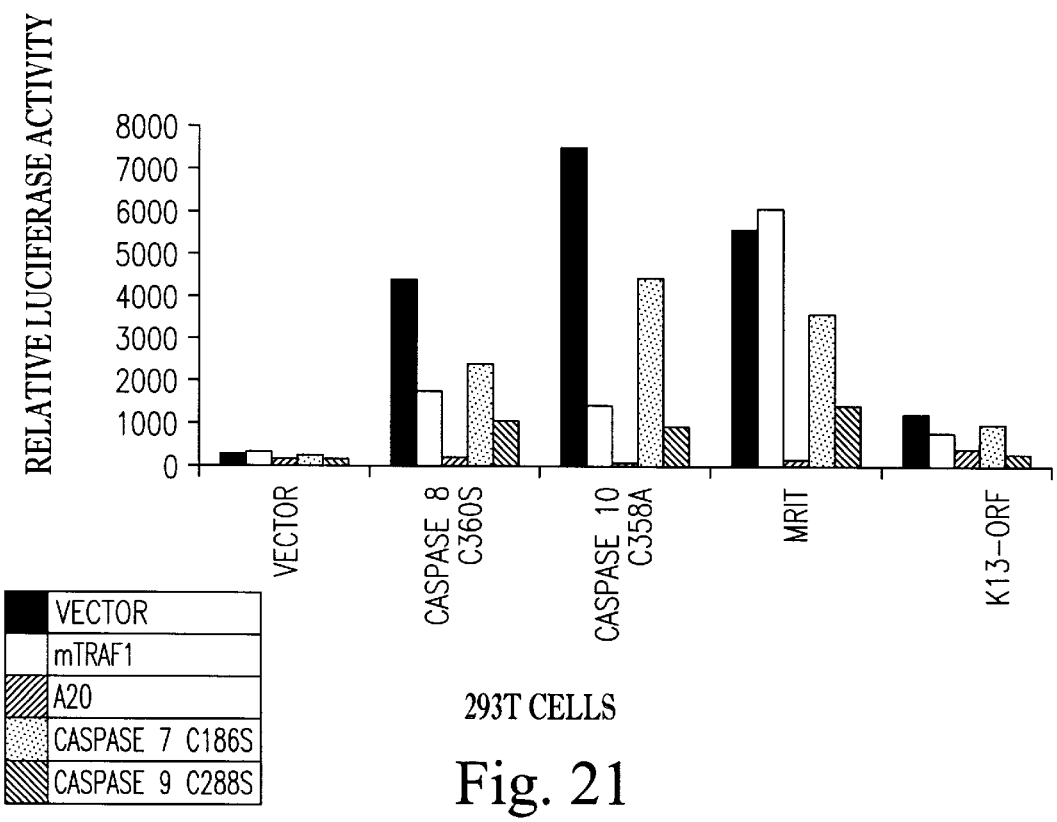
FIG. 21 is a graph similar to that of FIG. 8 illustrating the expression of luciferase in a series of intracellular tests wherein the effect of mTRAF1, A20, Caspase 7 mutant (C186S) and Caspase 9 mutant (C288S) on NF-κB activity induced by Caspase 8 mutant (C360S), Caspase 10 mutant (C358A), MRIT-α1 and K13-ORF in 293T cells was measured, as compared with a null vector control.

Tests were conducted to determine whether MC159L, a DEDs-containing protein encoded by Molluscum Contagiosum Virus, inhibits the NF-κB pathway. If it does inhibit the NF-κB pathway, MC159L may be responsible for the lack of inflammatory response in patients infected with this virus. The procedures followed were identical to those of Example 5, using 100 ng/well of the first plasmid (i.e., control vector, Caspase 8 C360S, Caspase 10 C358A, and MRIT) and 750 ng/well of the second plasmid (i.e., control vector and MC 159L). The results are shown in FIG. 15 and demonstrate that MC159L effectively blocks the Caspase 10 C358A- and MRIT-induced NF-κB pathway, but only minimally blocks the Caspase 8 C360S-induced NF-κB pathway. This example provides a mechanism by which MC159L can block the inflammatory response observed among patients infected with MCV. Based on these results, the inhibitors of MC159L mediated inhibition of the NF-κB pathway can be used as lead compounds for identifying pharmacological agents useful for the diagnosis and treatment of MCV infection. Such inhibitors can be readily identified using screening assays for NF-κB activation. Furthermore, based on these results, MC159L can be used as a lead compound for identifying pharmacological agents useful for the treatment of inflammatory disorders associated with the dysfunction of the NF-κB pathway.

EXAMPLE 12

These tests were conducted to determine whether E8, a DEDs-containing protein encoded by the Equine Herpes Virus 2, modulates NF-κB activation. The procedures followed were identical to those of Example 5, using 100 ng/well of the first plasmid (i.e., control vector, Caspase 8 C360S, Caspase 10 C358A, and MRIT) and 750 ng/well of the second plasmid (i.e., control vector and E8). The results, shown in FIG. 16, illustrate that by itself E8 only moderately activates NF-κB, but synergized Caspase 8 C360S-, Caspase 10 C358A-, and MRIT-induced NF-κB activation. Therefore, an NF-κB-based functional assay can be used as a screening tool for identifying lead compounds for a pharmacological agent capable of enhancing the NF-κB activating abilities of Caspase 8 C360S, Caspase 10 C358A, and MRIT. Based on the structure of the DEDs of E8, lead compounds for identifying pharmacological agents useful for modulating or enhancing NF-κB activation can also be identified.

EXAMPLE 13

These tests were conducted to test the hypothesis that DEDs-containing proteins can function as inhibitors of the NF-κB pathway activated by several members of the TNFR family. The procedures followed were identical to those of Example 5, using 100 ng/well of the first plasmid (i.e., control vector, TNFR1, Fas/CD95 (GenBank P25445), DR3, DR4, TNFR2, CD40, MTRAF5 and LTBR) and 750 ng/well of the second plasmid (i.e., control vector, Caspase 8 D73A, MC159L and PEA-15). The results are set forth in FIG. 17 and demonstrate that Caspase 8 D73A, MC159L and PEA-15 can block activation of NF-κB pathway induced by members of the TNFR family. Furthermore, these results show that there is a difference in the ability of MC159L to inhibit NF-κB activation mediated by the various members of the TNFR family. For example, MC159L is a good inhibitor of NF-κB activation mediated by Fas/CD95, DR4, TNFR2, CD40, MTRAF5 and lymphotoxin-β receptor but is a relatively poor inhibitor of NF-κB activation mediated by TNFR1 and DR3. The results demonstrate that the various DEDs-containing proteins may be used for selectively modulating activation of the NF-κB pathway mediated by the various members of the TNF receptor family. The various DEDs-containing proteins may also be used as lead compounds for developing pharmacological agents useful in selectively modulating activation of the NF-κB pathway mediated by the various members of the TNF receptor family.

EXAMPLE 14

This experiment was conducted to test the hypothesis that DEDs-containing proteins can function as an inhibitor of the NF-κB pathway activated by K13-ORF. The procedures followed were identical to those of Example 5, using 100 ng/well of the first plasmid (i.e., control vector, or K13-ORF) and 750 ng/well of the second plasmid (i.e., control vector, Caspase 8 D73A, MC159L and PEA-15). The results are given in FIG. 18 and indicate that Caspase 8 D73A, MC159L and PEA-15 can block activation of NF-κB pathway induced by K13-ORF. The various DEDs-containing proteins may be used as lead compounds for developing pharmacological agents useful in the diagnosis or treatment of disease associated with dysfunction of the NF-κB signal transduction pathway mediated by K13-ORF.

EXAMPLE 15

These tests were conducted to determine whether DEDs-containing proteins can function as an inhibitor of the NF-κB pathway activated by RIP. The procedures followed were identical to those of Example 5, using 100 ng/well of the first plasmid (i.e., control vector, or RIP) and 750 ng/well of the second plasmid (i.e., control vector, Caspase 8 D73A, Caspase 8 L75A, MC159L and PEA-15). The results are illustrated in FIG. 19. Caspase 8 D73A, Caspase 8 L75A, MC159L and PEA-15 can block activation of the NF-κB pathway induced by RIP. Thus, various DEDs-containing proteins may be used for modulating activation of the NF-κB pathway mediated by RIP. The various DEDs-containing proteins may also be used as lead compounds for developing pharmacological agents useful in modulating activation of NF-κB pathway mediated by RIP.

EXAMPLE 16

This experiment was conducted to test the hypothesis that Caspase 3 can function as an inhibitor of the NF-κB pathway activated by Caspase 8, MRIT and DR3. The procedures followed were identical to those of Example 5, using 100 ng/well of the first plasmid (i.e., control vector, Caspase 8 C360S, MRIT and DR3) and 750 ng/well of the second plasmid (i.e., control vector, Caspase 3). The results are shown in FIG. 20 and demonstrate that Caspase 3 can block activation of the NF-κB pathway induced by Caspase 8 C360S, MRIT and DR3. Thus, Caspase 3 may be used for selectively inhibiting activation of the NF-κB pathway mediated by Caspase 8, MIT, DR3, as well as NF-κB pathway induced by other TNFR family. Caspase 3 may also be used as a lead compound for developing pharmacological agents useful in inhibiting the activation of the NF-KB-KB pathway mediated by Caspase 8, MRIT and TNFR family members.

EXAMPLE 17

These tests were conducted to determine whether A20, mTRAF1, Caspase 7 C186S and Caspase 9 C288S can function as inhibitors of the NF-κB pathway activated by Caspase 8 C360S, Caspase 10 C358A, MRIT and K13-ORF. The procedures followed were identical to those of Example 5, using 100 ng/well of the first plasmid (i.e., control vector, Caspase 8 C360S, Caspase 10 C358A, MRIT and K13-ORF) and 750 ng/well of the second plasmid (i.e., control vector, A20, Caspase 7 C186S and Caspase 9 C288S). The results, shown in FIG. 21, indicate that A20, Caspase 7 C1 86S and Caspase 9 C288S blocks the NF-κB pathway mediated by Caspase 8 C360S, Caspase 10 C358A, MRIT and K13-ORF. Thus, A20, Caspase 7 C186S, and Caspase 9 C288S may be used for inhibiting activation of the NF-κB pathway mediated by Caspase 8, Caspase 10, MRIT and K13-ORF. Furthermore, A20, Caspase 7 C186S, and Caspase 9 C288S may serve as lead compounds for developing pharmacological agents useful in inhibiting activation of the NF-κB pathway mediated by Caspase 8, Caspase 10, MRIT and K13-ORF.

EXAMPLE 18

Figure 22:
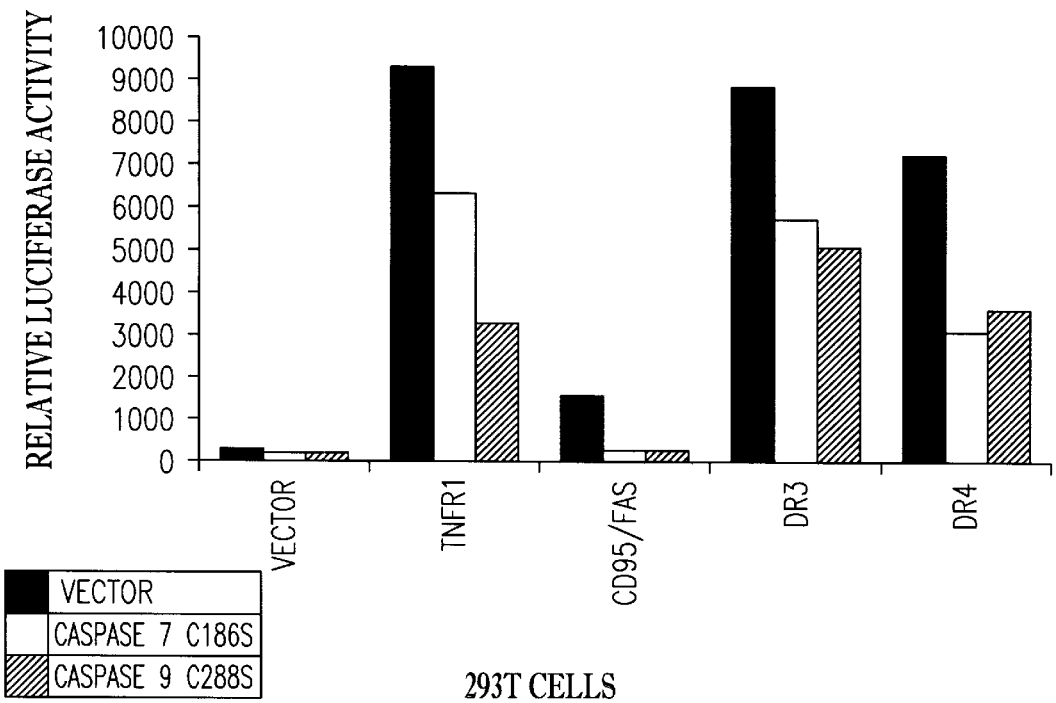
FIG. 22 is a graph similar to that of FIG. 8 illustrating the expression of luciferase in a series of intracellular tests wherein the effect of non DEDs-containing peptides Caspase 7 mutant (C186S) and Caspase 9 mutant (C288S) on NF-κB activity induced by TNFR1, Fas/CD95, DR3 and DR4 in 293T cells was measured, as compared with a null vector control.

This experiment was conducted to test whether non-DEDs-containing Caspases such as Caspase 7 C186S or Caspase 9 C288S can function as inhibitors of the NF-κB pathway activated by members of the TNFR family (i.e. TNFR1, Fas/CD95, DR3 and DR4). The procedures followed were identical to those of Example 5, using 100 ng/well of the first plasmid (i.e., control vector, TNFR1, Fas/CD95, DR3 and DR4) and 750 ng/well of the second plasmid (i.e., control vector, Caspase 7 C186S and Caspase 9 C288S). The results are set forth in FIG. 22 and demonstrate that Caspase 7 C186S and Caspase 9 C288S can block NF-κB pathway mediated by members of the TNFR family leading to the conclusion that other non-DEDs-containing Caspases may also be used to inhibit such TNFR-induced pathways. Furthermore, Caspase 7 C 186S, and Caspase 9 C288S may serve as lead compounds for developing pharmacological agents useful in inhibiting activation of NF-κB pathway mediated by the various members of the TNFR family.

EXAMPLE 19

Figure 23:
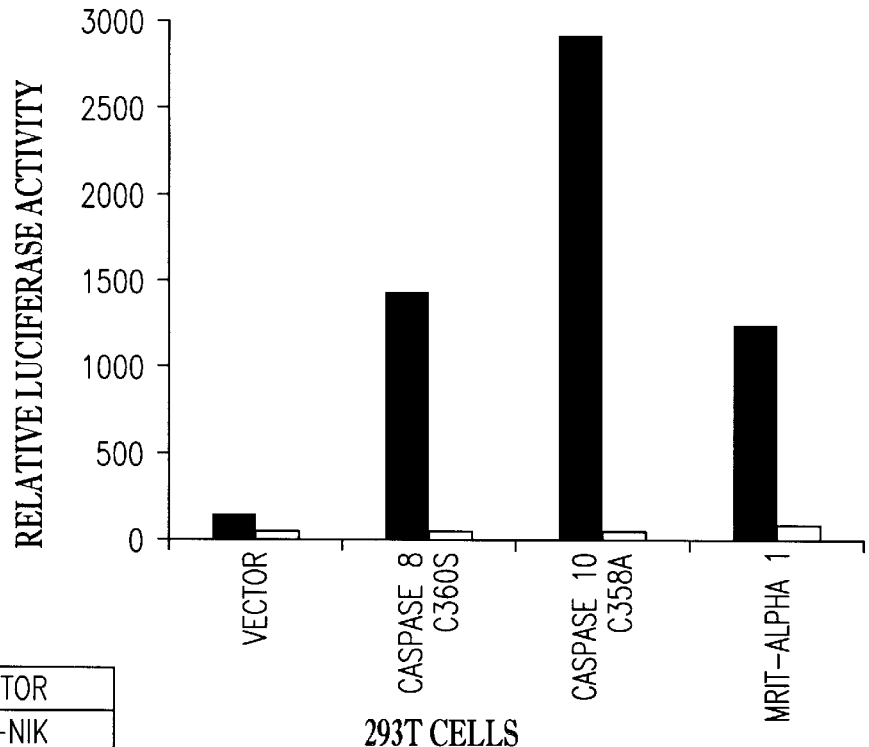
FIG. 23 is a graph similar to that of FIG. 8 illustrating the expression of luciferase in a series of intracellular tests wherein the effect of DN-NIK on NF-κB activity induced by Caspase 8 mutant (C360S), Caspase 10 mutant (C358A) and MRIT-α1 in 293T cells was measured, as compared with a null vector control.

These tests were conducted to determine whether a dominant negative mutant of NIK can function as an inhibitor of the NF-κB pathway activated by Caspase 8, Caspase 10 and MRIT. The procedures followed were identical to those of Example 5, using 100 ng/well of the first plasmid (i.e., control vector, Caspase 8 C360S, Caspase 10 C358A and MRIT) and 750 ng/well of the second plasmid (i.e., control vector, DN-NIK). The results, set forth in FIG. 23, demonstrate that DN-NIK can block activation of the NF-κB pathway induced by Caspase 8 C360S, Caspase 10 C358A and MRIT. Thus, DN-NIK may be used for inhibiting activation of the NF-κB pathway mediated by Caspase 8, Caspase 10 and MRIT. DN-NIK may also be used a lead compound for developing pharmacological agents useful in inhibiting activation of NF-κB pathway mediated by Caspase 8, Caspase 10 and MRIT.

EXAMPLE 20

In this experiment, the ability of various Caspases and of MRIT to activate the JNK pathway is demonstrated. The luciferase based assay for measuring the activation of the JNK pathway was conducted using the c-Jun PathDetect™ Reporting System (Stratagene, La Jolla, Calif., catalog no. 219000). Briefly, 293EBNA cells (1×10$^5$) (Invitrogen) were transfected with 750 ng/well of a test plasmid (i.e., control vector, Caspase 8 C360S, Caspase 10 C358A, MRIT, Caspase 8 PRO (a.a. 1-180), Caspase 10 PRO (a.a. 1-191), MRIT-β1, CD40) along with pFA-Jun (50 ng) pFR-Luc (500 ng), and a pRcRSV/lacZ plasmid in duplicate in each well of a 24 well tissue culture plate using the calcium phosphate co-precipitation method described in Example 1. Luciferase and β-galactosidase activities were measured from cell extracts between 24–40 hours after transfection as described above for NF-κB assay. β-galactosidase activity was used to normalize the luciferase activity to control for variations in the transfection efficiency.

Figure 24:
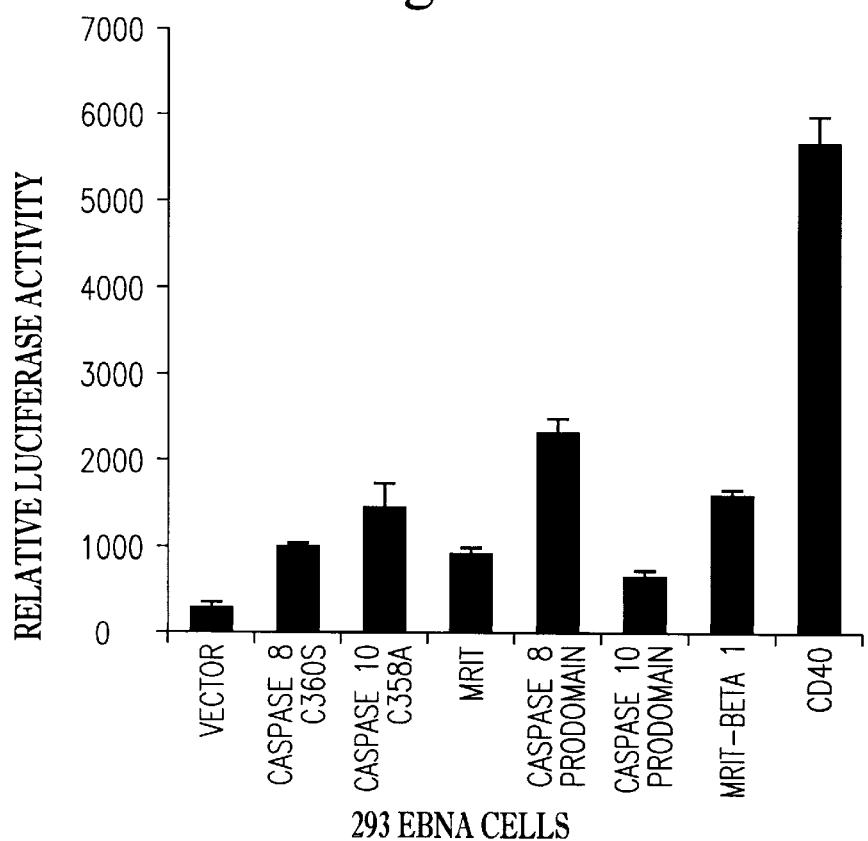
FIG. 24 is a graph illustrating the expression of luciferase in a series of intracellular tests wherein the effect of Caspase 8 mutant (C360S), Caspase 10 mutant (C358A), MRIT-α1, Caspase 8 prodomain, Caspase 10 prodomain, MRIT-β1 and CD40 on JNK pathway activation in 293EBNA cells was measured, as compared with a null vector control.

The results of this experiments are set forth in FIG. 24 and demonstrate that Caspase 8, Caspase 10, and MRIT can activate the JNK pathway and that this activity is localized to their respective pro-domains consisting of the two DEDs.

EXAMPLE 21

In this experiment the ability of various Caspases and MRIT to activate the JNK pathway was demonstrated using a JNK activation assay based on the phosphorylation of c-jun. 293 EBNA cells (2×10$^6$ cells) were transfected with 5 μg of each of the test plasmid (i.e., control vector, Caspase 8 C360S, Caspase 10 C358A, MRIT, and CD40) and a reporter plasmid encoding HA-tagged Green Fluorescent protein (GFP-HA). Thirty-six hour post-transfection the cells were lysed and an assay for phosphorylated c-jun was performed using the Non-radioactive SAPK/JNK Assay Kit (New England BioLabs, catalog no. 9810) and following the manufacturer's instructions.

Figure 25:
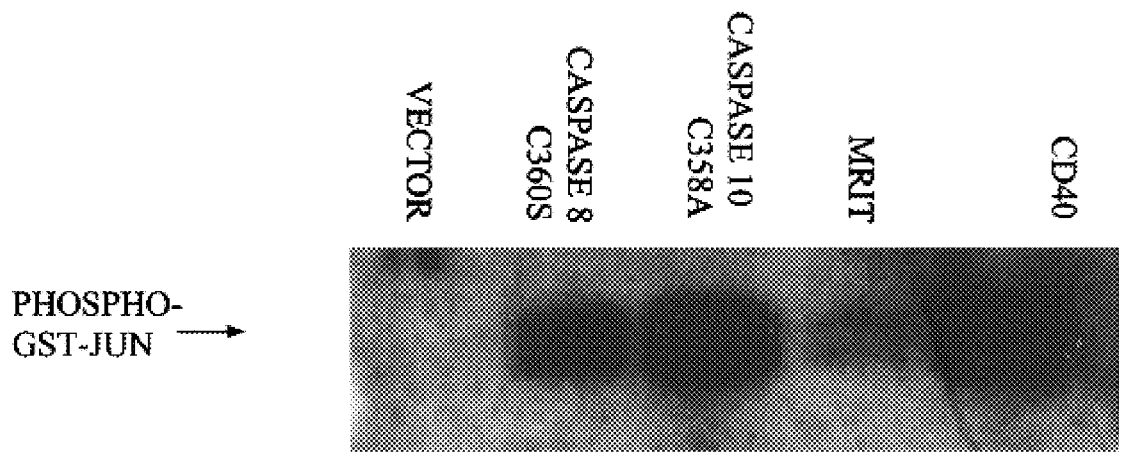
FIG. 25 is a photograph illustrating a JNK activation assay based upon c-jun phosphorylation wherein the effect of expression of Caspase 8 mutant (C3 60S), Caspase 10 mutant (C358A), MRIT-A 1 and CD40 was determined as compared with a null vector control.

The results of these experiments are set forth in FIG. 25. Caspase 8, Caspase 10, and MRIT activate the JNK pathway. This activity is independent of the protease activity of Caspases 8 and 10. This example illustrates that the above assay, as well as similar JNK activation-based functional assays known to one skilled in the art, can be used as a screening tool for identifying lead compounds for pharmacological agents capable of selectively modulating Caspase 8-, Caspase 10-, and/or MRIT-induced JNK signal transduction pathway.

EXAMPLE 22

These tests were conducted to determine whether various agents were capable of modulating Caspase 8-, Caspase 10-, and MRIT-induced activation of the JNK pathway. The procedure followed was as described in Example 20 except that 750 ng/well of the second plasmid (i.e., control vector, DN-mTRAF2, I-TRAF, Caspase 8 D73A, and Caspase 8 L75A) was used along with 100 ng/well of the test plasmid (i.e., control vector, Caspase 8 C360S, Caspase 10 C358A, and MRIT).

Figure 26:
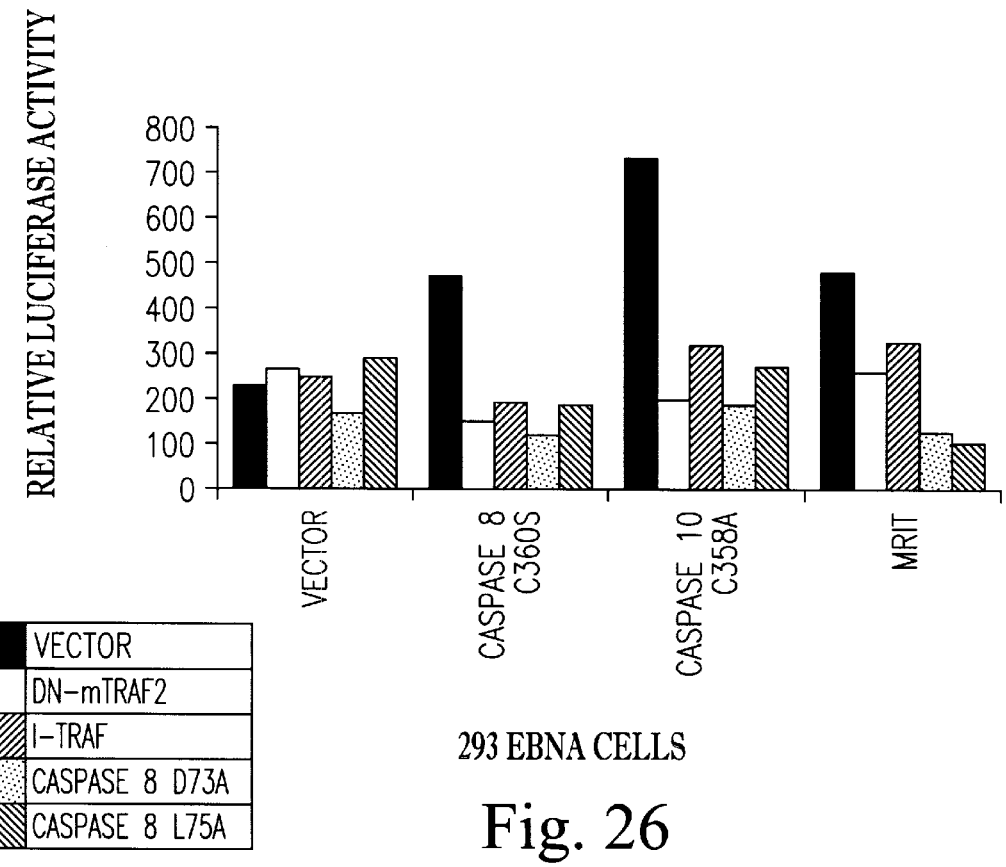
FIG. 26 is a graph similar to that of FIG. 8 illustrating the expression of luciferase in a series of intracellular tests wherein the effect of DN-mTRAF2, I-TRAF, Caspase 8 mutant (D73A) and Caspase 8 mutant (L75A) on JNK activity induced by Caspase 8 mutant (C360S), Caspase 10 mutant (C358A) and MRIT-α1 in 293EBNA cells was measured, as compared with a null vector control.

The results of this experiment are set forth in FIG. 26 and demonstrate that DN-mTRAF2, I-TRAF, Caspase 8 D73A, and Caspase 8 L75A can block Caspase 8-, Caspase 10-, and MRIT-induced activation of the JNK pathway. This example indicates that a JNK activation-based functional assay can be used as a screening tool for identifying lead compounds for pharmacological agents capable of blocking Caspase 8-, 10-, and/or MRIT-induced JNK signal transduction pathway.

EXAMPLE 23

The purpose of this experiment was to determine the ability of a Caspase 8 mutant (Caspase 8 D73A) to inhibit TNF receptors-induced activation of the JNK pathway. The procedure followed was as described in Example 20 except that 750 ng/well of the second plasmid (i.e., control vector and Caspase 8 D73A) was used along with 100 ng/well of the test plasmid (i.e., control vector, TNFR1, CD95/FAS, DR3, DR4, and CD40). The results of this experiment are set forth in FIG. 27. Caspase 8 D73A can block TNF receptors-induced activation of the JNK pathway. This example shows that a JNK activation-based functional assay can be used as a screening tool for identifying lead compounds for a pharmacological agent capable of selectively blocking TNF receptors-induced JNK signal transduction pathway. Furthermore, this example illustrates that the structural features of DEDs-containing proteins may be exploited using the techniques of site directed mutagenesis and structural-based drug design to identify lead compounds for a pharmacological agent useful in the inhibition of TNF receptors-induced activation of the JNK pathway.

EXAMPLE 24

These experiments were conducted to determine whether Caspase 8 can interact with TRAF1 and TRAF2 proteins using the following co-expression-immunoprecipitation assay.

For studying in vivo interaction, $2 \times 10^6$ 293T cells were plated in a 100 mm plate. Eighteen to 24 hours later, the cells were co-transfected with 5 µg/plate of each of the first epitope-tagged constructs (i.e., control vector and myc-Caspase 8) along with 5 µg/plate of either HA-epitope tagged mTRAF1 or FLAG-epitope tagged mTRAF2, in combination with 1 µg of a Green Fluorescent Protein (GFP) encoding plasmid (pEGFP-C1) (Clontech). The co-transfection was achieved by the calcium phosphate co-precipitation method which comprises a 2× HEPES solution (8 g NaCl, 1.5 mM $Na_2HPO_4$, 6.5 g HEPES, an amount of $H_2O$ to bring the total solution volume to 500 ml, pH of 7.0, stored at 4° C.) and 2M $CaCl_2$ stored in aliquots at −20° C. Sixty-one µl of 2M $CaCl_2$ solution was mixed with the desired DNA construct solutions (dissolved in a buffer containing 10 mM Tris and 1 mM EDTA) and water in an amount to bring the total volume of the complete solution to 500 µl. To this solution, 500 µl of the 2× HEPES solution was added dropwise with shaking and the resulting precipitate was sprinkled over the cells in each tissue culture plate (Falcon). Eighteen to 36 hours post-transfection, the cells were examined under a fluorescent microscope to ensure equal transfection efficiency as determined by the expression of the GFP. Eighteen to 36 hours post-transfection cells were lysed in 1 ml of a lysis buffer containing 0.1% Triton-X 100, 20 mM sodium phosphate (pH 7.4), 150 mM NaCl and 1 EDTA free protease inhibitor tablet per 10 ml (Boehringer Mannheim). For immunoprecipitation, the cell lysate (500 µl) was incubated for 1 hour at 4° C. with 10 µl of myc beads or control beads precoated with 2% BSA. The beads were washed twice with lysis buffer, twice with a wash buffer (0.1% Triton-X 100, 20 mM sodium phosphate (pH 7.4), 500 mM NaCl), and again with lysis buffer. Bound proteins were eluted by boiling for 3 minutes in SDS-loading buffer, separated by SDS-PAGE, and transferred to a nitrocellulose membrane followed by a western blot analysis. For the western blot analysis, the nitrocellulose membrane was pre-blocked with 5% casein in TBS with 0.05% Tween 20. Coimmunoprecipitating TRAF1 and TRAF2 proteins were detected by western blot analysis using rabbit polyclonal antibodies against the HA or the FLAG™ epitope tags respectively. Horse-radish-peroxidase conjugated donkey anti-rabbit secondary antibody was obtained from Pierce (Catalog #31458). Incubation with primary and secondary antibodies was carried out in 2% casein. Between each incubation, the membrane was washed three to four times with TBS containing 0.05% Tween. The blot was developed using the Supersignal ULTRA (Pierce) Chemiluminescent Detection System following the manufacturer's instructions.

Figure 28:
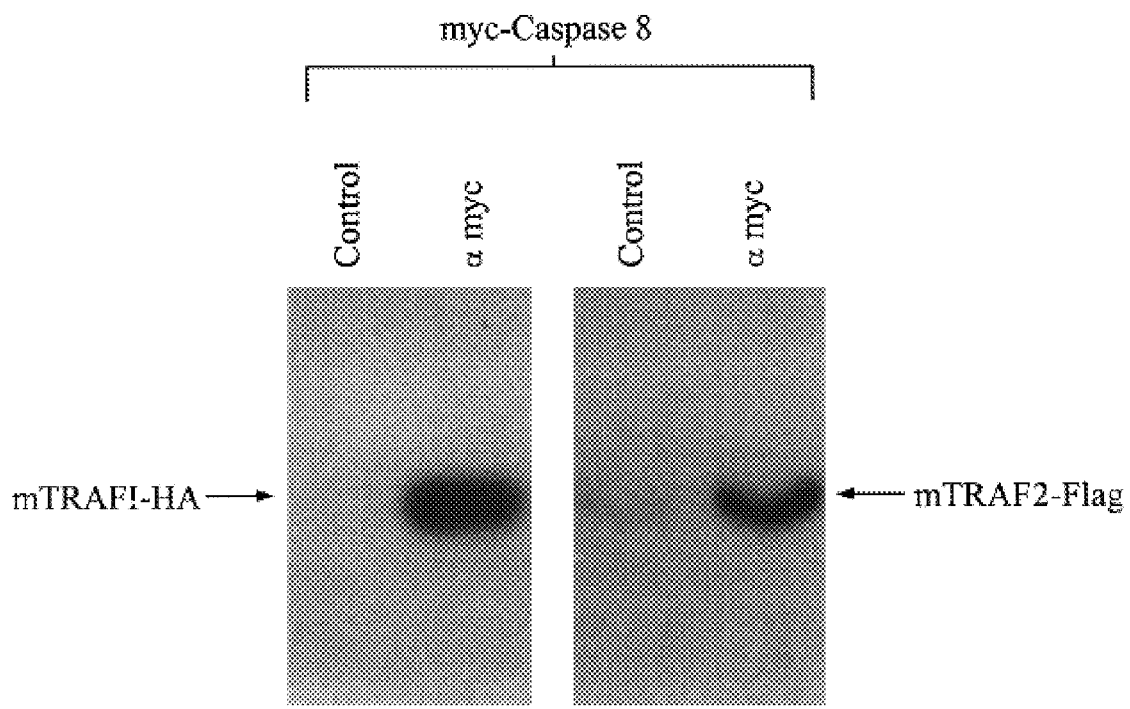
FIG. 28 is a pair of photographs depicting the results of a co-expression-immunoprecipitation assay wherein the interaction between Caspase 8 and mTRAF 1-HA, and between Caspase 8 and mTRAF2-FLAG, were measured in 293T cells as compared with a control.

The results of these experiments are given in FIG. 28. Caspase 8 directly interacts with both TRAF1 and TRAF 2 proteins when co-expressed with TRAF1 or TRAF2 in mammalian cells. This example demonstrates that an assay based on interaction between Caspase 8 and TRAF1 or TRAF2 can be used as a screening tool for identifying lead compounds for pharmacological agents capable of selectively blocking Caspase 8 and TRAF1 or TRAF2 interaction for the purpose of blocking Caspase 8-TRAFs signal transduction pathway.

EXAMPLE 25

This experiment was conducted to determine whether Caspase 8 interacts with the TRAF3 protein. The co-expression-immunoprecipitation assay was similar to that described in Example 24 except the first expression vector consisted of FLAG-tagged Caspase 8 C360S and the second expression vector consisted of HA-tagged TRAF3. FLAG-tagged proteins were immunoprecipitated using the FLAG beads or control beads, and co-immunoprecipitating HA-TRAF3 was detected by western blot analysis using a rabbit polyclonal antibody against the HA tag.

Figure 29:
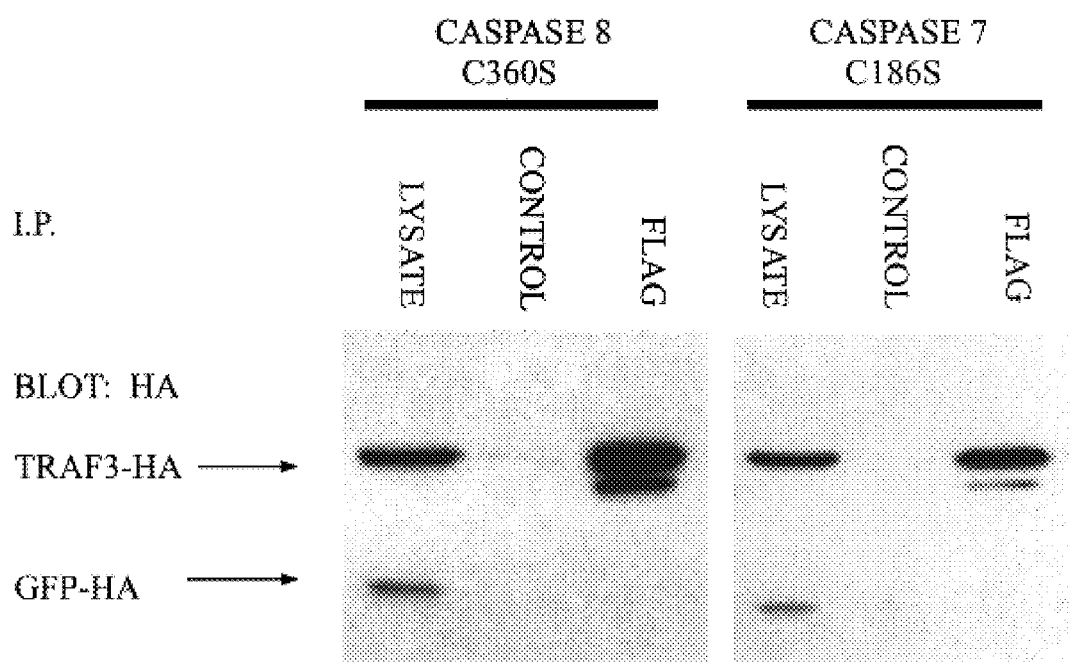
FIG. 29 is a pair of photographs depicting the results of a co-expression-immunoprecipitation assay wherein the interactions between Caspase 8 mutant (C360S) and TRAF3-HA/GFP-HA, and between Caspase 7 mutant (C186S) and TRAF3-HA/GFP-HA, were measured in 293T cells as compared with a control, wherein the lysate lane shows the expression of the HA-tagged proteins in the total cellular extract.

The results of this experiment are shown in FIG. 29 and indicate that Caspase 8 directly interacts with the TRAF3 protein when they are co-expressed in mammalian cells. Caspase 8 did not interact with GFP-HA, thereby confirming the specificity of its interaction with TRAF3. This example also illustrates that an assay based on the interaction between Caspase 8 and TRAF3 can be used as a screening tool for identifying lead compounds for pharmacological agents capable of selectively blocking Caspase 8 and TRAF3 interaction for the purpose of blocking Caspase 8-TRAF3 signal transduction pathway.

EXAMPLE 26

The purpose of these tests was to determine whether Caspase 8 interacts with the TRAF5 protein. The co-expression-immunoprecipitation assay was similar to that described in Example 24 except the first expression vector consisted of myc-tagged Caspase 8 C360S and the second expression vector consisted of FLAG-tagged TRAF5 or FLAG-tagged DN-TRAF5. FLAG-tagged proteins were immunoprecipitated using FLAG beads or control beads. Co-immunoprecipitating myc-tagged Caspase 8 was detected by western blot analysis using a rabbit polyclonal antibody against the myc tag.

Figure 30:
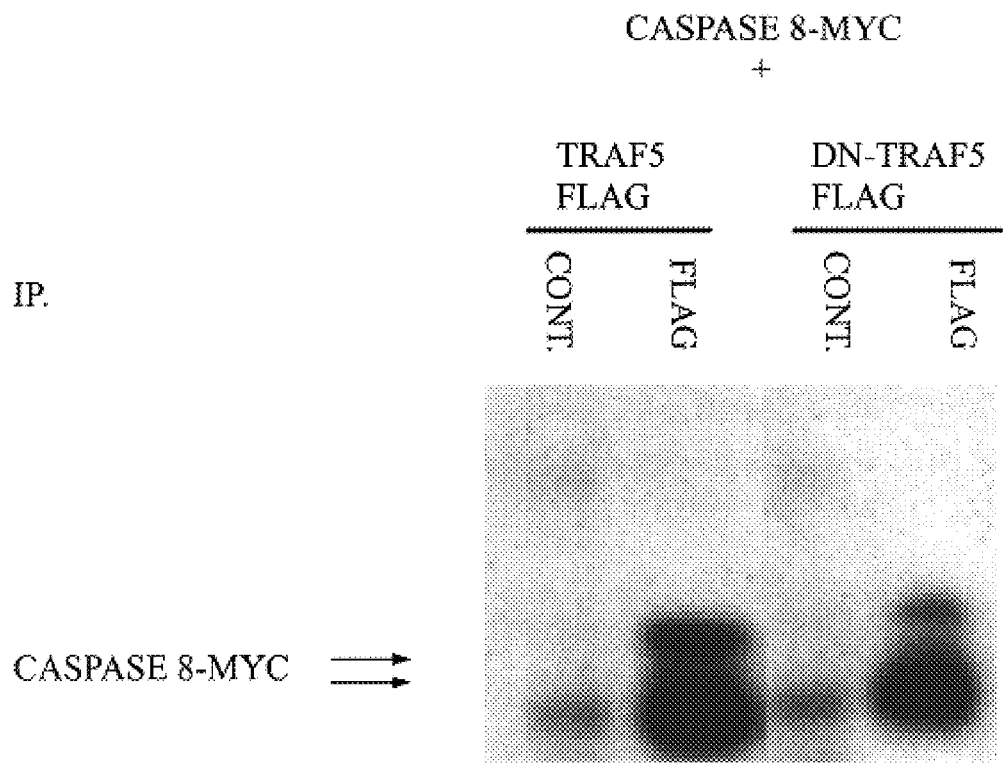
FIG. 30 is a pair of photographs depicting the results of a co-expression-immunoprecipitation assay wherein the interaction between Caspase 8 and TRAF5 FLAG, and between Caspase 8 and DN-TRAF5 FLAG, were measured in 293T cells as compared with a control.

The results of this experiment are set forth in FIG. 30. Caspase 8 directly interacts with TRAF5 and DN-TRAF5 proteins when co-expressed with TRAF5 or DN-TRAF5 proteins in mammalian cells. This example shows that an assay based on interaction between Caspase 8 and TRAF5 or DN-TRAF5 can be used as a screening tool for identifying lead compounds for pharmacological agents capable of selectively blocking Caspase 8 and TRAF5 interaction for the purpose of blocking Caspase 8-TRAF5 signal transduction pathway.

EXAMPLE 27

This experiment was conducted to determine which domains of Caspase 8 and MRIT interact with the TRAF1 protein. The procedure was similar to the co-expression-immunoprecipitation assay described in Example 24 except the first expression vector consisted of FLAG-tagged protease domain of Caspase 8 (a.a. 217-479), FLAG-tagged Caspase 8 prodomain (a.a. 1-180), or MRIT-β1 (a.a. 1-221), and the second expression vector consisted of HA-tagged mTRAF1. FLAG-tagged proteins were immunoprecipitated using FLAG beads or control beads. Co-immunoprecipitating HA-TRAF1 was detected by Western Blot analysis using a rabbit polyclonal antibody against the HA tag.

Figure 31:
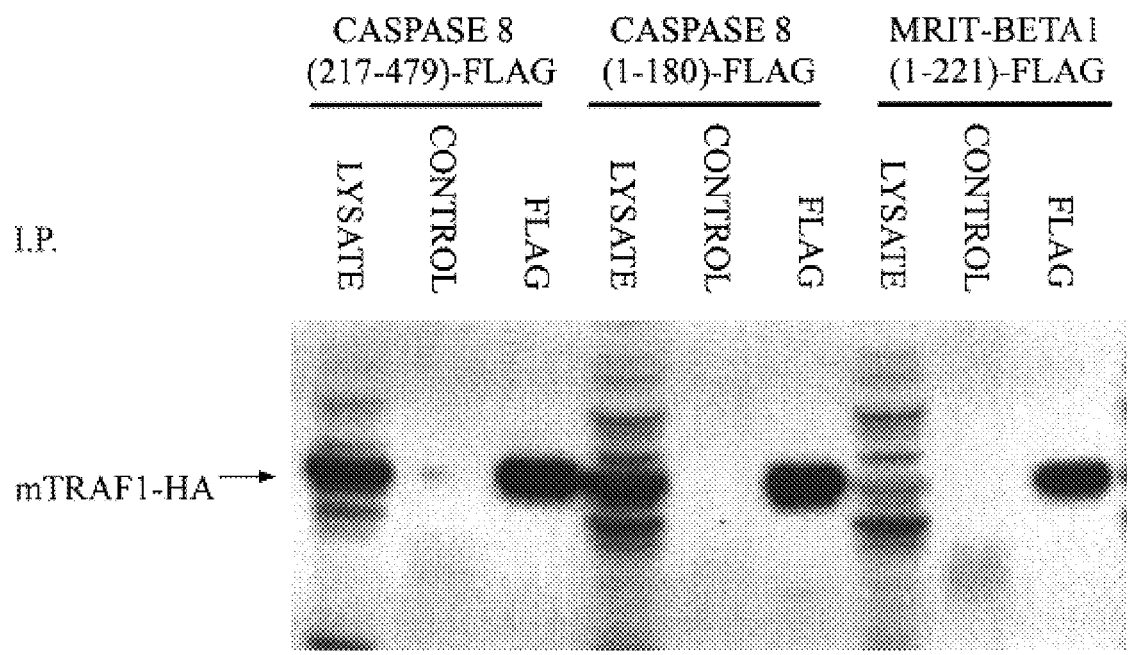
FIG. 31 is a series of three photographs depicting the results of a co-expression-immunoprecipitation assay wherein the interaction between Caspase 8 protease domain FLAG (a.a. 217-479) and mTRAF1-HA, between Caspase 8 prodomain FLAG (a.a. 1 -180), and between MRIT-β1 FLAG (a.a. 1-221), was measured in 293T cells as compared with a control, wherein the lysate lane shows the expression of the HA-tagged proteins in the total cellular extract.
Figure 32:
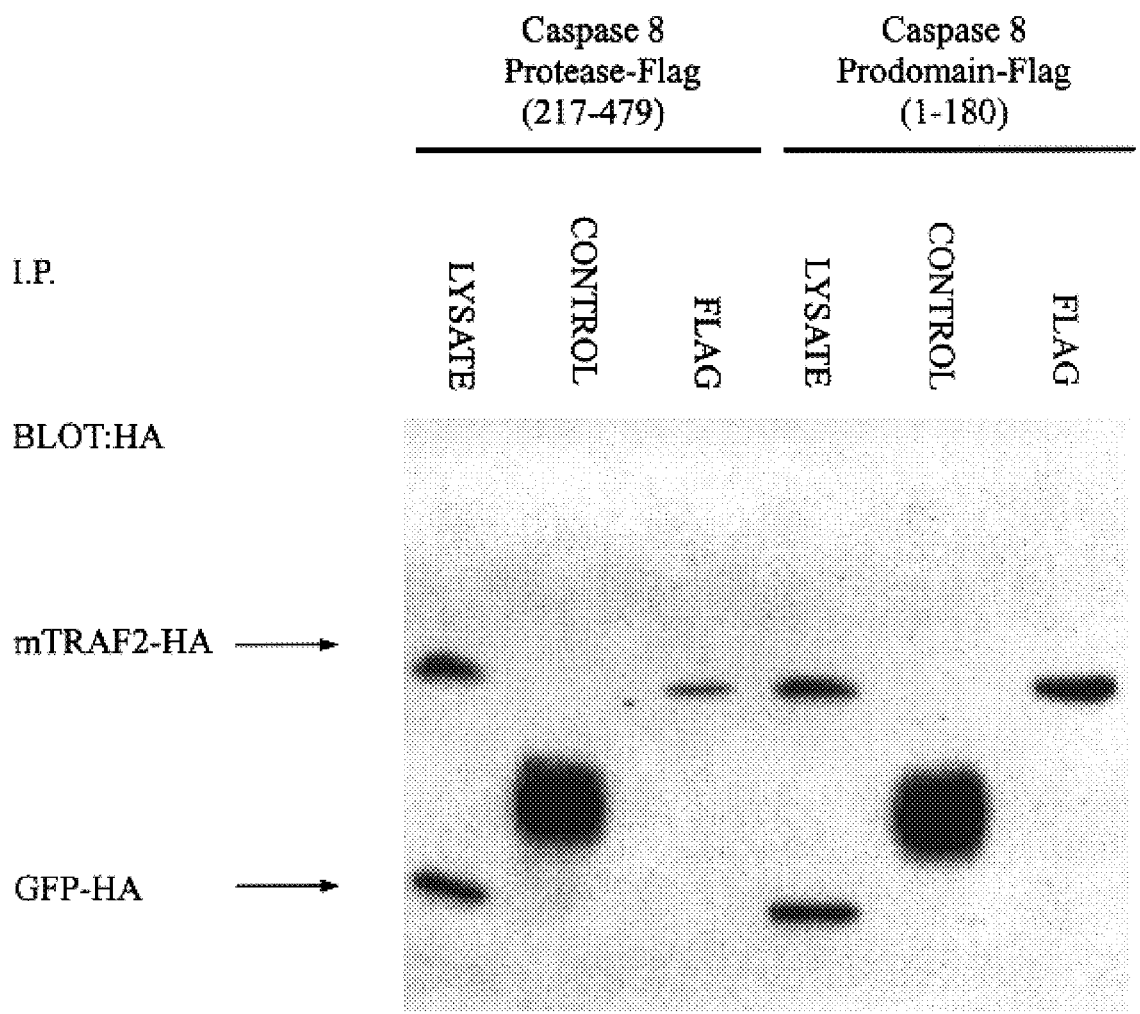
FIG. 32 is a pair of photographs depicting the results of a co-expression-immunoprecipitation assay wherein the interaction between Caspase 8 protease FLAG (a.a. 217-479) and mTRAF2-HA/GFP-HA, and between Caspase 8 prodomain FLAG (a.a. 1- 180) and mTRAF2-HA/GFP-HA, was measured in 293T cells as compared with a control.

The results of this experiment are illustrated in FIG. 31 and show that the Caspase 8 protease domain, Caspase 8 prodomain, and MRIT-β1 isoform (containing its prodomain) directly interact with the TRAF1 protein when co-expressed with it in mammalian cells. Essentially similar results were obtained using mTRAF2 protein instead of mTRAF1 (see FIG. 29). Thus, an assay based on interaction between the Caspase 8 protease domain, the Caspase 8 prodomain, and the MRIT-β1 isoform, and the TRAF family of proteins can be used as a screening tool for identifying lead compounds for pharmacological agents capable of selectively blocking the interactions between the Caspase 8 protease domain, Caspase 8 prodomain, and MRIT-β1 isoform, and TRAF proteins for the purpose of blocking Caspase 8-TRAF and MRIT-TRAF signal transduction pathway.

EXAMPLE 28

Figure 33:
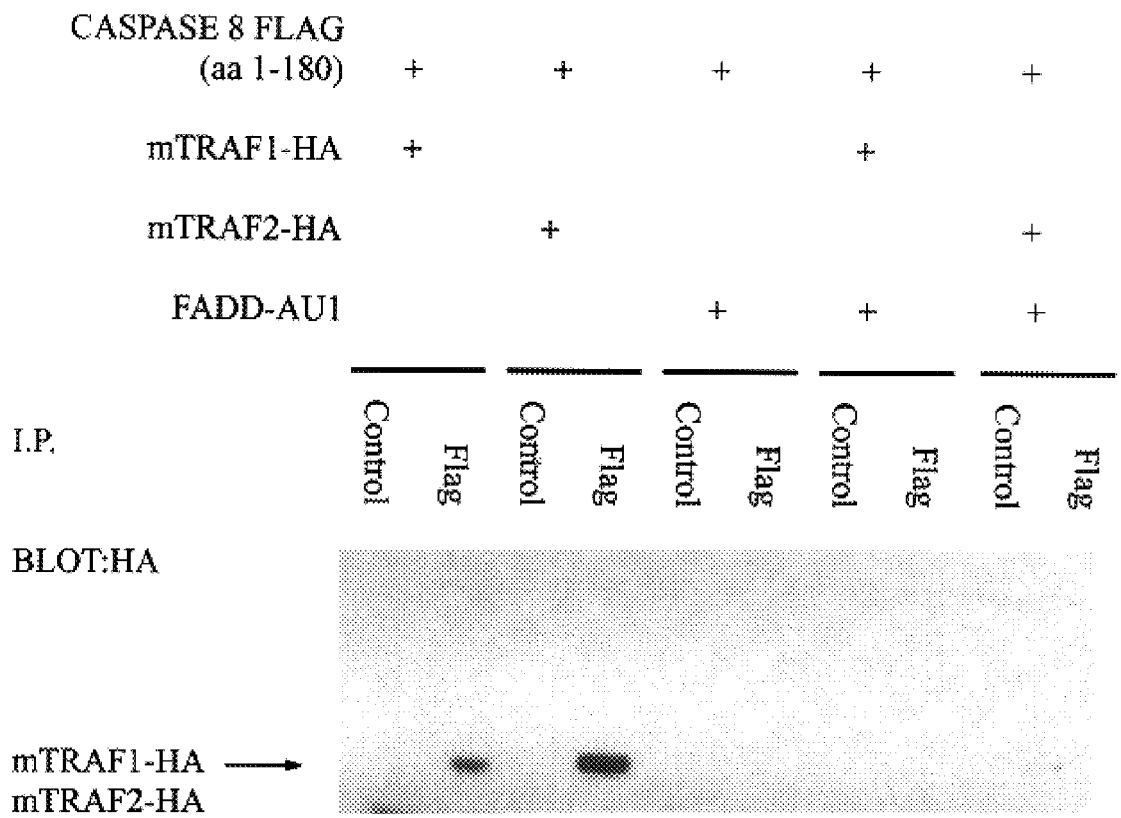
FIG. 33 is a series of photographs depicting the results of a co-expression-immunoprecipitation assay wherein the interaction between Caspase 8 FLAG (a.a. 1-180) and mTRAF1-HA, mTRAF2-HA and FADD-AU1, was measured in 293T cells as compared with a control.

This experiment was conducted to determine whether FADD can influence the interaction between the Caspase 8 prodomain and TRAF proteins. The procedure was similar to that described in Example 24 except the co-transfection was performed using expression vectors encoding FLAG-tagged Caspase 8 prodomain (a.a. 1- 180) and either HA-tagged mTRAF1 or HA-tagged mTRAF2 in the absence or presence of AU1-tagged FADD as shown in FIG. 33. FLAG-tagged proteins were immunoprecipitated using FLAG beads or control beads, and co-immunoprecipitating HA-mTRAF1/mTRAF2 were detected by western blot analysis using a rabbit polyclonal antibody against the HA tag.

The results of this experiment demonstrate that co-expression of FADD leads to a significant decrease in the amount co-precipitating mTRAF1 or mTRAF2. Therefore, an assay based on the interaction between the Caspase 8 prodomain and TRAFs can be used as a screening tool for identifying lead compounds for pharmacological agents capable of blocking Caspase 8 prodomain and TRAFs interactions for the purpose of blocking Caspase 8-TRAFs signal transduction pathway.

EXAMPLE 29

Figure 27:
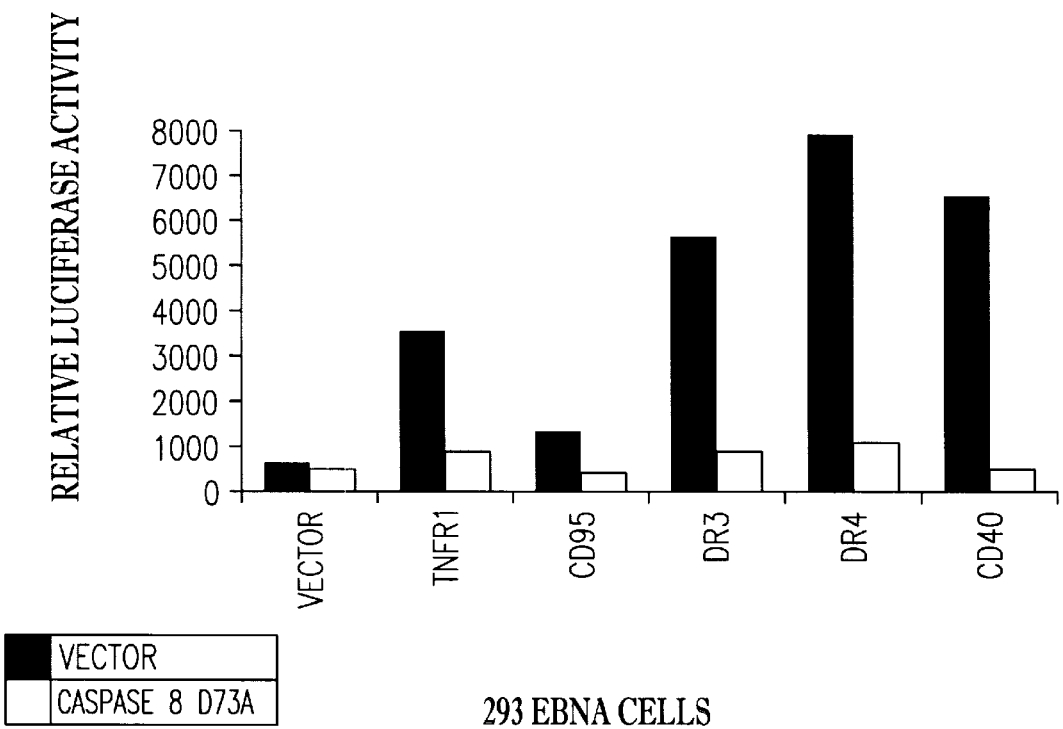
FIG. 27 is a graph similar to that of FIG. 26 illustrating the expression of luciferase in a series of intracellular tests wherein the effect of Caspase 8 mutant (D73A) on JNK activity induced by TNFR1, Fas/CD95, DR3, DR4 and CD40 in 293T cells was measured, as compared with a null vector control.

As demonstrated in FIG. 27, the protease domain (ICE-homology domain or Caspase domain) of Caspase 8 can interact with TRAF proteins. This experiment was conducted to determine whether interaction with TRAF proteins is a general property of the protease domain which can therefore be extended to non-DEDs-containing Caspases as well. Therefore, this experiment examined whether Caspase 7, a non-DEDs-containing Caspase, can interact with TRAF1 and NIK proteins. The co-expression-immunoprecipitation assay utilized was similar to that described in Example 24 except the first expression vector consisted of FLAG-tagged Caspase 7 C186S and the second expression vector consisted of HA-tagged mTRAF1 or HA-tagged NIK. FLAG-tagged proteins were immunoprecipitated using FLAG beads or control beads, and co-immunoprecipitating HA-mTRAF1 or HA-NIK was detected by western blot analysis using a rabbit polyclonal antibody against the HA tag.

Figure 34:
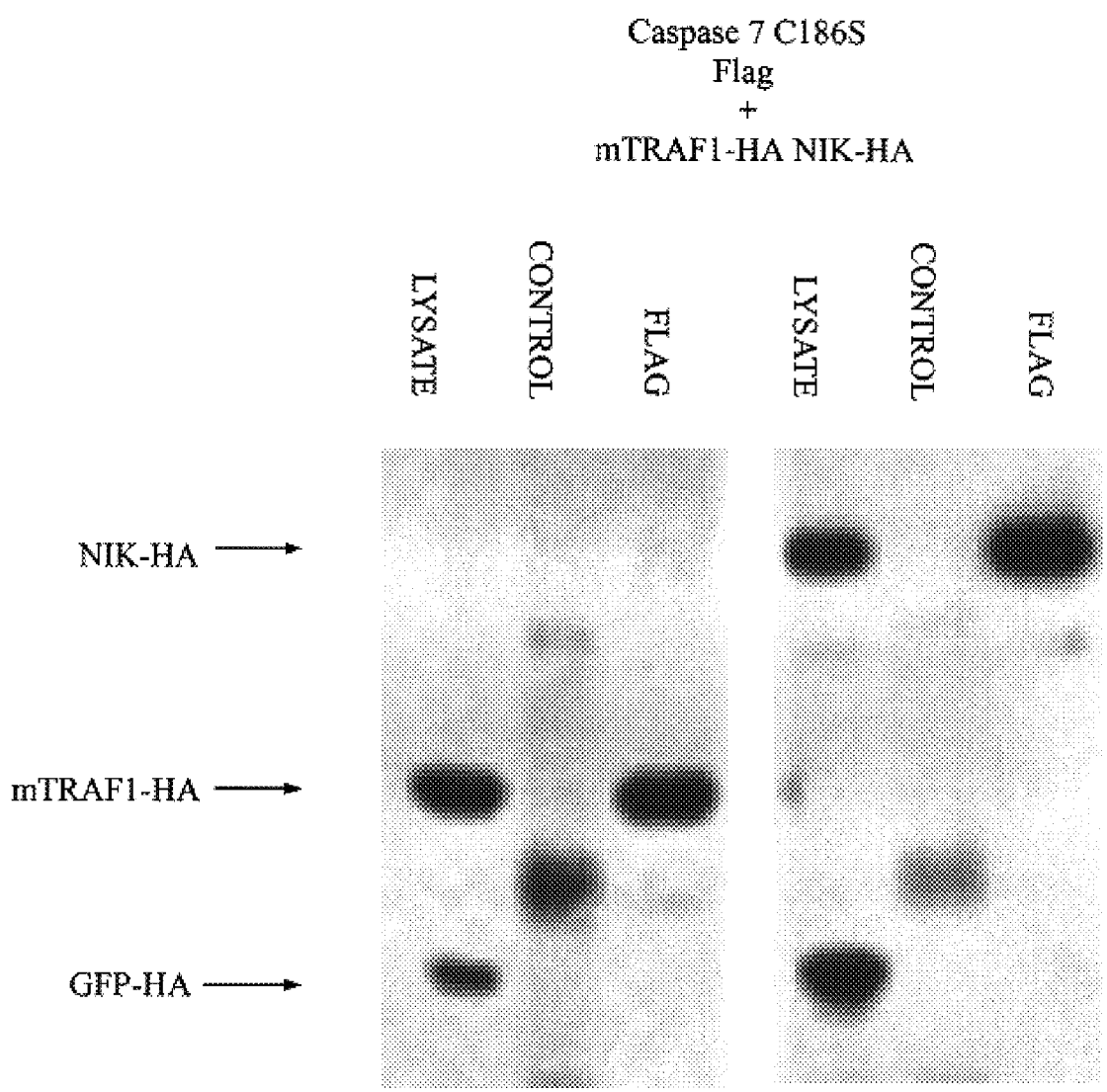
FIG. 34 is a series of photographs depicting the results of a co-expression-immunoprecipitation assay wherein the interaction between Caspase 7 mutant (C186S) FLAG and NIK-HA and mTRAF1-HA/GFP-HA was measured in 293T cells as compared with a control, wherein the lysate lane shows the expression of the HA-tagged proteins in the total cellular extract.

The results of this experiment are shown in FIG. 34 and demonstrate that Caspase 7 directly interacts with TRAF1 and NIK proteins when co-expressed with TRAF1 or NIK in mammalian cells. This example also illustrates that an assay based on the interactions between Caspase 7 and TRAF1 or NIK can be used as a screening tool for identifying lead compounds for pharmacological agents capable of inhibiting the interactions between Caspase 7 and TRAF1, or Caspase 7 and NIK, for the purpose of diagnosis and treatment of diseases associated with the dysfunction of the Caspase 7-TRAF1 and Caspase 7-NIK signal transduction pathway.

EXAMPLE 30

In Example 27, it was demonstrated that two DEDs-containing proteins, the Caspase 8 prodomain and the MRIT-β1 isoform (containing its prodomain) can interact with the mTRAF1 protein. This experiment was conducted to determine whether DEDs-containing proteins in general can interact with the TRAF family of proteins using the co-expression-immunoprecipitation assay. The procedure was similar to that described in Example 24 except the first expression vector consisted of FLAG-tagged K13-ORF, MC159L, MRIT-β1, or PEA-15 and the second expression vector consisted of HA-tagged mTRAF2. FLAG-tagged proteins were immunoprecipitated using FLAG beads. Co-immunoprecipitating HA-mTRAF2 was detected by western blot analysis using a rabbit polyclonal antibody against the HA tag.

Figure 35:
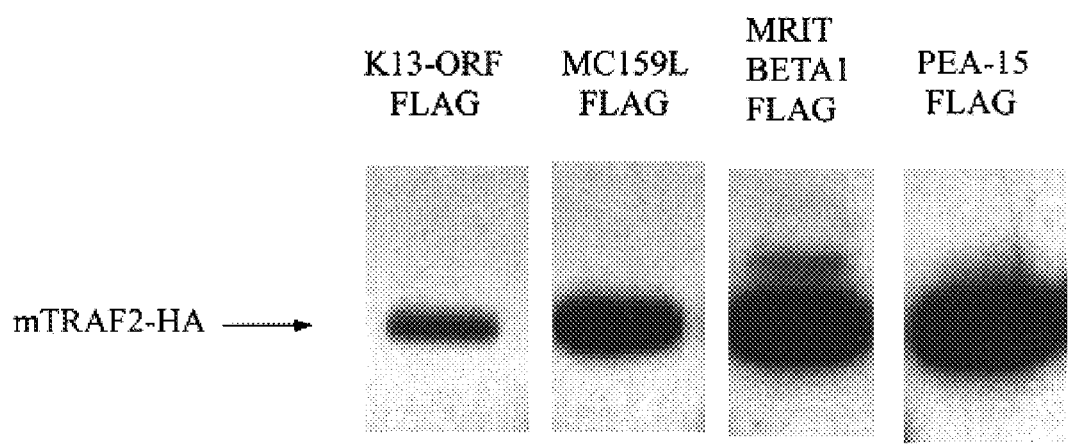
FIG. 35 is a series of photographs depicting the results of a co-expression-immunoprecipitation assay wherein the interaction between mTRAF2-HA and K13-ORF FLAG, MC159L FLAG, MRIT-β1 FLAG and PEA-15 FLAG was measured in 293T cells.

The results of this experiment are shown in FIG. 35 and demonstrate that DEDs-containing proteins interact with TRAF2. This example combined with Example 27 also illustrates that interaction with TRAF proteins is a general property of DEDs-containing proteins. An assay based on these interactions between DEDs-containing proteins and the TRAF family of proteins can therefore be used as a screening tool for identifying lead compounds for pharmacological agents capable of blocking DEDs-TRAFs interaction for the purpose of inhibiting DEDs-TRAFs signal transduction pathway.

EXAMPLE 31

This experiment was conducted to determine whether various Caspases and DEDs-containing proteins interact with NIK proteins, a serine-threonine kinase involved in the activation it he NF-κB pathway. The co-expression-immunoprecipitation assay utilized was similar to that described in Example 24 except the first expression vector consisted of FLAG-tagged Caspase 8 C360S, Caspase 8 protease domain (a.a. 217-479), Caspase 10, MRIT, Caspase 7, K13-ORF, or PEA-15, and the second expression vector consisted of HA-tagged NIK. FLAG-tagged proteins were immunoprecipitated using FLAG beads or control beads, and co-immunoprecipitating HA-NIK was detected by western blot analysis using a rabbit polyclonal antibody against the HA tag.

Figure 36:
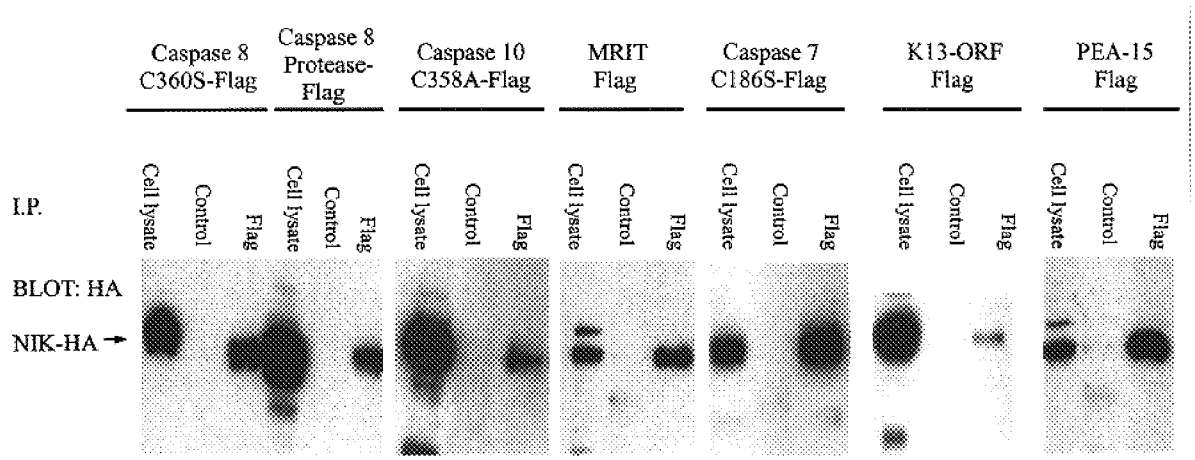
FIG. 36 is a series of photographs depicting the results of a co-expression-immunoprecipitation assay wherein the interaction between NIK-HA and Caspase 8 mutant (C360S) FLAG, Caspase 8 protease FLAG, Caspase 10 mutant (C358A) FLAG, MRIT-α1 FLAG, Caspase 7 mutant (C186S) FLAG, K13-ORF FLAG and PEA-15 FLAG was measured in 293T cells, as compared with a control, wherein the lysate lane shows the expression of the HA-tagged proteins in the total cellular extract.

The results of this experiment are shown in FIG. 36 and demonstrate that Caspase 8, Caspase 8 protease domain (a.a. 217-479), Caspase 10, MRIT, Caspase 7, K13-ORF, and PEA-15 directly interact with NIK proteins when co-expressed with NIK in mammalian cells. This example shows that DEDs- and protease domain-containing proteins can in general interact with NIK. An assay based on this interaction can be used as a screening tool for identifying lead compounds for pharmacological agents capable of blocking DEDs or protease domain-containing proteins with NIK interaction for the purpose of inhibiting DEDs-containing proteins-NIK and protease domain-containing proteins-NIK signal transduction pathway.

EXAMPLE 32

Figure 37:
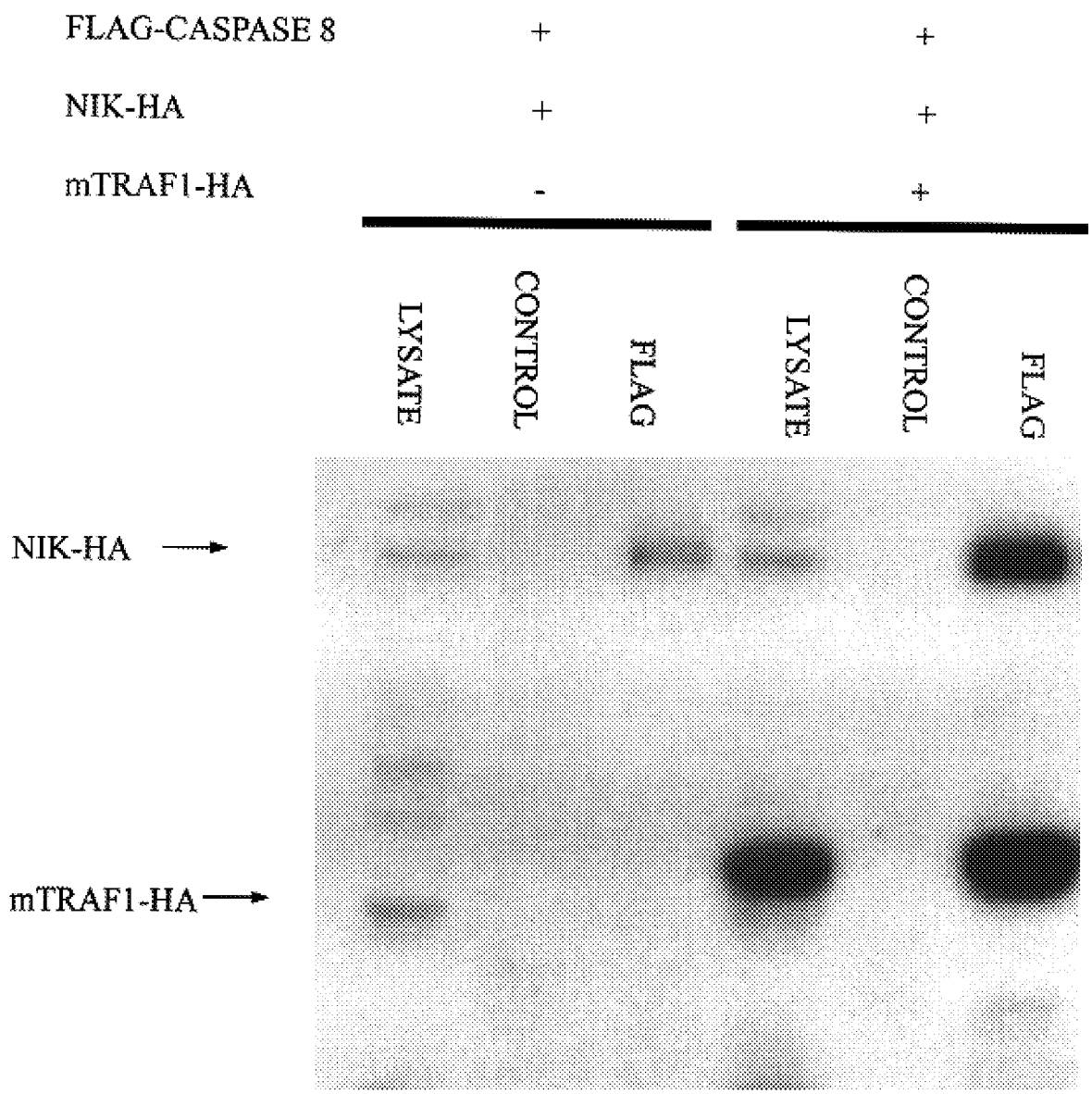
FIG. 37 is a series of photographs depicting the results of a co-expression-immunoprecipitation assay wherein the effect of mTRAF1-HA on interactions between NIK-HA and Caspase 8 FLAG was measured in 293T cells, as compared with a control and a lysate control.

This experiment was conducted to determine whether TRAF proteins influence the interactions between Caspase 8 and NIK. The procedure was similar to that described in Example 24 except the expression vectors encoding FLAG-tagged Caspase 8 and HA-tagged NIK were co-transfected in the absence or presence of HA-mTRAF1 as shown in FIG. 37. FLAG-tagged proteins were immunoprecipitated using FLAG beads or control beads. Co-immunoprecipitating HA-NIK and/or HA-mTRAF1 were detected by western blot analysis using a rabbit polyclonal antibody against the HA tag. A similar procedure was followed using mTRAF2 in place of mTRAF1.

Figure 38:
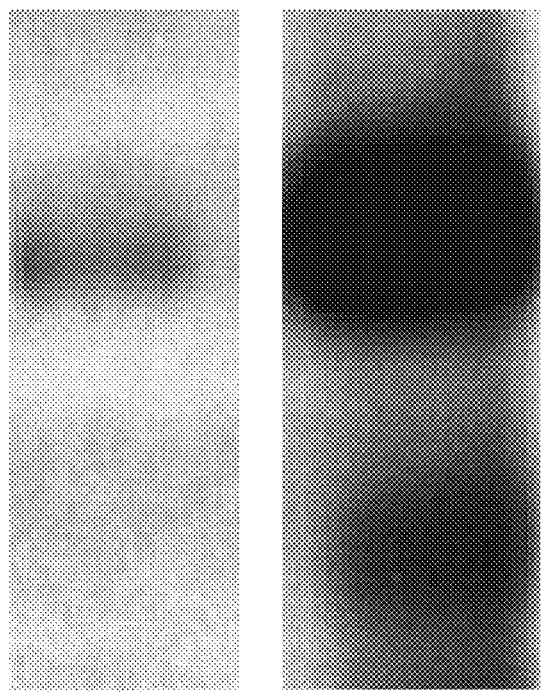
FIG. 38 is a series of photographs depicting the results of a co-expression-immunoprecipitation assay wherein the effect of mTRAF1-HA on interactions between NIK-HA and Caspase 8 mutant (C360S) FLAG was measured in 293T cells.

The results of this experiment are set forth in FIGS. 37 and 38 and demonstrate that co-expression of TRAF proteins leads to a significant increase in the amount of co-precipitating NIK. Therefore, TRAF proteins may be useful as lead compounds for identifying pharmacological agents capable of modulating Caspases-NIK interactions. This example also illustrates that an assay based on the interactions between Caspase 8 and NIK can be used as a screening tool for identifying lead compounds for pharmacological agents capable of modulating Caspase 8 and NIK interactions for the purpose of modulating Caspase 8-NIK signal transduction pathway.

EXAMPLE 33

This experiment was conducted to determine whether various Caspases and DEDs-containing proteins can interact with RIP, another serine-threonine kinase involved in the inactivation of the NF-κB pathway. The co-expression-immunoprecipitation assay utilized was similar to that described in Example 24 except the first expression vector consisted of FLAG-tagged Caspase 8 C360S, Caspase 10 C358A, MRIT, Caspase 8 prodomain (a.a. 1-180), MRIT-β1 isoform (containing its prodomain), K13-ORF, MC159L, or Caspase 7 C186S, and the second expression vector consisted of HA-tagged RIP. FLAG-tagged proteins were immunoprecipitated using FLAG beads or control beads. Co-immunoprecipitating HA-RIP was detected by Western Blot analysis using a rabbit polyclonal antibody against the HA tag.

Figure 39:
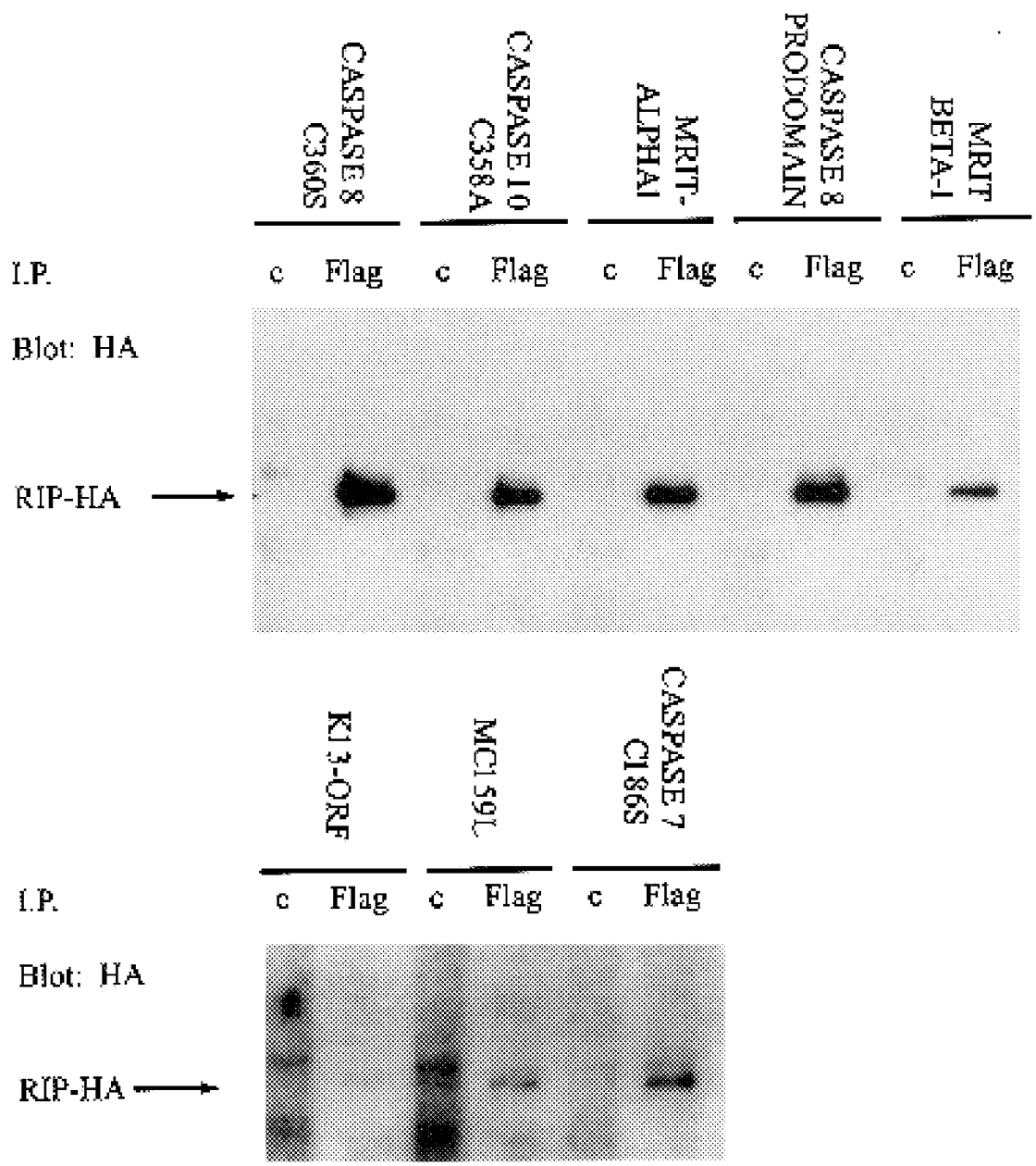
FIG. 39 is a series of photographs depicting the results of a co-expression-immunoprecipitation assay wherein the interactions between RIP-HA and Caspase 8 mutant (C360S) FLAG, Caspase 10 mutant (C358A) FLAG, MRIT-α1 FLAG, Caspase 8 prodomain FLAG and MRIT-β1 FLAG was measured in 293T cells, as compared with a control.

The results of this experiment are shown in FIG. 39. Caspase 8 C360S, Caspase 10 C358A, MRIT, Caspase 8 prodomain (a.a. 1-180), MRIT-β1 isoform (containing its prodomain), K13-ORF, MC159L, and Caspase 7 C186S directly interact with RIP protein when co-expressed with RIP in mammalian cells. This example indicates that Caspases and DEDs-containing proteins can, in general, interact with RIP. An assay based on interactions between Caspases and DEDs-containing proteins with RIP can be used as a screening tool for identifying lead compounds for pharmacological agents capable of blocking interactions between Caspases and DEDs-containing proteins with RIP for the purpose of inhibiting DEDs-containing proteins-RIP and Caspases-RIP signal transduction pathways.

EXAMPLE 34

This experiment was conducted to determine whether Caspase 8 can interact with IKK1 (or IKKα) and IKK2 (or IKKβ) proteins. IKK1 and IKK2, like RIP and NIK, are serine-threonine protein kinases involved in the activation of NF-κB pathway. The co-immunoprecipitation assay followed was similar to that described in Example 24 except the first expression vector consisted of myc-tagged Caspase 8 C360S, and the second expression vector consisted of FLAG-tagged IKK1 or IKK2 respectively. FLAG-tagged proteins were immunoprecipitated using FLAG beads or control beads. Co-immunoprecipitating myc-Caspase 8 was detected by western blot analysis using a rabbit polyclonal antibody against the myc tag.

Figure 40:
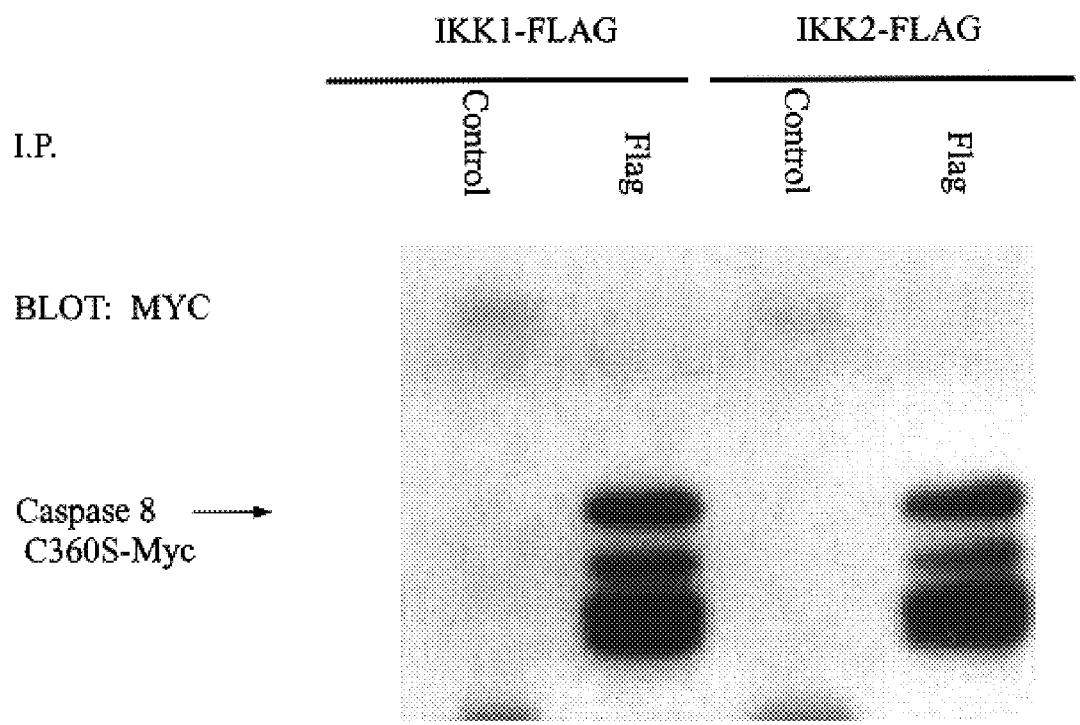
FIG. 40 is a series of photographs depicting the results of a co-expression-immunoprecipitation assay wherein the interactions between Caspase 8 mutant (C360S) and IKK1 FLAG and IKK2 FLAG was measured in 293T cells, as compared with a control.

The results of this experiment are shown in FIG. 40 and demonstrate that Caspase 8 directly interacts with IKK1 and IKK2 proteins when co-expressed with IKK1 or IKK2 in mammalian cells. Furthermore, combined with Examples 29, 31, and 33, this example confirms that Caspases and DEDs-containing proteins can interact with serine-threonine protein kinases. An assay based on interaction between Caspases and DEDs-containing proteins with IKK1 or IKK2 can be used as a screening tool for identifying lead compounds for pharmacological agents capable of modulating interactions between Caspases (and/or DEDs-containing proteins) and IKK1 or IKK2 for the purpose of diagnosis and treatment of diseases associated with the dysfunction of DEDs-containing proteins-IKK1/IKK2 and Caspases-IKK1/IKK2 signal transduction pathways. Similar experiments confirmed that IKK1 also interacts with MRIT-α1.

EXAMPLE 35

This experiment was conducted to test whether Caspase 8 interacts with TRAF proteins in a cell-free system using co-immunoprecipitation of bacterially expressed proteins. Myc-Caspase 8, mTRAF2-FLAG, mTRAF1-HA or a control vector were cloned in pET28 expression vectors. The expression plasmids encoding the above proteins were transformed in to the BL21 (DE3)pLysS host cells. Expression of the target proteins were induced using IPTG and following the manufacturer's instructions (Novagen, Madison, Wis.). After induction for 3 hours, the host cells were pelleted by centrifugation at 4° C. at 3000 g for 10 minutes. The pellet was resuspended in a buffer (20 mM sodium phosphate, 500 mM NaCl, and 1 EDTA-free mini protease inhibitor tablet (Boehringer Mannheim) per 10 ml of buffer) with an amount of buffer which equaled 1/10 of the original culture volume. Cells were lysed by three cycles of freeze-thawing and subsequently sonicated (10 pulses of 5 second each at low energy with output to dial at level 4) at 4° C. using a Branson Sonifier Model 250. The sonicated samples were centrifuged at 10000 g at 4° C., and the supernatant containing the soluble fraction was collected. Five hundred μl of supernatant from cultures expressing mTRAF2-FLAG or mTRAF1-HA were incubated for 1 hour at 4° C. with an equal volume of supernatant from cultures expressing myc-Caspase 8 or control vectors. Immunoprecipitation was carried out with myc beads as previously described, and western blot analysis was performed using rabbit polyclonal antibodies against the HA or FLAG tags as described previously.

Figure 41:
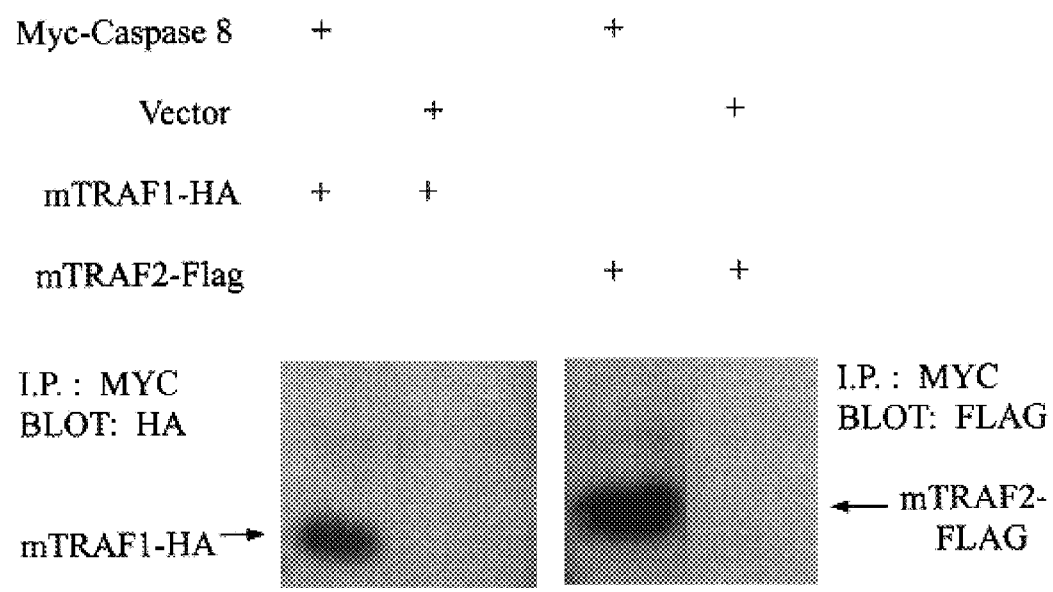
FIG. 41 is a series of photographs depicting the results of a co-expression-immunoprecipitation assay wherein the interactions between Caspase 8 and mTRAF 1-HA and mTRAF2-FLAG were measured in a cell-free system.

The results of this experiment are shown in FIG. 41 and indicate that Caspase 8 can directly interact with TRAF1 or TRAF2 proteins in cell-free systems. This example demonstrate that a cell-free binding assay based on interaction between Caspase 8 and TRAF1 or TRAF2 can also be used as a screening tool for identifying lead compounds for pharmacological agents capable of selectively blocking Caspase 8 and TRAF1 or TRAF2 interaction for the purpose of blocking Caspase 8-TRAFs signal transduction pathways.

EXAMPLE 36

This experiment was conducted to demonstrate that K13-ORF, a DEDs-containing protein, directly interacts with TRAF proteins in the yeast two-hybrid system. For this purpose, K13-ORF was cloned in the DNA binding domain vector pLexA, and mTRAF1 or mTRAF2 were cloned in the activation domain vector pB42AD. The yeast two-hybrid interaction assay was performed as described in the manual accompanying the MATCHMAKER LexA Two-Hybrid System (Clontech, Palo Alto, Calif.).

The results observed in this experiment indicated that K13-ORF directly interacts with either mTRAF1 or mTRAF2 in the yeast two-hybrid interaction assay. The results further show that a yeast two-hybrid interaction assay between K13-ORF and TRAF1 can be used as a screening tool for identifying lead compounds for pharmacological agents capable of blocking K13 -ORF and TRAF1 or TRAF2 interaction for the purpose of inhibiting K13-ORF-TRAFs signal transduction pathways.

EXAMPLE 37

The purpose of this experiment was to determine the role of TRAF proteins in the mediation of cell death induced by various Caspases. For this purpose, 293T cells ($1\times10^5$) were seeded in each well of a 24 well tissue culture plate. Twenty-four hours later, the cells were transfected with 250 ng/well of a first plasmid (control vector, Caspase 8, Caspase 8 C360S, or Caspase 8 prodomain (a.a. 1-180) along with 250 ng/well of a second plasmid (control vector, mTRAF2, or mTRAF2+crmA) using the calcium phosphate co-precipitation method described in Example 1. An RSV/LacZ reporter plasmid (100 ng/well) encoding the β-galactosidase protein was co-transfected into all the wells. Twenty four hours after transfection, the cells were fixed and stained with X-gal. The percentage of apoptotic cells was determined as described in Chaudhary et al., *Immunity*, 7:821–830 (1997).

Figure 42:
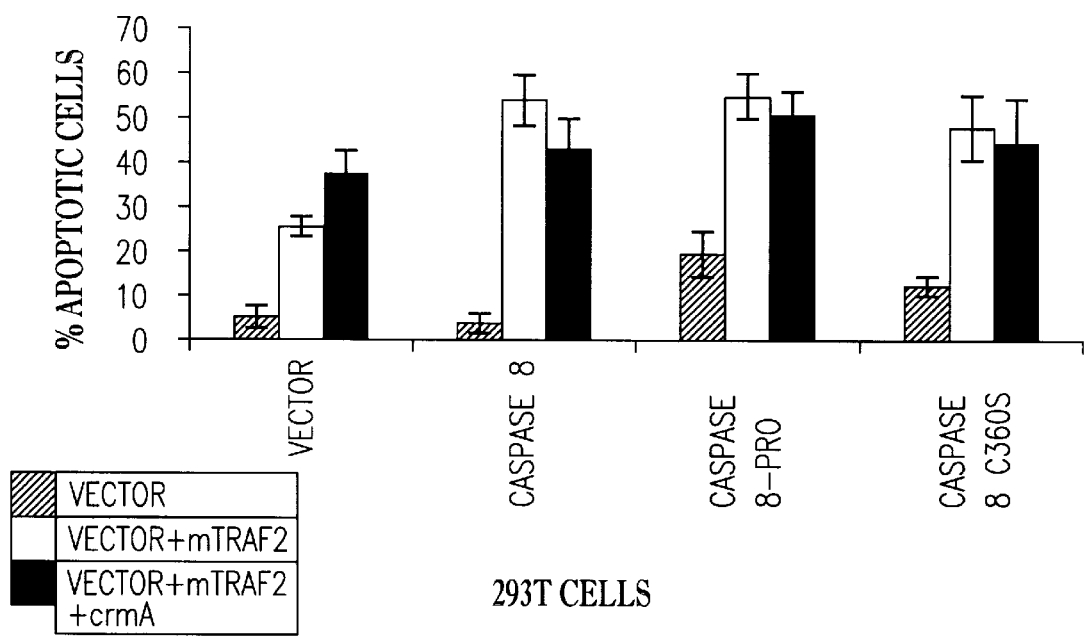
FIG. 42 is a graph illustrating the results of a series of apoptotic cell experiments wherein the effect of mTRAF2 and mTRAF2+crmA upon cell death induced by Caspase 8, Caspase 8 prodomain (a.a. 1-180) and Caspase 8 mutant (C360S) in 293T cells was measured.

The results of this experiment are shown in FIG. 42 and indicate that mTRAF2 has slight pro-apoptotic ability when expressed alone in mammalian cells. However, in the presence of the various Caspase 8 constructs, an increase in the number of apoptotic cells is observable, indicating that TRAF2 and Caspase 8 cooperate with each other to induce cell death. Essentially similar results were obtained when mTRAF2 was co-expressed with MRIT. These results demonstrate that agents interfering with Caspase-TRAF or MRIT-TRAF interactions may be useful as lead compounds for identifying pharmacological agents useful for the treatment of diseases resulting from the dysfunction of apoptotic pathways.

EXAMPLE 38

This experiment was conducted to determine the role of activation of NF-κB and JNK pathways in the mediation of cell death induced by various Caspases. For this purpose, selective inhibitors of the NF-κB pathway (i.e., IκB-ΔN) and of the JNK pathway (i.e., JIP) were used to block cell death mediated by Caspase 10 (Mch4 isoform) and Caspase 9. The procedure used was similar to that described in Example 37 except that 293T cells were transfected with 100 ng/well of the first plasmid (i.e., control vector, Caspase 10 (Mch4 isoform), and Caspase 9), along with 750 ng/well the second plasmid (i.e., control vector, IκB-ΔN, DN-IkappaB and JIP).

Figure 43:
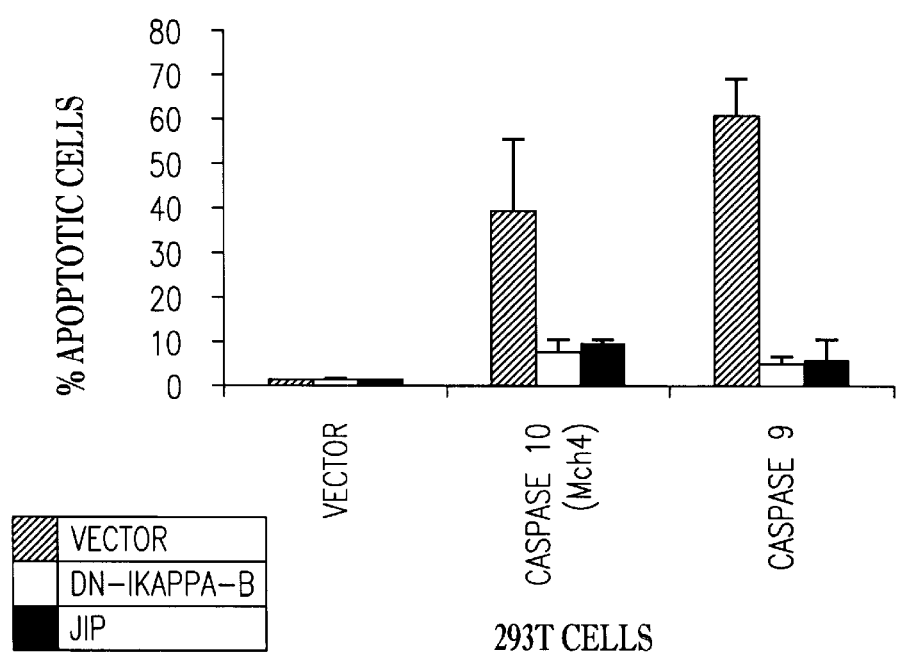
FIG. 43 is a graph illustrating the results of a series of apoptotic cell experiments wherein the effect of $I_κB$-ΔN and JIP upon cell death induced by Caspase 10 Mch4 isoform and Caspase 9 in 293T cells was measured, as compared with a control.

The results of this experiment are set forth in FIG. 43 and indicate that Caspase 10 and Caspase 9 induced-apoptosis can be blocked by IκB-ΔN and JIP. Thus, activation of the NF-κB and JNK pathways plays an important role in the mediation of cell death induced by Caspases. Agents interfering with activation of NF-κB and JNK pathways may be useful as lead compounds for identifying pharmacological agents for the treatment of diseases resulting from the dysfunction of apoptotic pathways.

EXAMPLE 39

Figure 44:
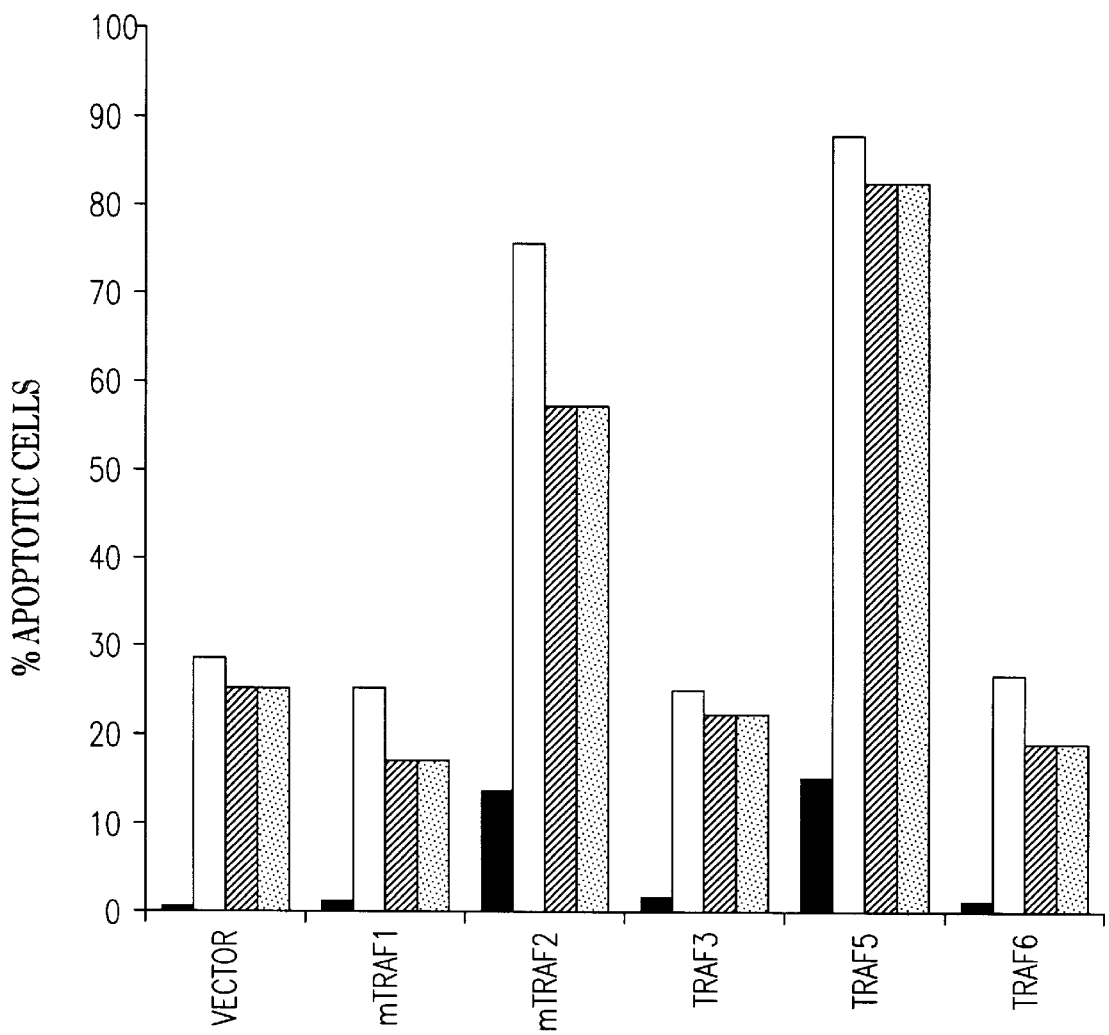
FIG. 44 is a graph illustrating the results of a series of apoptotic cell experiments wherein the effect of mTRAF1, mTRAF2, TRAF3, TRAF5 and TRAF6 upon cell death induced by Caspase 10, Caspase 7 and Caspase 9 in 293T cells was measured, as compared with a control.

This experiment was conducted to determine the role of TRAF proteins in the mediation of cell death induced by various Caspases. The procedure used was similar to that described in Example 37 except that the cells were transfected with 100 ng/well of the first plasmid (control vector, Caspase 10, Caspase 9 or Caspase 7) along with 750 ng/well of the second plasmid (control vector, mTRAF1, mTRAF2, TRAF3, mTRAF5 and TRAF6) using the calcium phosphate co-precipitation method described in Example 1. The results of this experiment are shown in FIG. 44 and indicate mTRAF2 and TRAF5 have slight pro-apoptotic ability when expressed alone in mammalian cells. However, in the presence of the various Caspase constructs, an increase in the number of apoptotic cells is seen indicating that Caspases and TRAFs cooperate with each other to induce cell death. These results demonstrate that agents interfering with Caspase-TRAF interaction may be useful as lead compounds for identifying pharmacological agents for the treatment of diseases resulting from the dysfunction of apoptotic pathways.

In the course of development of the present invention, novel signal transduction pathways important for the regulation of apoptosis and immune and inflammatory responses have been discovered. The invention makes use of this knowledge to provide methods for the identification, development and use of therapeutic agents (or lead compounds therefor) which intervene at specific points in these pathways. The following are certain specific therapeutic applications within the ambit of the invention.

It has been demonstrated that DEDs-containing Caspases and Caspase homologs (e.g., MRIT-α1) can directly interact with TRAF family of adaptor proteins and activate the NF-κB pathway, and that this interaction has functional significance in the activation of the NF-κB pathway by the members of the TNFR family. Several dominant negative inhibitors of this interaction have been identified which can block the activation of NF-κB pathway by the TNFR family members. Additional inhibitors of this interaction can thus be readily developed based on the knowledge that conserved residues among the different DEDs-containing proteins are critical for this activity. For example, it has been found that mutation of a single amino acid at the conserved residues 73, 74 or 75 results in the partial or complete loss of NF-κB activation by Caspase 8, and that these mutants can block NF-κB activation by wild-type Caspase 8 and TNFR family members. Several other amino acids are highly conserved among the various DEDs-containing proteins and may be readily tested using site-directed mutagenesis. Such mutants may be useful therapeutic agents (or lead compounds) for controlling cell death and inflammation resulting from the activation of the NF-κB pathway. One scenario would be the use of gene therapy with these agents for the primary or secondary prevention of coronary artery disease. As mentioned above, activation of NF-κB pathway has been implicated in the pathogenesis of atherosclerosis. With the rapid advances in the gene therapy technology, it is possible to deliver such a mutated gene to the endothelial cells lining the coronary arteries using either liposomes or viral vectors at the time of coronary angioplasty. Similarly, such dominant negative inhibitors may have potential applications in the gene therapy for rheumatoid arthritis, cancer and AIDS.

Another area of potential therapeutic application(s) in the area of cell permeable peptide analogs. These analogs can be easily synthesized based on the knowledge of the primary sequence of the interacting domains. For example, it is possible to synthesize small peptides or polypeptides corresponding to the region (s) that are conserved among the various DEDs-containing proteins. Such small peptides are either intrinsically cell permeable or made so by the attachment of a side chain. A good example of this approach is provided by z-VAD-fink, a cell permeable small peptide inhibitor of the protease activity of several Caspases. Similar analogs are currently under development or in clinical trials for the treatment of liver failure and neurological disorders resulting from overactivity of caspases.

Development of small molecule inhibitors represent another potential area of drug discovery based on the present invention. Using the techniques of combinatorial chemistry, small molecules can be synthesized which may bind to the interacting domains of Caspases, TRAFs or serine-threonine protein kinases. Such small molecules could be readily screened for their ability to inhibit Caspase induced NF-κB by the methods hereof.

It has also been discovered that interaction of Caspase 8, 10 and MRIT-α1 also leads to the activation of JNK pathway. Therefore, the agents identified herein may find usefulness in the treatment of disease manifestations resulting from the activation of JNK pathway by these Caspases.

The finding of a pro-apoptotic role of TRAF2 and TRAF5 provides a mechanism by which several non-death domain containing members of the TNFR family, such as TNFR2, CD40, CD30 (GenBank P28908) and LTβR, may mediate cell death. These receptors have been shown to bind to TRAF proteins, but the mechanism by which they mediate cell death has not been elucidated. The TRAF proteins have been found to directly bind to Caspase 7, 8 and 10, thus providing a molecular framework for the mediation of cell death by these receptors. Therefore, agents that can block the interaction of TRAF proteins with Caspases may be used for the treatment of diseases resulting from the dysfunction/overactivity of these receptors. These agents might include dominant-negative mutants of Caspases, cell permeable peptide homologs, small molecule compounds or antisense agents.

One of the proteins encoded by the Kaposi sarcoma associated Herpes Virus (K13-ORF) can directly interact with TRAF proteins and serine-threonine protein kinases and activate the NF-κB pathway. This finding is of critical importance for the development of therapeutic agents against the various malignancies caused by this agent. This finding is of special interest because Epstein-Barr Virus (EBV), another herpes virus that has been associated with several human malignancies, has been shown to produce a protein which interacts with the TRAF proteins. Agents which interfere with the interaction of K134-ORF with the TRAF proteins may prove to be effective therapeutic agents against KS, multiple myeloma and other malignancies associated with KSHV and for which no effective therapy is available at present.

MC159L, a DEDs-containing protein encoded by the Molluscum Contagiosum virus, binds to TRAF2 but does not activate NF-κB. Moreover, MC159L is an effective inhibitor of NF-κB activation mediated by Caspases. As lack of an inflammatory response to the virus plays a crucial role in the persistence and recurrence of the molluscum contagiosum infection, agents blocking the activity of MC159L may be used to elicit an immune response to this infection. Such agents could include peptides, small molecules or DNA fragments encoding antisense or dominant negative inhibitors. Due to the cutaneous nature of this infection, it will be relatively easy to deliver the above agents to the target lesion using a number of currently available drug/gene delivery technologies. Alternatively, MC159L or its analogs may be used as anti-inflammatory agents for the treatment of diseases caused by undesirable inflammatory response such as rheumatoid arthritis, cerebral/myocardial infarction and septic shock.

It has been found that all dual DEDs-containing proteins interact with TRAF family members. In addition to KSHV and MC159L, such DEDs-containing proteins have been discovered in other viruses such as herpes virus simirii, bovine herpes virus and equine herpes virus. As a result of large scale genomic sequencing, such dual DEDs-containing proteins are likely to be discovered in other viruses of clinical importance in future.

Evidence is provided that Caspase 7, 8, 10, MRIT-α1 and DEDs-containing viral open reading frames can directly interact with NIK, RIP, IKK1 and IKK2. Moreover, IKK1 can interact with RIP. Thus, a TRAF-independent pathway has been identified for the activation of NF-κB. Knowledge of this pathway can be used to develop highly specific inhibitors of NF-κB activation mediated by various members of the TNFR family.

REFERENCES

Berberich, I., Shu, G. L., and Clark, E. A. (1994). Cross-linking CD40 on B cells rapidly activates nuclear factor-kappa. B. *J Immunol,* 153:4357–66.

Brockman, J. A., Scherer, D. C., McKinsey, T. A., Hall, S. M., Qi, X., Lee, W. Y., and Ballard, D. W. (1995). Coupling of a signal response domain in I kappa B alpha to multiple pathways for NF-κB activation. *Mol Cell Biol,* 15:2809–18.

Chaudhary, P. M., Eby, M., Jasmin, A., Bookwalter, A., Murray, J., and Hood, L. (1997). Death receptor 5, a new member of the TNFR family, and DR4 induce FADD-dependent apoptosis and activate the NF-κB pathway. *Immunity,* 7:821–30.

Cheng, G., Cleary, A. M., Ye, Z. S., Hong, D. I., Lederman, S., and Baltimore, D. (1995). Involvement of CRAF1, a relative of TRAF, in CD40 signaling. *Science* 267:1494–8.

Chinnaiyan, A. M., K, O. R., Tewari, M., and Dixit, V. M. (1995). FADD, a novel death domain-containing protein, interacts with the death domain of Fas and initiates apoptosis. *Cell* 81:505–12.

Chinnaiyan, A. M., K, O. R., Yu, G. L., Lyons, R. H., Garg, M., Duan, D. R., Xing, L., Gentz, R., Ni, J., and Dixit, V. M. (1996). Signal transduction by DR3, a death domain-containing receptor related to TNFR-1 and CD95. *Science,* 274:990–2.

Dickens, M., Rogers, J. S., Cavanagh, J., Raitano, A., Xia, Z., Halpern, J. R., Greenberg, M. E., Sawyers, C. L., and Davis, R. J. (1997). A cytoplasmic inhibitor of the JNK signal transduction pathway. *Science,* 277:693–6.

Duan, H., Chinnaiyan, A. M., Hudson, P. L., Wing, J. P., He, W. W., and Dixit, V. M. (1996). ICE-LAP3, a novel mammalian homologue of the Caenorhabditis elegans cell death protein Ced-3 is activated during Fas- and tumor necrosis factor-induced apoptosis. *J Biol Chem,* 271:1621–5.

Duan, H., Orth, K., Chinnaiyan, A. M., Poirier, G. G., Froelich, C. J., He, W. W., and Dixit, V. M. (1996). ICE-LAP6, a novel member of the ICE/Ced-3 gene family, is activated by the cytotoxic T cell protease granzyme B. *J Biol Chem,* 271:16720–4.

Duckett, C. S., and Thompson, C. B. (1997). CD30-dependent degradation of TRAF2: implications for negative regulation of TRAF signaling and the control of cell survival. *Genes Dev* 11:2810–21.

Fernandes-Alnemri, T., Armstrong, R. C., Krebs, J., Srinivasula, S. M., Wang, L., Bullrich, F., Fritz, L. C., Trapani, J. A., Tomaselli, K. J., Litwack, G., and Alnemri, E. S. (1996). In vitro activation of CPP32 and Mch3 by Mch4, a novel human apoptotic cysteine protease containing two FADD-like domains. *Proc Natl Acad Sci U.S.A.*, 93:7464–9.

Han, D. K., Chaudhary, P. M., Wright, M. E., Friedman, C., Trask, B. J., Riedel, R. T., Baskin, D. G., Schwartz, S. M., and Hood, L. (1997). MRIT, a novel death-effector domain-containing protein, interacts with caspases and BclXL and initiates cell death. *Proc Natl Acad Sci U.S.A.*, 94:11333–8.

Hu, S., Vincenz, C., Buller, M., and Dixit, V. M. (1997). A novel family of viral death effector domain-containing molecules that inhibit both CD-95- and tumor necrosis factor receptor-1-induced apoptosis. *J Biol Chem*, 272:9621–4.

Muzio, M., Chinnaiyan, A. M., Kischkel, F. C., K, O. R., Shevchenko, A., Ni, J., Scaffidi, C., Bretz, J. D., Zhang, M., Gentz, R., Mann, M., Krammer, P. H., Peter, M. E., and Dixit, V. M. (1996). FLICE, a novel FADD-homologous ICE/CED-3-like protease, is recruited to the CD95 (Fas/APO-1) death-inducing signaling complex. *Cell*, 85:817–27.

Nakano, H., Oshima, H., Chung, W., Williams-Abbott, L., Ware, C. F., Yagita, H., and Okumura, K. (1996). MTRAF5, an activator of NF-κB and putative signal transducer for the lymphotoxin-beta receptor. *J Biol Chem*, 271:14661–4.

Nakano, H., Shindo, M., Sakon, S., Nishinaka, S., Mihara, M., Yagita, H., and Okumura, K. (1998). Differential regulation of IkappaB kinase alpha and beta by two upstream kinases, NF-κB-inducing kinase and mitogen-activated protein kinase/ERK kinase kinase-1. *Proc Natl Acad Sci U.S.A.*, 95:3537–42.

Natoli, G., Costanzo, A., Moretti, F., Fulco, M., Balsano, C., and Levrero, M. (1997). Tumor necrosis factor (TNF) receptor 1 signaling downstream of TNF receptor-associated factor 2. Nuclear factor kappaB (NFkappaB)-inducing kinase requirement for activation of activating protein 1 and NFkappaB but not of c-Jun N-terminal kinase/stress-activated protein kinase. *J Biol Chem*, 272:26079–82.

Rothe, M., Wong, S. C., Henzel, W. J., and Goeddel, D. V. (1994). A novel family of putative signal transducers associated with the cytoplasmic domain of the 75 kDa tumor necrosis factor receptor. *Cell*, 78:681–92.

Rothe, M., Xiong, J., Shu, H. B., Williamson, K., Goddard, A., and Goeddel, D. V. (1996). I-TRAF is a novel TRAF-interacting protein that regulates TRAF-mediated signal transduction. *Proc Natl Acad Sci U.S.A.*, 93:8241–6.

Sarma, V., Lin, Z., Clark, L., Rust, B. M., Tewari, M., Noelle, R. J., and Dixit, V. M. (1995). Activation of the B-cell surface receptor CD40 induces A20, a novel zinc finger protein that inhibits apoptosis. *J Biol Chem*, 270:12343–6.

Stamenkovic, I., Clark, E. A., and Seed, B. (1989). A B-lymphocyte activation molecule related to the nerve growth factor receptor and induced by cytokines in carcinomas. *Embo J*, 8:1403–10.

Tewari, M., and Dixit, V. M. (1995). Fas- and tumor necrosis factor-induced apoptosis is inhibited by the poxvirus crmA gene product. *J Biol Chem*, 270:3255–60.

Tewari, M., Quan, L. T., K, O. R., Desnoyers, S., Zeng, Z., Beidler, D. R., Poirier, G. G., Salvesen, G. S., and Dixit, V. M. (1995). Yama/CPP32 beta, a mammalian homolog of CED-3, is a CrmA-inhibitable protease that cleaves the death substrate poly(ADP-ribose) polymerase. *Cell*, 81:801–9.

Thornberry, N. A., Bull, H. G., Calaycay, J. R., Chapman, K. T., Howard, A. D., Kostura, M. J., Miller, D. K., Molineaux, S. M., Weidner, J. R., Aunins, J., and et al. (1992). A novel heterodimeric cysteine protease is required for interleukin-1 beta processing in monocytes. *Nature*, 356:768–74.

Vincenz, C., and Dixit, V. M. (1997). Fas-associated death domain protein interleukin-1beta-converting enzyme 2 (FLICE2), an ICE/Ced-3 homologue, is proximally involved in CD95- and p55-mediated death signaling. *J Biol Chem*, 272:6578–83.

Wang, L., Miura, M., Bergeron, L., Zhu, H., and Yuan, J. (1994). Ich-1, an Ice/ced-3-related gene, encodes both positive and negative regulators of programmed cell death. *Cell*, 78:739–50.

We claim:

1. A protein selected from the group consisting of SEQ ID NO:26, SEQ ID NO:27 and SEQ ID NO:28.

* * * * *

SEQUENCE LISTING

```
<160> NUMBER OF SEQ ID NOS: 40

<210> SEQ ID NO 1
<211> LENGTH: 78
<212> TYPE: PRT
<213> ORGANISM: Homo sapiens

<400> SEQUENCE: 1

Met Ser Ala Glu Val Ile His Gln Val Glu Glu Ala Leu Asp Thr Asp
 1               5                  10                  15

Glu Lys Glu Met Leu Leu Phe Leu Cys Arg Asp Val Ala Ile Asp Val
            20                  25                  30

Val Pro Pro Asn Val Arg Asp Leu Leu Asp Ile Leu Arg Glu Arg Gly
        35                  40                  45

Lys Leu Ser Val Gly Asp Leu Ala Glu Leu Leu Tyr Arg Val Arg Arg
    50                  55                  60
```

-continued

```
Phe Asp Leu Leu Lys Arg Ile Leu Lys Met Asp Arg Lys Ala
 65                  70                  75

<210> SEQ ID NO 2
<211> LENGTH: 84
<212> TYPE: PRT
<213> ORGANISM: HUMAN HERPESVIRUS 8

<400> SEQUENCE: 2

Val Ser Asp Tyr Arg Val Leu Met Ala Glu Ile Gly Glu Asp Leu Asp
  1               5                  10                  15

Lys Ser Asp Val Ser Ser Leu Ile Phe Leu Met Lys Asp Tyr Met Gly
                 20                  25                  30

Arg Gly Lys Ile Ser Leu Glu Leu Ser Phe Leu Asp Leu Val Val Glu
             35                  40                  45

Leu Glu Lys Leu Asn Leu Val Ala Pro Asp Gln Leu Asp Leu Leu Glu
         50                  55                  60

Lys Cys Leu Lys Asn Ile His Arg Ile Asp Leu Lys Thr Lys Ile Gln
 65                  70                  75                  80

Lys Tyr Lys Gln

<210> SEQ ID NO 3
<211> LENGTH: 79
<212> TYPE: PRT
<213> ORGANISM: HUMAN HERPESVIRUS 8

<400> SEQUENCE: 3

Met Ala Thr Tyr Glu Val Leu Cys Glu Val Ala Arg Lys Leu Gly Thr
  1               5                  10                  15

Asp Asp Arg Glu Val Val Leu Phe Leu Leu Asn Val Phe Ile Pro Gln
                 20                  25                  30

Pro Thr Leu Ala Gln Leu Ile Gly Ala Leu Arg Ala Leu Lys Glu Glu
             35                  40                  45

Gly Arg Leu Thr Phe Pro Leu Leu Ala Glu Cys Leu Phe Arg Ala Gly
         50                  55                  60

Arg Arg Asp Leu Leu Arg Asp Leu Leu His Leu Asp Pro Arg Phe
 65                  70                  75

<210> SEQ ID NO 4
<211> LENGTH: 49
<212> TYPE: PRT
<213> ORGANISM: Equine Herpesvirus

<400> SEQUENCE: 4

Phe Ser Pro Tyr Gln Leu Thr Val Leu His Val Asp Gly Glu Leu Cys
  1               5                  10                  15

Ala Arg Asp Ile Arg Ser Leu Ile Phe Leu Ser Lys Asp Thr Ile Gly
                 20                  25                  30

Ser Arg Ser Thr Pro Gln Thr Ser Tyr Thr Gly Cys Thr Val Trp Leu
             35                  40                  45

Thr

<210> SEQ ID NO 5
<211> LENGTH: 79
<212> TYPE: PRT
<213> ORGANISM: Equine Herpesvirus

<400> SEQUENCE: 5

Met Ser His Tyr Ser Met Ile Asp Thr Tyr Phe Ser Leu Asp Glu Asp
```

-continued

```
                1               5                  10                 15
        Glu Thr Glu Thr Tyr Leu Tyr Leu Cys Arg Asp Leu Leu Lys Asn Lys
                        20                  25                  30

Gly Glu Phe Gln Cys Thr Arg Asp Ala Phe Lys Phe Leu Ser Asp Tyr
                35                  40                  45

Ala Cys Leu Ser Ala Ala Asn Gln Met Glu Leu Leu Phe Ala Val Gly
                50                  55                  60

Arg Leu Asp Leu Ile Arg Arg Ile Phe Gly Gln Thr Trp Thr Pro
        65                  70                  75

<210> SEQ ID NO 6
<211> LENGTH: 82
<212> TYPE: PRT
<213> ORGANISM: Molluscum contagiosum virus

<400> SEQUENCE: 6

Cys Ser Pro Phe Arg Cys Leu Met Ala Leu Val Asn Asp Phe Leu Ser
        1               5                  10                 15

Asp Leu Glu Val Glu Glu Met Tyr Phe Leu Cys Ala Pro Arg Leu Glu
                        20                  25                  30

Ser His Leu Glu Pro Gly Ser Lys Lys Ser Phe Leu Arg Leu Ala Ser
                35                  40                  45

Leu Leu Glu Asp Leu Glu Leu Leu Gly Gly Asp Lys Leu Thr Phe Leu
                50                  55                  60

Arg His Leu Leu Thr Thr Ile Gly Arg Ala Asp Leu Val Lys Asn Leu
        65                  70                  75                  80

Gln Val

<210> SEQ ID NO 7
<211> LENGTH: 82
<212> TYPE: PRT
<213> ORGANISM: Molluscum contagiosum virus

<400> SEQUENCE: 7

Met Ser Asp Ser Lys Glu Val Pro Ser Leu Pro Phe Leu Arg His Leu
        1               5                  10                 15

Leu Glu Glu Leu Asp Ser His Glu Asp Ser Leu Leu Leu Phe Leu Cys
                        20                  25                  30

His Asp Ala Ala Pro Gly Cys Thr Thr Val Thr Gln Ala Leu Cys Ser
                35                  40                  45

Leu Ser Gln Gln Arg Lys Leu Thr Leu Ala Ala Leu Val Glu Met Leu
                50                  55                  60

Tyr Val Leu Gln Arg Met Asp Leu Leu Lys Ser Arg Phe Gly Leu Ser
        65                  70                  75                  80

Lys Glu

<210> SEQ ID NO 8
<211> LENGTH: 86
<212> TYPE: PRT
<213> ORGANISM: Molluscum contagiosum virus

<400> SEQUENCE: 8

Leu Thr Arg Tyr Arg Lys Leu Met Val Cys Val Gly Glu Glu Leu Asp
        1               5                  10                 15

Ser Ser Glu Leu Arg Ala Leu Arg Leu Phe Ala Cys Asn Leu Asn Pro
                        20                  25                  30

Ser Leu Ser Thr Ala Leu Ser Glu Ser Ser Arg Phe Val Glu Leu Val
```

```
                35                  40                  45
Leu Ala Leu Glu Asn Val Gly Leu Val Ser Pro Ser Ser Val Ser Val
             50                  55                  60
Leu Ala Asp Met Leu Arg Thr Leu Arg Arg Leu Asp Leu Cys Gln Gln
 65                  70                  75                  80
Leu Val Glu Tyr Glu Gln
                 85

<210> SEQ ID NO 9
<211> LENGTH: 79
<212> TYPE: PRT
<213> ORGANISM: Molluscum contagiosum virus

<400> SEQUENCE: 9

Met Ala His Glu Pro Ile Pro Phe Ser Phe Leu Arg Asn Leu Leu Ala
  1               5                  10                  15
Glu Leu Asp Ala Ser Glu His Gly Val Leu Arg Phe Leu Cys Arg Asp
                 20                  25                  30
Val Ala Pro Ala Ser Lys Thr Ala Glu Asp Ala Leu Arg Ala Leu Gln
             35                  40                  45
Arg Arg Arg Leu Leu Thr Leu Ser Ser Met Ala Glu Leu Leu Cys Ala
         50                  55                  60
Leu Arg Arg Phe Asp Val Leu Lys Val Arg Phe Gly Met Thr Arg
 65                  70                  75

<210> SEQ ID NO 10
<211> LENGTH: 82
<212> TYPE: PRT
<213> ORGANISM: 'Axial Seamount' polynoid polychaete

<400> SEQUENCE: 10

Leu Ser Gln Tyr Arg Leu Gln Val Ala Ala Ile Asn Asn Met Val Gly
  1               5                  10                  15
Ser Glu Asp Leu Arg Val Met Cys Leu Cys Ala Gly Lys Leu Leu Pro
                 20                  25                  30
Pro Ser Cys Thr Pro Arg Cys Leu Val Asp Leu Val Ser Ala Leu Glu
             35                  40                  45
Asp Ala Gly Ala Ile Ser Pro Gln Asp Val Ser Val Leu Val Thr Leu
         50                  55                  60
Leu His Ala Val Cys Arg Tyr Asp Leu Ser Val Ala Leu Ser Ala Val
 65                  70                  75                  80
Ala His

<210> SEQ ID NO 11
<211> LENGTH: 83
<212> TYPE: PRT
<213> ORGANISM: Homo sapiens

<400> SEQUENCE: 11

Met Asp Phe Ser Arg Asn Leu Tyr Asp Ile Gly Glu Lys Leu Asp Ser
  1               5                  10                  15
Glu Asp Leu Ala Ser Leu Lys Phe Leu Ser Leu Asp Tyr Ile Pro Gln
                 20                  25                  30
Arg Lys Gln Glu Pro Ile Lys Asp Ala Leu Met Leu Phe Gln Arg Leu
             35                  40                  45
Gln Glu Lys Arg Met Leu Glu Glu Ser Asn Leu Ser Phe Leu Lys Glu
         50                  55                  60
```

-continued

```
Leu Leu Phe Arg Ile Asn Arg Leu Asp Leu Leu Ile Thr Tyr Leu Asn
 65                  70                  75                  80

Thr Arg Lys

<210> SEQ ID NO 12
<211> LENGTH: 83
<212> TYPE: PRT
<213> ORGANISM: Homo sapiens

<400> SEQUENCE: 12

Ile Ser Ala Tyr Arg Val Met Leu Tyr Gln Ile Ser Glu Glu Val Ser
 1               5                  10                  15

Arg Ser Glu Leu Arg Ser Phe Lys Phe Leu Gln Glu Glu Ile Ser
                20                  25                  30

Lys Cys Lys Leu Asp Asp Met Asn Leu Leu Asp Ile Phe Ile Glu
             35                  40                  45

Met Glu Lys Arg Val Ile Leu Gly Glu Gly Lys Leu Asp Ile Leu Lys
 50                  55                  60

Arg Val Cys Ala Gln Ile Asn Lys Ser Leu Leu Lys Ile Ile Asn Asp
 65                  70                  75                  80

Tyr Glu Glu

<210> SEQ ID NO 13
<211> LENGTH: 95
<212> TYPE: PRT
<213> ORGANISM: Homo sapiens

<400> SEQUENCE: 13

Met Lys Ser Gln Gly Gln His Trp Tyr Ser Ser Asp Lys Asn Cys
 1               5                  10                  15

Lys Val Ser Phe Arg Glu Lys Leu Leu Ile Ile Asp Ser Asn Leu Gly
                20                  25                  30

Val Gln Asp Val Glu Asn Leu Lys Phe Leu Cys Ile Gly Leu Val Pro
             35                  40                  45

Asn Lys Lys Leu Glu Lys Ser Ser Ala Ser Asp Val Phe Glu His
 50                  55                  60

Leu Leu Ala Gly Asp Leu Leu Ser Glu Glu Asp Pro Phe Phe Leu Ala
 65                  70                  75                  80

Glu Leu Leu Tyr Ile Ile Arg Gln Lys Lys Leu Leu Gln His Leu
                85                  90                  95

<210> SEQ ID NO 14
<211> LENGTH: 80
<212> TYPE: PRT
<213> ORGANISM: Homo sapiens

<400> SEQUENCE: 14

Val Ser Leu Phe Arg Asn Leu Leu Tyr Glu Leu Ser Glu Gly Ile Asp
 1               5                  10                  15

Ser Glu Asn Leu Lys Asp Met Ile Phe Leu Leu Lys Asp Ser Leu Pro
                20                  25                  30

Lys Thr Glu Met Thr Ser Leu Ser Phe Leu Ala Phe Leu Glu Lys Gln
             35                  40                  45

Gly Lys Ile Asp Glu Asp Asn Leu Thr Cys Leu Glu Asp Leu Cys Lys
 50                  55                  60

Thr Val Val Pro Lys Leu Leu Arg Asn Ile Glu Lys Tyr Lys Arg Glu
 65                  70                  75                  80
```

<210> SEQ ID NO 15
<211> LENGTH: 83
<212> TYPE: PRT
<213> ORGANISM: Homo sapiens

<400> SEQUENCE: 15

Met Asp Pro Phe Leu Val Leu Leu His Ser Val Ser Ser Leu Ser
 1               5                  10                  15

Ser Ser Glu Leu Thr Glu Leu Lys Phe Leu Cys Leu Gly Arg Val Gly
                20                  25                  30

Lys Arg Lys Leu Glu Arg Val Gln Ser Gly Leu Asp Leu Phe Ser Met
            35                  40                  45

Leu Leu Glu Gln Asn Asp Leu Glu Pro Gly His Thr Glu Leu Leu Arg
    50                  55                  60

Glu Leu Leu Ala Ser Leu Arg Arg His Asp Leu Leu Arg Arg Val Asp
65                  70                  75                  80

Asp Phe Glu

<210> SEQ ID NO 16
<211> LENGTH: 83
<212> TYPE: PRT
<213> ORGANISM: Homo sapiens

<400> SEQUENCE: 16

Met Val Glu Tyr Gly Thr Leu Phe Gln Asp Leu Thr Asn Asn Ile Thr
 1               5                  10                  15

Leu Glu Asp Leu Glu Gln Leu Lys Ser Ala Cys Lys Glu Asp Ile Pro
                20                  25                  30

Ser Glu Lys Ser Glu Ile Thr Thr Gly Ser Ala Trp Phe Ser Phe
            35                  40                  45

Leu Glu Ser His Asn Lys Leu Asp Lys Asp Asn Leu Ser Ile Ile Glu
    50                  55                  60

His Ile Phe Glu Ile Ser Arg Arg Pro Asp Leu Leu Thr Met Val Val
65                  70                  75                  80

Asp Tyr Arg

<210> SEQ ID NO 17
<211> LENGTH: 221
<212> TYPE: PRT
<213> ORGANISM: Homo sapiens

<400> SEQUENCE: 17

Met Ser Ala Glu Val Ile His Gln Val Glu Glu Ala Leu Asp Thr Asp
 1               5                  10                  15

Glu Lys Glu Met Leu Leu Phe Leu Cys Arg Asp Val Ala Ile Asp Val
                20                  25                  30

Val Pro Pro Asn Val Arg Asp Leu Leu Asp Ile Leu Arg Glu Arg Gly
            35                  40                  45

Lys Leu Ser Val Gly Asp Leu Ala Glu Leu Leu Tyr Arg Val Arg Arg
    50                  55                  60

Phe Asp Leu Leu Lys Arg Ile Leu Lys Met Asp Arg Lys Ala Val Glu
65                  70                  75                  80

Thr His Leu Leu Arg Asn Pro His Leu Val Ser Asp Tyr Arg Val Leu
                85                  90                  95

Met Ala Glu Ile Gly Glu Asp Leu Asp Lys Ser Asp Val Ser Ser Leu
            100                 105                 110

```
Ile Phe Leu Met Lys Asp Tyr Met Gly Arg Gly Lys Ile Ser Lys Glu
            115                 120                 125

Lys Ser Phe Leu Asp Leu Val Val Glu Leu Glu Lys Leu Asn Leu Val
        130                 135                 140

Ala Pro Asp Gln Leu Asp Leu Glu Lys Cys Leu Lys Asn Ile His
145                 150                 155                 160

Arg Ile Asp Leu Lys Thr Lys Ile Gln Lys Tyr Lys Gln Ser Val Gln
                165                 170                 175

Gly Ala Gly Thr Ser Tyr Arg Asn Val Leu Gln Ala Ala Ile Gln Lys
            180                 185                 190

Ser Leu Lys Asp Pro Ser Asn Asn Phe Arg Met Ile Thr Pro Tyr Ala
        195                 200                 205

His Cys Pro Asp Leu Lys Ile Leu Gly Asn Cys Ser Met
210                 215                 220

<210> SEQ ID NO 18
<211> LENGTH: 180
<212> TYPE: PRT
<213> ORGANISM: Homo sapiens

<400> SEQUENCE: 18

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile
    130                 135                 140

Glu Met Glu Lys Arg Val Ile Leu Gly Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu
            180

<210> SEQ ID NO 19
<211> LENGTH: 208
<212> TYPE: PRT
<213> ORGANISM: Homo sapiens

<400> SEQUENCE: 19

Met Asp Pro Phe Leu Val Leu Leu His Ser Val Ser Ser Ser Leu Ser
1               5                   10                  15

Ser Ser Glu Leu Thr Glu Leu Lys Phe Leu Cys Leu Gly Arg Val Gly
            20                  25                  30

Lys Arg Lys Leu Glu Arg Val Gln Ser Gly Leu Asp Leu Phe Ser Met
```

```
                35                  40                  45

Leu Leu Glu Gln Asn Asp Leu Glu Pro Gly His Thr Glu Leu Leu Arg
        50                  55                  60

Glu Leu Leu Ala Ser Leu Arg Arg His Asp Leu Leu Arg Arg Val Asp
65                  70                  75                  80

Asp Phe Glu Ala Gly Ala Ala Gly Ala Ala Pro Gly Glu Asp
                85                  90                  95
Leu Cys Ala Ala Phe Asn Val Ile Cys Asp Asn Asp Gly Lys Asp Trp
            100                 105                 110

Arg Arg Leu Ala Arg Gln Leu Lys Val Ser Asp Thr Lys Ile Asp Ser
        115                 120                 125

Ile Glu Asp Arg Tyr Pro Arg Asn Leu Thr Glu Arg Val Arg Glu Ser
    130                 135                 140

Leu Arg Ile Trp Lys Asn Thr Glu Lys Glu Asn Ala Thr Val Ala His
145                 150                 155                 160

Leu Val Gly Ala Leu Arg Ser Cys Gln Met Asn Leu Val Ala Asp Leu
                165                 170                 175

Val Gln Glu Val Gln Gln Ala Arg Asp Leu Gln Asn Arg Ser Gly Ala
            180                 185                 190

Met Ser Pro Met Ser Trp Asn Ser Asp Ala Ser Thr Ser Glu Ala Ser
        195                 200                 205

<210> SEQ ID NO 20
<211> LENGTH: 139
<212> TYPE: PRT
<213> ORGANISM: Molluscum contagiosum virus

<400> SEQUENCE: 20

Met Ala Thr Tyr Glu Val Leu Cys Glu Val Ala Arg Lys Leu Gly Thr
1               5                   10                  15

Asp Asp Arg Glu Val Val Leu Phe Leu Leu Asn Val Phe Ile Pro Gln
            20                  25                  30

Pro Thr Leu Ala Gln Leu Ile Gly Ala Leu Arg Ala Leu Lys Glu Glu
        35                  40                  45

Gly Arg Leu Thr Phe Pro Leu Leu Ala Glu Cys Leu Phe Arg Ala Gly
    50                  55                  60

Arg Arg Asp Leu Leu Arg Asp Leu Leu His Leu Asp Pro Arg Phe Leu
65                  70                  75                  80

Glu Arg His Leu Ala Gly Thr Met Ser Tyr Phe Ser Pro Tyr Gln Leu
                85                  90                  95

Thr Val Leu His Val Asp Gly Glu Leu Cys Ala Arg Asp Ile Arg Ser
            100                 105                 110

Leu Ile Phe Leu Ser Lys Asp Thr Ile Gly Ser Arg Ser Thr Pro Gln
        115                 120                 125

Thr Ser Tyr Thr Gly Cys Thr Val Trp Lys Thr
    130                 135

<210> SEQ ID NO 21
<211> LENGTH: 241
<212> TYPE: PRT
<213> ORGANISM: Molluscum contagiosum virus

<400> SEQUENCE: 21

Met Ser Asp Ser Lys Glu Val Pro Ser Leu Pro Phe Leu Arg His Leu
1               5                   10                  15

Leu Glu Glu Leu Asp Ser His Glu Asp Ser Leu Leu Leu Phe Leu Cys
            20                  25                  30
```

His Asp Ala Ala Pro Gly Cys Thr Thr Val Thr Gln Ala Leu Cys Ser
         35                  40                  45

Leu Ser Gln Gln Arg Lys Leu Thr Leu Ala Ala Leu Val Glu Met Leu
 50                  55                  60

Tyr Val Leu Gln Arg Met Asp Leu Leu Lys Ser Arg Phe Gly Leu Ser
 65                  70                  75                  80

Lys Glu Gly Ala Glu Gln Leu Leu Gly Thr Ser Phe Leu Thr Arg Tyr
                 85                  90                  95

Arg Lys Leu Met Val Cys Val Gly Glu Leu Asp Ser Ser Glu Leu
                100                 105                 110

Arg Ala Leu Arg Leu Phe Ala Cys Asn Leu Asn Pro Ser Leu Ser Thr
             115                 120                 125

Ala Leu Ser Glu Ser Ser Arg Phe Val Glu Leu Val Leu Ala Leu Glu
 130                 135                 140

Asn Val Gly Leu Val Ser Pro Ser Ser Val Ser Val Leu Ala Asp Met
 145                 150                 155                 160

Leu Arg Thr Leu Arg Arg Leu Asp Leu Cys Gln Gln Leu Val Glu Tyr
                 165                 170                 175

Glu Gln Gln Glu Gln Ala Arg Tyr Arg Tyr Cys Tyr Ala Ala Ser Pro
             180                 185                 190

Ser Leu Pro Val Arg Thr Leu Arg Arg Gly His Gly Ala Ser Glu His
         195                 200                 205

Glu Gln Leu Cys Met Pro Val Gln Glu Ser Ser Asp Ser Pro Glu Leu
             210                 215                 220

Leu Arg Thr Pro Val Gln Glu Ser Ser Ser Asp Ser Pro Gln Thr
 225                 230                 235                 240

Thr

<210> SEQ ID NO 22
<211> LENGTH: 371
<212> TYPE: PRT
<213> ORGANISM: Molluscum contagiosum virus

<400> SEQUENCE: 22

Met Ala His Glu Pro Ile Pro Phe Ser Phe Leu Arg Asn Leu Leu Ala
  1               5                  10                  15

Glu Leu Asp Ala Ser Glu His Glu Val Leu Arg Phe Leu Cys Arg Asp
                 20                  25                  30

Val Ala Pro Ala Ser Lys Thr Ala Glu Asp Ala Leu Arg Ala Leu Gln
             35                  40                  45

Arg Arg Arg Leu Leu Thr Leu Ser Ser Met Ala Glu Leu Leu Cys Ala
 50                  55                  60

Leu Arg Arg Phe Asp Val Leu Lys Val Arg Phe Gly Met Thr Arg Glu
 65                  70                  75                  80

Cys Ala Gly Arg Leu Leu Gly His Gly Phe Leu Ser Gln Tyr Arg Leu
                 85                  90                  95

Gln Val Ala Ala Ile Asn Asn Met Val Gly Ser Glu Asp Leu Arg Val
            100                 105                 110

Met Cys Leu Cys Ala Gly Lys Leu Leu Pro Pro Ser Cys Thr Pro Arg
         115                 120                 125

Cys Leu Val Asp Leu Val Ser Ala Leu Glu Asp Ala Gly Ala Ile Ser
 130                 135                 140

Pro Gln Asp Val Ser Val Leu Val Thr Leu Leu His Ala Val Cys Arg
 145                 150                 155                 160

```
Tyr Asp Leu Ser Val Ala Leu Ser Ala Val Ala His Gly His Met Thr
            165                 170                 175

Val Gly Val Gly Thr Pro Val Gln Asp Glu Pro Met Asp Val Leu Glu
            180                 185                 190

Val Asp Asp Ala Glu Pro Met Glu Ala Thr Pro Ala Cys Asp Glu Ile
            195                 200                 205

Gly Val Val Lys Leu Ala Gly Ala Ser Ala Gly Ala Pro Leu Ala
            210                 215                 220

Asp Gly Ala Phe Ala Ala Cys Thr Ser Ala Lys Gly Glu Asp Leu
225                 230                 235                 240

Ala Thr Ser Asp Leu Thr Asp Ser Glu Pro Glu Asp Ser Val Phe Ala
            245                 250                 255

Val Ala Asp Pro Val Tyr Ala Asp Val Asp Leu Ser Met Phe Val Arg
            260                 265                 270

Ala Asn Ala Thr Ala Asp Ser Ser Met Phe Val Asn Ala Asp Ala Gly
            275                 280                 285

Ala Asp Ser Ser Leu Val Asn Ala Asp Ala Gly Ala Asp Ser Ser Leu
            290                 295                 300

Val Asn Ala Asp Ala Gly Ala Asp Ser Ser Leu Val Asn Ala Val Ala
305                 310                 315                 320

Asp Ala Asn Ser Ser Leu Met Arg Thr Thr Ser Ala Cys Thr Asp Ser
                        325                 330                 335

Glu Pro Glu Asp Ser Ala Gly Pro Ser Cys Ala Gly Met Ala Leu Ser
                        340                 345                 350

Met Phe Gly Arg Ala Lys Ser Val Ser Ser Leu Leu Leu Arg Thr Lys
                        355                 360                 365

Ala Ser Thr
            370

<210> SEQ ID NO 23
<211> LENGTH: 171
<212> TYPE: PRT
<213> ORGANISM: Equine Herpesvirus

<400> SEQUENCE: 23

Met Ser His Tyr Ser Met Ile Asp Thr Tyr Phe Ser Leu Asp Glu Asp
  1               5                  10                  15

Glu Thr Glu Thr Tyr Leu Tyr Leu Cys Arg Asp Leu Leu Lys Asn Lys
                 20                  25                  30

Gly Glu Phe Gln Cys Thr Arg Asp Ala Phe Lys Phe Leu Ser Asp Tyr
             35                  40                  45

Ala Cys Leu Ser Ala Ala Asn Gln Met Glu Leu Leu Phe Arg Val Gly
         50                  55                  60

Arg Leu Asp Leu Ile Arg Arg Ile Phe Gly Gln Thr Trp Thr Pro Asp
 65                  70                  75                  80

Ser Cys Pro Arg Tyr Tyr Met Pro Ile Cys Ser Pro Phe Arg Cys Leu
                 85                  90                  95

Met Ala Leu Val Asn Asp Phe Leu Ser Asp Leu Glu Val Glu Glu Met
                100                 105                 110

Tyr Phe Leu Cys Ala Pro Arg Leu Glu Ser His Leu Glu Pro Gly Ser
            115                 120                 125

Lys Lys Ser Phe Leu Arg Leu Ala Ser Leu Leu Glu Asp Leu Glu Leu
        130                 135                 140

Leu Gly Gly Asp Lys Leu Thr Phe Leu Arg His Leu Leu Thr Thr Ile
```

```
                145                 150                 155                 160

Gly Arg Ala Asp Leu Val Lys Asn Leu Gln Val
                165                 170

<210> SEQ ID NO 24
<211> LENGTH: 130
<212> TYPE: PRT
<213> ORGANISM: Homo sapiens

<400> SEQUENCE: 24

Met Val Glu Tyr Gly Thr Leu Phe Gln Asp Leu Thr Asn Asn Ile Thr
  1               5                  10                  15

Leu Glu Asp Leu Glu Gln Leu Lys Ser Ala Cys Lys Glu Asp Ile Pro
                 20                  25                  30

Ser Glu Lys Ser Glu Glu Ile Thr Thr Gly Ser Ala Trp Phe Ser Phe
             35                  40                  45

Leu Glu Ser His Asn Lys Leu Asp Lys Asp Asn Leu Ser Ile Ile Glu
         50                  55                  60

His Ile Phe Glu Ile Ser Arg Arg Pro Asp Leu Leu Thr Met Val Val
 65                  70                  75                  80

Asp Tyr Arg Thr Arg Val Leu Lys Ile Ser Glu Glu Asp Glu Leu Asp
                 85                  90                  95

Thr Lys Leu Thr Arg Ile Pro Ser Ala Lys Lys Tyr Lys Asp Ile Ile
                100                 105                 110

Arg Gln Pro Ser Glu Glu Ile Ile Lys Leu Gly Pro Pro Lys
            115                 120                 125

Lys Ala
    130

<210> SEQ ID NO 25
<211> LENGTH: 210
<212> TYPE: PRT
<213> ORGANISM: Homo sapiens

<400> SEQUENCE: 25

Met Lys Ser Gln Gly Gln His Trp Tyr Ser Ser Asp Lys Asn Cys
  1               5                  10                  15

Lys Val Ser Phe Arg Glu Lys Leu Leu Ile Ile Asp Ser Asn Leu Gly
                 20                  25                  30

Val Gln Asp Val Glu Asn Leu Lys Phe Leu Cys Ile Gly Leu Val Pro
             35                  40                  45

Asn Lys Lys Leu Glu Lys Ser Ser Ala Ser Asp Val Phe Glu His
         50                  55                  60

Leu Leu Ala Gly Asp Leu Leu Ser Glu Glu Asp Pro Phe Phe Leu Ala
 65                  70                  75                  80

Glu Leu Leu Tyr Ile Ile Arg Gln Lys Lys Leu Leu Gln His Leu Asn
                 85                  90                  95

Cys Thr Lys Glu Glu Val Glu Arg Leu Leu Pro Thr Arg Gln Arg Val
                100                 105                 110

Ser Leu Phe Arg Asn Leu Leu Tyr Glu Leu Ser Glu Gly Ile Asp Ser
            115                 120                 125

Glu Asn Leu Lys Asp Met Ile Phe Leu Leu Lys Asp Ser Leu Pro Lys
        130                 135                 140

Thr Glu Met Thr Ser Leu Ser Phe Leu Ala Phe Leu Glu Lys Gln Gly
145                 150                 155                 160

Lys Ile Asp Glu Asp Asn Leu Thr Cys Leu Glu Asp Leu Cys Lys Thr
```

```
                      165                 170                 175
Val Val Pro Lys Leu Leu Arg Asn Ile Glu Lys Tyr Lys Arg Glu Lys
            180                 185                 190

Ala Ile Gln Ile Val Thr Pro Pro Val Asp Lys Glu Ala Glu Ser Tyr
        195                 200                 205

Gln Gly
    210

<210> SEQ ID NO 26
<211> LENGTH: 479
<212> TYPE: PRT
<213> ORGANISM: Homo sapiens

<400> SEQUENCE: 26

Met Asp Phe Ser Arg Asn Leu Tyr Asp Ile Gly Glu Gln Leu Asp Ser
  1               5                  10                  15

Glu Asp Leu Ala Ser Leu Lys Phe Leu Ser Leu Asp Tyr Ile Pro Gln
             20                  25                  30

Arg Lys Gln Glu Pro Ile Lys Asp Ala Leu Met Leu Phe Gln Arg Leu
         35                  40                  45

Gln Glu Lys Arg Met Leu Glu Glu Ser Asn Leu Ser Phe Leu Lys Glu
     50                  55                  60

Leu Leu Phe Arg Ile Asn Arg Leu Ala Leu Leu Ile Thr Tyr Leu Asn
 65                  70                  75                  80

Thr Arg Lys Glu Glu Met Glu Arg Glu Leu Gln Thr Pro Gly Arg Ala
                 85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile
    130                 135                 140

Glu Met Ile Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Glu Arg Ser Ser Ser Leu Glu Gly Ser
            180                 185                 190

Pro Asp Glu Phe Ser Asn Gly Glu Glu Leu Cys Gly Val Met Thr Ile
        195                 200                 205

Ser Asp Ser Pro Arg Glu Gln Asp Ser Glu Ser Gln Thr Leu Asp Lys
    210                 215                 220

Val Tyr Gln Met Lys Ser Lys Pro Arg Gly Tyr Cys Leu Ile Ile Asn
225                 230                 235                 240

Asn His Asn Phe Ala Lys Ala Arg Glu Lys Val Pro Lys Leu His Ser
                245                 250                 255

Ile Arg Asp Arg Asn Gly Thr His Leu Asp Ala Gly Ala Leu Thr Thr
            260                 265                 270

Thr Phe Glu Glu Leu His Phe Glu Ile Lys Pro His Asp Asp Cys Thr
        275                 280                 285

Val Glu Gln Ile Tyr Glu Ile Leu Lys Ile Tyr Gln Leu Met Asp His
    290                 295                 300

Ser Asn Met Asp Cys Phe Ile Cys Cys Ile Leu Ser His Gly Asp Lys
305                 310                 315                 320
```

```
Gly Ile Ile Tyr Gly Thr Asp Gly Gln Glu Pro Pro Ile Tyr Glu Leu
                325                 330                 335

Thr Ser Gln Phe Thr Gly Leu Lys Cys Pro Ser Leu Ala Gly Lys Pro
                340                 345                 350

Lys Val Phe Phe Ile Gln Ala Cys Gln Gly Asp Asn Tyr Gln Lys Gly
                355                 360                 365

Ile Pro Val Glu Thr Asp Ser Glu Glu Gln Pro Tyr Leu Glu Met Asp
        370                 375                 380

Leu Ser Ser Pro Gln Thr Arg Tyr Ile Pro Asp Glu Ala Asp Phe Leu
385                 390                 395                 400

Leu Gly Met Ala Thr Val Asn Asn Cys Val Ser Tyr Arg Asn Pro Ala
                405                 410                 415

Glu Gly Thr Trp Tyr Ile Gln Ser Leu Cys Gln Ser Leu Arg Glu Arg
                420                 425                 430

Cys Pro Arg Gly Asp Asp Ile Leu Thr Ile Leu Thr Glu Val Asn Tyr
                435                 440                 445

Glu Val Ser Asn Lys Asp Asp Lys Asn Met Gly Lys Gln Met Pro
                450                 455                 460

Gln Pro Thr Phe Thr Leu Arg Lys Lys Leu Val Phe Pro Ser Asp
465                 470                 475

<210> SEQ ID NO 27
<211> LENGTH: 479
<212> TYPE: PRT
<213> ORGANISM: Homo sapiens

<400> SEQUENCE: 27

Met Asp Phe Ser Arg Asn Leu Tyr Asp Ile Gly Glu Gln Leu Asp Ser
  1               5                  10                  15

Glu Asp Leu Ala Ser Leu Lys Phe Leu Ser Leu Asp Tyr Ile Pro Gln
                 20                  25                  30

Arg Lys Gln Glu Pro Ile Lys Asp Ala Leu Met Leu Phe Gln Arg Leu
             35                  40                  45

Gln Glu Lys Arg Met Leu Glu Ser Asn Leu Ser Phe Leu Lys Glu
         50                  55                  60

Leu Leu Phe Arg Ile Asn Arg Leu Asp Ala Leu Ile Thr Tyr Leu Asn
 65                  70                  75                  80

Thr Arg Lys Glu Glu Met Glu Arg Glu Leu Gln Thr Pro Gly Arg Ala
                 85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
            115                 120                 125

Ser Lys Cys Lys Leu Asp Asp Asp Met Asn Leu Leu Asp Ile Phe Ile
        130                 135                 140

Glu Asn Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Glu Arg Ser Ser Ser Leu Glu Gly Ser
            180                 185                 190

Pro Asp Glu Phe Ser Asn Gly Glu Glu Leu Cys Gly Val Met Thr Ile
        195                 200                 205

Ser Asp Ser Pro Arg Glu Gln Asp Ser Glu Ser Gln Thr Leu Asp Lys
210                 215                 220
```

```
Val Tyr Gln Met Lys Ser Lys Pro Arg Gly Tyr Cys Leu Ile Ile Asn
225                 230                 235                 240

Asn His Asn Phe Ala Lys Ala Arg Glu Lys Val Pro Lys Leu His Ser
                245                 250                 255

Ile Arg Asp Arg Asn Gly Thr His Leu Asp Ala Gly Ala Leu Thr Thr
            260                 265                 270

Thr Phe Glu Glu Leu His Phe Glu Ile Lys Pro His Asp Asp Cys Thr
        275                 280                 285

Val Glu Gln Ile Tyr Glu Ile Leu Lys Ile Tyr Gln Leu Met Asp His
290                 295                 300

Ser Asn Met Asp Cys Phe Ile Cys Cys Ile Leu Ser His Gly Asp Lys
305                 310                 315                 320

Gly Ile Ile Tyr Gly Thr Asp Gly Gln Glu Pro Pro Ile Tyr Glu Leu
                325                 330                 335

Thr Ser Gln Phe Thr Gly Leu Lys Cys Pro Ser Leu Ala Gly Lys Pro
            340                 345                 350

Lys Val Phe Phe Ile Gln Ala Cys Gln Gly Asp Asn Tyr Gln Lys Gly
        355                 360                 365

Ile Pro Val Glu Thr Asp Ser Glu Glu Gln Pro Tyr Leu Glu Met Asp
370                 375                 380

Leu Ser Ser Pro Gln Thr Arg Tyr Ile Pro Asp Glu Ala Asp Phe Leu
385                 390                 395                 400

Leu Gly Met Ala Thr Val Asn Asn Cys Val Ser Tyr Arg Asn Pro Ala
                405                 410                 415

Glu Gly Thr Trp Tyr Ile Gln Ser Leu Cys Gln Ser Leu Arg Glu Arg
            420                 425                 430

Cys Pro Arg Gly Asp Asp Ile Leu Thr Ile Leu Thr Glu Val Asn Tyr
        435                 440                 445

Glu Asp Ser Asn Lys Asp Asp Lys Lys Asn Met Gly Lys Gln Met Pro
450                 455                 460

Gln Pro Thr Phe Thr Leu Arg Lys Lys Leu Val Phe Pro Ser Asp
465                 470                 475

<210> SEQ ID NO 28
<211> LENGTH: 479
<212> TYPE: PRT
<213> ORGANISM: Homo sapiens

<400> SEQUENCE: 28

Met Asp Phe Ser Arg Asn Leu Tyr Asp Ile Gly Glu Gln Leu Asp Ser
 1               5                  10                  15

Glu Asp Leu Ala Ser Leu Lys Phe Leu Ser Leu Asp Tyr Ile Pro Gln
                20                  25                  30

Arg Lys Gln Glu Pro Ile Lys Asp Ala Leu Met Leu Phe Gln Arg Leu
            35                  40                  45

Gln Glu Lys Arg Met Leu Glu Glu Ser Asn Leu Ser Phe Leu Lys Glu
        50                  55                  60

Leu Leu Phe Arg Ile Asn Arg Leu Asp Leu Ala Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
```

```
            115                 120                 125
Ser Lys Cys Lys Leu Asp Asp Asp Met Asn Leu Leu Asp Ile Phe Ile
130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Glu Arg Ser Ser Ser Leu Glu Gly Ser
            180                 185                 190

Pro Asp Glu Phe Ser Asn Gly Glu Glu Leu Cys Gly Val Met Thr Ile
            195                 200                 205

Ser Asp Ser Pro Arg Glu Gln Asp Ser Glu Ser Gln Thr Leu Asp Lys
210                 215                 220

Val Tyr Gln Met Lys Ser Lys Pro Arg Gly Tyr Cys Leu Ile Ile Asn
225                 230                 235                 240

Asn His Asn Phe Ala Lys Ala Arg Glu Lys Val Pro Lys Leu His Ser
                245                 250                 255

Ile Arg Asp Arg Asn Gly Thr His Leu Asp Ala Gly Ala Leu Thr Thr
            260                 265                 270

Thr Phe Glu Glu Leu His Phe Glu Ile Lys Pro His Asp Asp Cys Thr
            275                 280                 285

Val Glu Gln Ile Tyr Glu Ile Leu Lys Ile Tyr Gln Leu Met Asp His
290                 295                 300

Ser Asn Met Asp Cys Phe Ile Cys Cys Ile Leu Ser His Gly Asp Lys
305                 310                 315                 320

Gly Ile Ile Tyr Gly Thr Asp Gly Gln Glu Pro Pro Ile Tyr Glu Leu
                325                 330                 335

Thr Ser Gln Phe Thr Gly Leu Lys Cys Pro Ser Leu Ala Gly Lys Pro
            340                 345                 350

Lys Val Phe Phe Ile Gln Ala Cys Gln Gly Asp Asn Tyr Gln Lys Gly
            355                 360                 365

Ile Pro Val Glu Thr Asp Ser Glu Glu Gln Pro Tyr Leu Glu Met Asp
370                 375                 380

Leu Ser Ser Pro Gln Thr Arg Tyr Ile Pro Asp Glu Ala Asp Phe Leu
385                 390                 395                 400

Leu Gly Met Ala Thr Val Asn Asn Cys Val Ser Tyr Arg Asn Pro Ala
                405                 410                 415

Glu Gly Thr Trp Tyr Ile Gln Ser Leu Cys Gln Ser Leu Arg Glu Arg
            420                 425                 430

Cys Pro Arg Gly Asp Asp Ile Leu Thr Ile Leu Thr Glu Val Asn Tyr
            435                 440                 445

Glu Val Ser Asn Lys Asp Asp Lys Lys Asn Met Gly Lys Gln Met Pro
450                 455                 460

Gln Pro Thr Phe Thr Leu Arg Lys Lys Leu Val Phe Pro Ser Asp
465                 470                 475
```

<210> SEQ ID NO 29
<211> LENGTH: 41
<212> TYPE: DNA
<213> ORGANISM: Homo sapiens

<400> SEQUENCE: 29 gtgttttta ttcaggctag tcagggggat aactaccaga a           41

-continued

```
<210> SEQ ID NO 30
<211> LENGTH: 41
<212> TYPE: DNA
<213> ORGANISM: Homo sapiens

<400> SEQUENCE: 30
ttctggtagt tatcccctg actagcctga ataaaaaaca c                    41

<210> SEQ ID NO 31
<211> LENGTH: 24
<212> TYPE: DNA
<213> ORGANISM: Homo sapiens

<400> SEQUENCE: 31
taatagactg gctttgctga ttac                                      24

<210> SEQ ID NO 32
<211> LENGTH: 24
<212> TYPE: DNA
<213> ORGANISM: Homo sapiens

<400> SEQUENCE: 32
gtaatcagca aagccagtct atta                                      24

<210> SEQ ID NO 33
<211> LENGTH: 24
<212> TYPE: DNA
<213> ORGANISM: Homo sapiens

<400> SEQUENCE: 33
aatagactgg atgcgctgat tacc                                      24

<210> SEQ ID NO 34
<211> LENGTH: 24
<212> TYPE: DNA
<213> ORGANISM: Homo sapiens

<400> SEQUENCE: 34
ggtaatcagc gcatccagtc tatt                                      24

<210> SEQ ID NO 35
<211> LENGTH: 24
<212> TYPE: DNA
<213> ORGANISM: Homo sapiens

<400> SEQUENCE: 35
gactggattt ggcgattacc tacc                                      24

<210> SEQ ID NO 36
<211> LENGTH: 24
<212> TYPE: DNA
<213> ORGANISM: Homo sapiens

<400> SEQUENCE: 36
ggtaggtaat cgccaaatcc agtc                                      24

<210> SEQ ID NO 37
<211> LENGTH: 29
<212> TYPE: DNA
<213> ORGANISM: Homo sapiens

<400> SEQUENCE: 37
tcttcattca ggctagccga gggaccgag                                 29
```

-continued

```
<210> SEQ ID NO 38
<211> LENGTH: 29
<212> TYPE: DNA
<213> ORGANISM: Homo sapiens

<400> SEQUENCE: 38
ctcggtccct cggctagcct gaatgaaga                                29

<210> SEQ ID NO 39
<211> LENGTH: 25
<212> TYPE: DNA
<213> ORGANISM: Homo sapiens

<400> SEQUENCE: 39
ttcatccagg ccagtggtgg ggagc                                    25

<210> SEQ ID NO 40
<211> LENGTH: 25
<212> TYPE: DNA
<213> ORGANISM: Homo sapiens

<400> SEQUENCE: 40
gctccccacc actggcctgg atgaa                                    25
```